United States Patent
Loring et al.

(10) Patent No.: US 8,442,772 B2
(45) Date of Patent: May 14, 2013

(54) COMPOSITIONS AND METHODS FOR DEFINING CELLS

(75) Inventors: Jeanne F. Loring, Del Mar, CA (US); Franz-Josef Müller, Kiel (DE)

(73) Assignee: Jeanne F. Loring, San Diego, CA (US)

( * ) Notice: Subject to any disclaimer, the term of this patent is extended or adjusted under 35 U.S.C. 154(b) by 0 days.

(21) Appl. No.: 12/806,779

(22) Filed: Aug. 20, 2010

(65) Prior Publication Data

US 2011/0118130 A1 May 19, 2011

Related U.S. Application Data

(60) Provisional application No. 61/236,124, filed on Aug. 23, 2009, provisional application No. 61/274,958, filed on Aug. 24, 2009.

(51) Int. Cl.
*G06F 19/00* (2011.01)
*A01N 63/00* (2006.01)

(52) U.S. Cl.
USPC ......... 702/19; 424/93.1; 424/93.21; 424/93.7

(58) Field of Classification Search ................ None
See application file for complete search history.

(56) References Cited

PUBLICATIONS

Muller et al. (Nature (2008) vol. 455, p. 401-406; published online Aug. 24, 2008).*
Liu et al. (BMC Developmental Biology (2006) vol. 6, pp. 1-16).*
Brunet et al. (PNAS (2004) vol. 101, No. 12, pp. 4164-4169).*

* cited by examiner

*Primary Examiner* — Lori A Clow
(74) *Attorney, Agent, or Firm* — Convergent Law Group LLP

(57) ABSTRACT

Disclosed are compositions and methods for classifying stem cells. The disclosure provides a way to define cells using a computational analysis.

27 Claims, 58 Drawing Sheets

Legend

| | |
|---|---|
| Clusters composed of one Sample Type with Number of Samples (e.g. 15) | |
| ePSC-UN (Undifferentiated hESC) |  |
|  B-NLin ("fetal brain derived NSC") | |
| ePSC-NLin ("hESC derived NSC") |  |
|  B-NLin ("HANSE, adult brain") | |
| Clusters composed of more than one Sample Type (e.g. 30) | |
| e.g. other Sample Types and ePSC-UN (Undifferentiated hESC) |  |
| Colored number indicates samples of the same type as the colored squares | |
| Grey number indicates the Rest of the Samples in the Cluster | |
|  | clusters composed only of other sample types. |

FIG. 4A, FIG. 4B, FIG. 4C and FIG. 4D CONTINUED

FIG. 5A
FIG. 5B
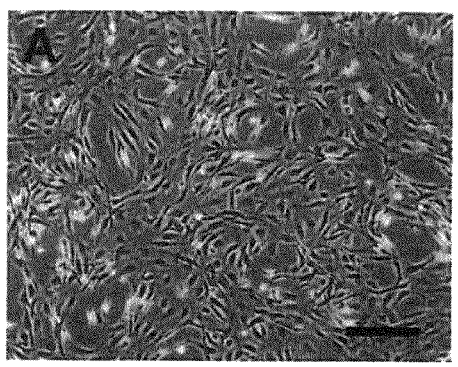 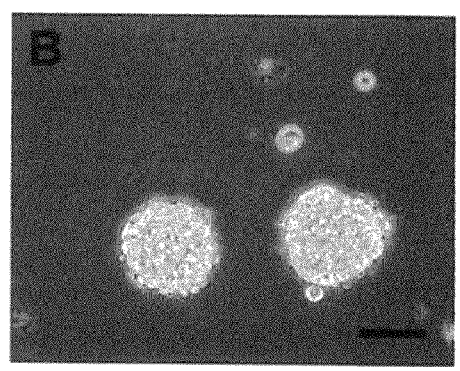

A    Pairwise Single Gene Analysis Matrix

| | | 10 | 100 | 219 | 114 | 236 | 1 | 176 | 68 | 149 | 113 | 56 | 68 |
|---|---|---|---|---|---|---|---|---|---|---|---|---|---|
| 12 | 17 | 39 | 12 | 467 | 285 | 633 | 332 | 618 | 237 | 177 | 447 | 336 | 285 |
| 6 | 32 | 725 | 1254 | 6 | 41 | 86 | 490 | 389 | 229 | 110 | 155 | 34 | 98 |
| 4 | 4 | 49 | 759 | 251 | 4 | 3 | 598 | 654 | 11 | 47 | 46 | 2 | 375 |
| 3 | 12 | 147 | 688 | 813 | 22 | 3 | 724 | 644 | 114 | 67 | 68 | 25 | 185 |
| 9 | 20 | 61 | 128 | 821 | 145 | 260 | 9 | 143 | 18 | 97 | 95 | 46 | 92 |
| | | 265 | 431 | 1287 | 274 | 553 | 448 | | 43 | 207 | 458 | 213 | 409 |
| | | 86 | 237 | 668 | 56 | 186 | 93 | 67 | 5 | 37 | 95 | 0 | 167 |
| 8 | 6 | 214 | 195 | 445 | 29 | 61 | 54 | 97 | 0 | 8 | 6 | 0 | 103 |
| | | 87 | 446 | 715 | 48 | 177 | 266 | 504 | 15 | 9 | 11 | 1 | 23 |
| | | 250 | 482 | 554 | 25 | 102 | 213 | 240 | 0 | 63 | 42 | 7 | 97 |
| | | 72 | 411 | 834 | 143 | 262 | 230 | 392 | 64 | 99 | 19 | 57 | 2 |

Number of Samples in each Cluster
Cluster Number

FIG. 6A

B Pairwise Gene Set Analysis Matrix

| 10 | 5  | 84 | 43 | 35 | 16 | 3 | 67 | 21 | 6  | 14 | 3  |
|----|----|----|----|----|----|---|----|----|----|----|----|
| 2  | 12 | 15 | 19 | 10 | 10 | 0 | 38 | 2  | 9  | 3  | 1  |
| 6  | 3  | 6  | 10 | 0  | 1  | 6 | 3  | 6  | 10 | 1  | 10 |
| 11 | 5  | 3  | 4  | 1  | 2  | 3 | 5  | 20 | 30 | 2  | 6  |
| 5  | 3  | 1  | 14 | 3  | 22 | 12| 61 | 6  | 11 | 0  | 8  |
| 1  | 1  | 13 | 15 | 6  | 9  | 1 | 4  | 9  | 1  | 5  | 5  |
| 0  | 1  | 6  | 5  | 8  | 1  |   | 1  | 11 | 4  | 4  | 8  |
| 0  | 2  | 1  | 20 | 5  | 1  | 1 |    | 18 | 19 | 0  | 8  |
| 6  | 0  | 4  | 12 | 6  | 0  | 2 | 17 | 8  | 16 | 16 | 11 |
| 7  | 1  | 42 | 37 | 50 | 8  | 5 | 0  | 63 | 11 | 5  | 1  |
| 4  | 0  | 1  | 1  | 5  | 2  | 2 | 4  | 18 | 2  | 7  | 0  |
| 2  | 0  | 64 | 19 | 60 | 0  | 6 | 1  | 50 | 2  | 1  | 2  |

Legend:
Front Node ● ● Back Node

Gene bound by:
OCT4 □ ○ NANOG
SOX2 ▱ ○ NANOG OCT4
OCT4 SOX2 ◇ ○ NANOG SOX2
△ NANOG SOX2 OCT4

— Protein-Protein Interaction

= Protein-Protein Interaction from Wang et al. 2006

FIG. 9A    FIG. 9B
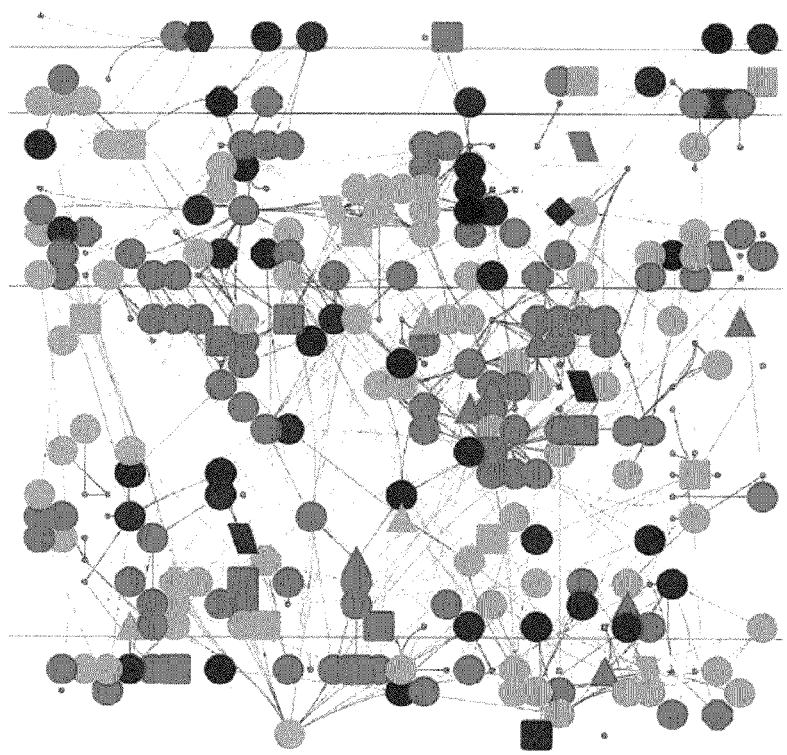
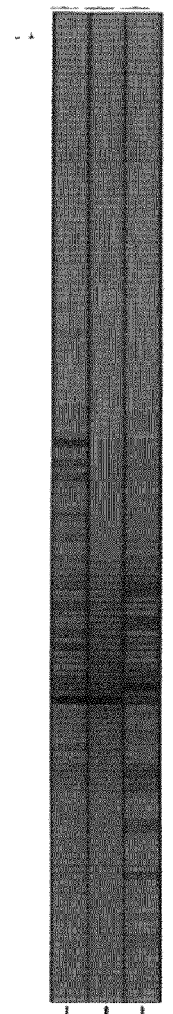
FIG. 9C
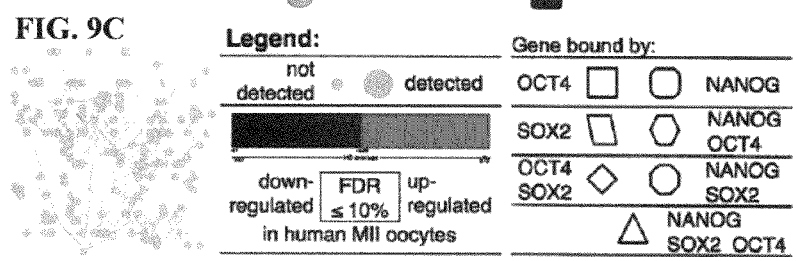
arrays 1-3 (10 oocytes each) normalized to 3 arrays hybridized with RNA from normal tissues

FIG. 9D

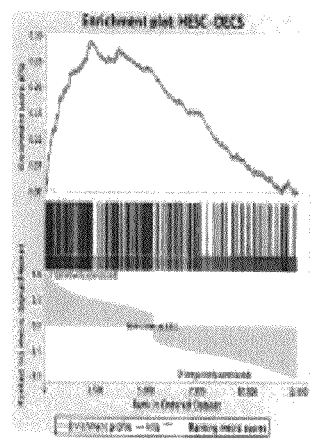

| GSEA | Dataset | The transcriptome of human oocytes - Kocabas 2006 |
|---|---|---|
| | Phenotypes | human MII oocytes vs. pooled human reference RNA from tissues |
| | Upregulated in | Oocytes |
| | Enrichment score (ES) | 0.28998774 |
| | Normalized Enrichment Score | 3.0398402 |
| | Nominal p-value | < 0.001 (permutation type: gene set*) |
| | FDR q-value | < 0.001 (permutation type: gene set*) |
| | FWER q-value | < 0.001 (permutation type: gene set*) |

* Gene set permutation was performed because the number of samples in each class was < 7.

FIG. 10A,
FIG. 10B,
FIG. 10C,
FIG. 10D,
FIG. 10E,
FIG. 10F and

FIG. 15A
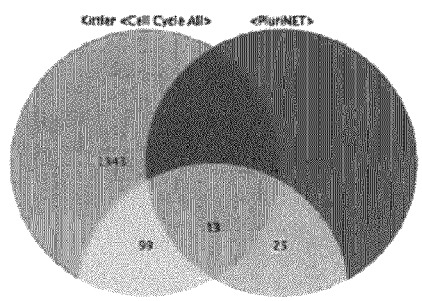
FIG. 15B
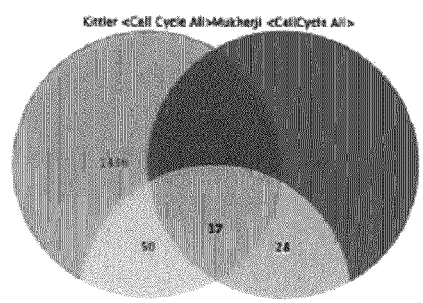
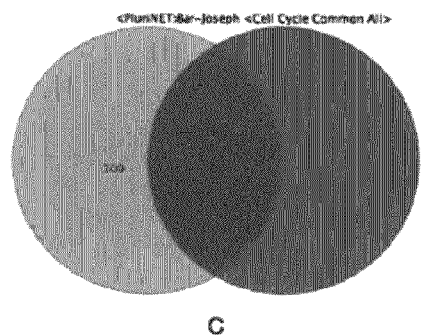
FIG. 15C

FIG. 16B

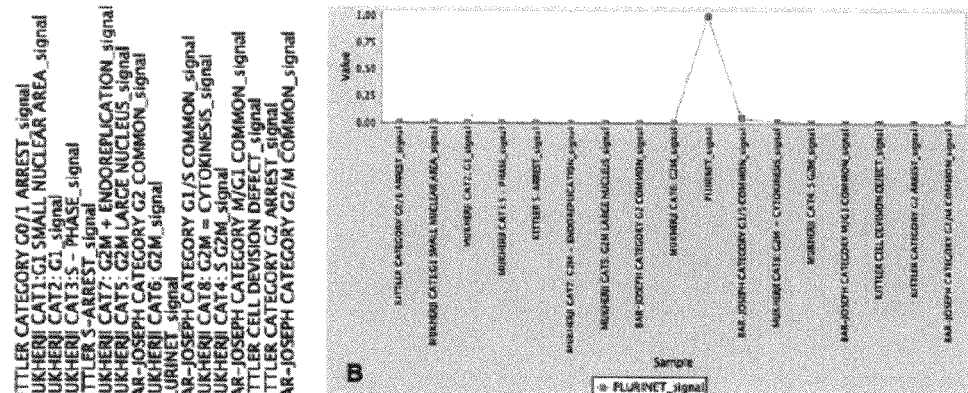

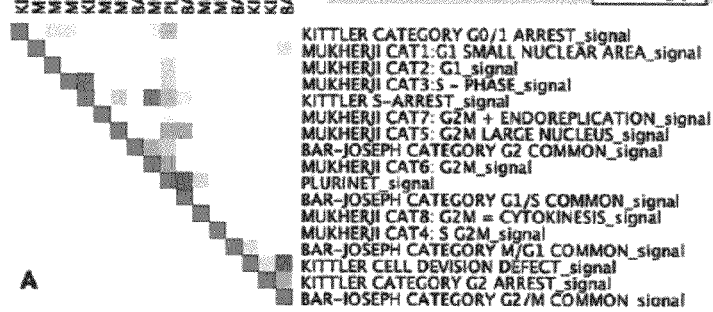

KITTLER CATEGORY G0/1 ARREST_signal
MUKHERJI CAT1:G1 SMALL NUCLEAR AREA_signal
MUKHERJI CAT2: G1_signal
MUKHERJI CAT3:S - PHASE_signal
KITTLER S-ARREST_signal
MUKHERJI CAT7: G2M + ENDOREPLICATION_signal
MUKHERJI CAT5: G2M LARGE NUCLEUS_signal
BAR-JOSEPH CATEGORY G2 COMMON_signal
MUKHERJI CAT6: G2M_signal
PLURINET_signal
BAR-JOSEPH CATEGORY G1/S COMMON_signal
MUKHERJI CAT8: G2M = CYTOKINESIS_signal
MUKHERJI CAT4: S G2M_signal
BAR-JOSEPH CATEGORY M/G1 COMMON_signal
KITTLER CELL DEVISION DEFECT_signal
KITTLER CATEGORY G2 ARREST_signal
BAR-JOSEPH CATEGORY G2/M COMMON_signal

FIG. 16A

FIG. 19A
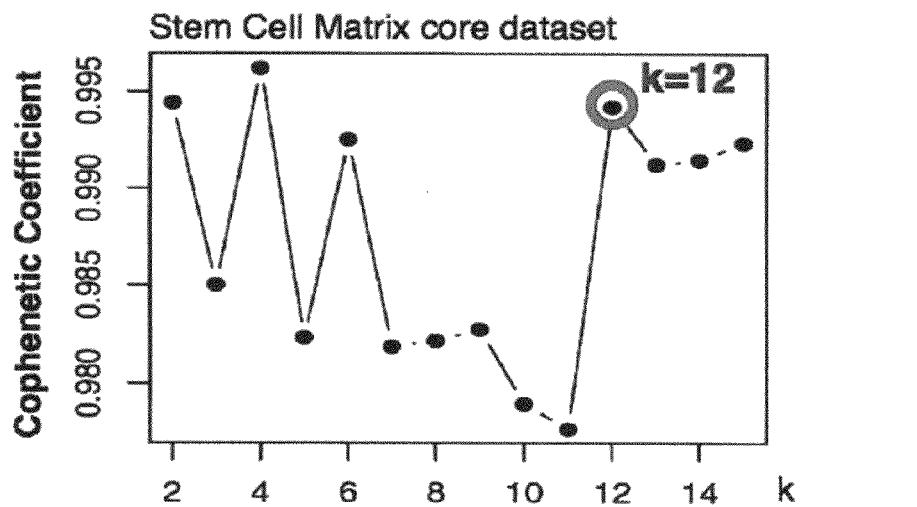
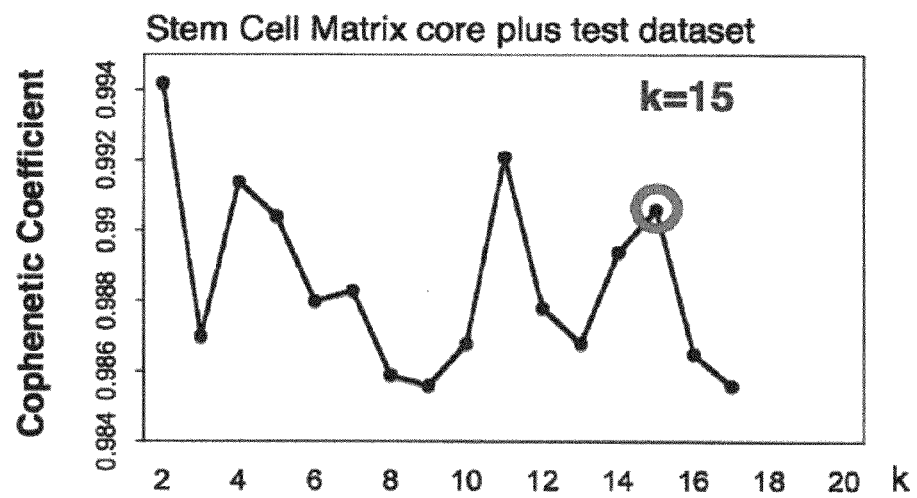
FIG. 19B

Model Selection

Consensus Matrix

FIG. 21B             FIG. 21C
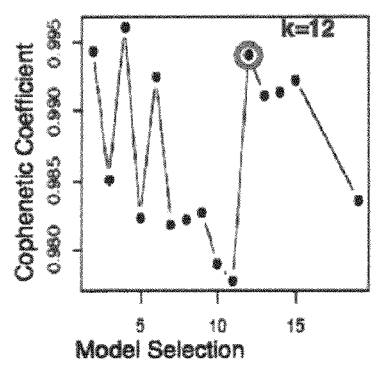 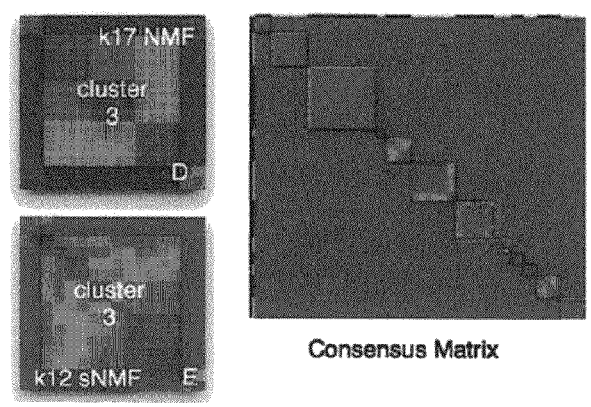
Consensus Matrix

Model Selection

Consensus Matrix

Consensus Matrix

Consensus Matrix

Model Selection

Consensus Matrix

Consensus Matrix

Consensus Matrix

Model Selection

Consensus Matrix

Consensus Matrix

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: chemically synthesized; MSH1 primer
<220> FEATURE:
<221> NAME/KEY: misc_feature
<222> LOCATION: (1)..(20)

<400> SEQUENCE: 1
gagactgacg cgccccagcc                                                    20

<210> SEQ ID NO 2
<211> LENGTH: 22
<212> TYPE: DNA
<213> ORGANISM: Artificial Sequence
<220> FEATURE:
<223> OTHER INFORMATION: chemically synthesized; MSH1 primer
<220> FEATURE:
<221> NAME/KEY: misc_feature
<222> LOCATION: (1)..(22)

<400> SEQUENCE: 2
cgcctggtcc atgaaagtga cg                                                 22

<210> SEQ ID NO 3
<211> LENGTH: 25
<212> TYPE: DNA
<213> ORGANISM: Artificial Sequence
<220> FEATURE:
<223> OTHER INFORMATION: chemically synthesized; BMI1 primer
<220> FEATURE:
<221> NAME/KEY: misc_feature
<222> LOCATION: (1)..(25)

<400> SEQUENCE: 3
gagaccagca agtattgtcc ttttg                                              25

<210> SEQ ID NO 4
<211> LENGTH: 22
<212> TYPE: DNA
<213> ORGANISM: Artificial Sequence
<220> FEATURE:
<223> OTHER INFORMATION: chemically synthesized; BMI1 primer
<220> FEATURE:
```

```
<221> NAME/KEY: misc_feature
<222> LOCATION: (1)..(22)

<400> SEQUENCE: 4
cattgctgct gggcatcgta ag                                               22

<210> SEQ ID NO 5
<211> LENGTH: 24
<212> TYPE: DNA
<213> ORGANISM: Artificial Sequence
<220> FEATURE:
<223> OTHER INFORMATION: chemically synthesized; Nestin primer
<220> FEATURE:
<221> NAME/KEY: misc_feature
<222> LOCATION: (1)..(24)

<400> SEQUENCE: 5
ggcagcgttg gaacagaggt tgga                                             24

<210> SEQ ID NO 6
<211> LENGTH: 24
<212> TYPE: DNA
<213> ORGANISM: Artificial Sequence
<220> FEATURE:
<223> OTHER INFORMATION: chemically synthesized; Nestin primer
<220> FEATURE:
<221> NAME/KEY: misc_feature
<222> LOCATION: (1)..(24)

<400> SEQUENCE: 6
ctctaaactg gagtggtcag ggct                                             24

<210> SEQ ID NO 7
<211> LENGTH: 20
<212> TYPE: DNA
<213> ORGANISM: Artificial Sequence
<220> FEATURE:
<223> OTHER INFORMATION: chemically synthesized; Sox2 primer
<220> FEATURE:
<221> NAME/KEY: misc_feature
<222> LOCATION: (1)..(20)

<400> SEQUENCE: 7
tacctcttcc tcccactcca                                                  20

<210> SEQ ID NO 8
<211> LENGTH: 20
<212> TYPE: DNA
<213> ORGANISM: Artificial Sequence
<220> FEATURE:
<223> OTHER INFORMATION: chemically synthesized; Sox2 primer
<220> FEATURE:
<221> NAME/KEY: misc_feature
<222> LOCATION: (1)..(20)

<400> SEQUENCE: 8
actctcctct tttgcacccc                                                  20

<210> SEQ ID NO 9
<211> LENGTH: 21
<212> TYPE: DNA
<213> ORGANISM: Artificial Sequence
<220> FEATURE:
<223> OTHER INFORMATION: chemically synthesized; GAPDH primer
<220> FEATURE:
<221> NAME/KEY: misc_feature
<222> LOCATION: (1)..(21)

<400> SEQUENCE: 9
```

```
gaggcattgc tgatgatctt g                                              21

<210> SEQ ID NO 10
<211> LENGTH: 20
<212> TYPE: DNA
<213> ORGANISM: Artificial Sequence
<220> FEATURE:
<223> OTHER INFORMATION: chemically synthesized; GAPDH primer
<220> FEATURE:
<221> NAME/KEY: misc_feature
<222> LOCATION: (1)..(20)

<400> SEQUENCE: 10
agccacatcg ctcagaacac                                                20
```

US 8,442,772 B2

COMPOSITIONS AND METHODS FOR DEFINING CELLS

CROSS-REFERENCE TO RELATED APPLICATIONS

This application claims benefit of U.S. Provisional Application No. 61/236,124, filed Aug. 23, 2009, and U.S. Provisional Application No. 61/274,958, filed Aug. 24, 2009, both of which are hereby incorporated by reference in their entirety.

STATEMENT REGARDING FEDERALLY SPONSORED RESEARCH

This invention was made with government support under P20 GM075059-01 awarded by the NIH. The government has certain rights in the invention.

REFERENCE TO SEQUENCE LISTING

The Sequence Listing submitted Nov. 15, 2010 as a text file named "25576_2_8403_2010_11_15_AMD_AFD_Sequence_Listing_Text_File.txt," created on Sep. 29, 2010 and having a size of 2,764 bytes is hereby incorporated by reference pursuant to 37 C.F.R. §1.52(e)(5).

BACKGROUND OF INVENTION

Stem cells are defined as self-renewing cell populations that can differentiate into multiple distinct cell types. However, hundreds of different human cell lines from embryonic, fetal and adult sources have been called stem cells, even though they range from pluripotent cells—typified by embryonic stem cells, which are capable of virtually unlimited proliferation and differentiation—to adult stem cell lines, which can generate a far more limited repertoire of differentiated cell types. The rapid increase in reports of new sources of stem cells and their anticipated value to regenerative medicine (Muller et al. Nature Rev Neurosci 7:75-84, 2006; Murry et al. Cell 132:661-680, 2008) has highlighted the need for a general, reproducible method for classification of these cells (Adewumi et al. Nature Biotech. 25:803-816, 2007). The creation and analysis of a database of global gene expression profiles ('stem cell matrix') enables the classification of cultured human stem cells in the context of a wide variety of pluripotent, multipotent and differentiated cell types. Using an unsupervised clustering method (Brunet et al. PNAS 101: 4164-4169, 2004; Gao et al. Bioinformatics 21:3970-3975, 2005) to categorize a collection of ~150 cell samples, pluripotent stem cell lines were discovered to group together, whereas other cell types, including brain-derived neural stem cell lines, are very diverse. Using further bioinformatic analysis (Ulitsky et al. BMC Syst Biol 1:8, 2007) a protein-protein network (PluriNet) was uncovered that is shared by the pluripotent cells (embryonic stem cells, embryonal carcinomas and induced pluripotent cells). Analysis of published data showed that the PluriNet seems to be a common characteristic of pluripotent cells, including mouse embryonic stem and induced pluripotent cells and human oocytes. This analysis provides a new strategy for classifying stem cells and supports the idea that pluripotency and self-renewal are under tight control by specific molecular networks.

BRIEF DESCRIPTION OF DRAWINGS

The patent or application file contains at least one drawing executed in color. Copies of this patent or patent application publication with color drawing(s) will be provided by the Office upon request and payment of the necessary fee

Interactive TreeMaps visualizing this and the results of the Stem Cell Matrix core and test datasets can be found online at www.stemcellmatrix.

Figure 4A:
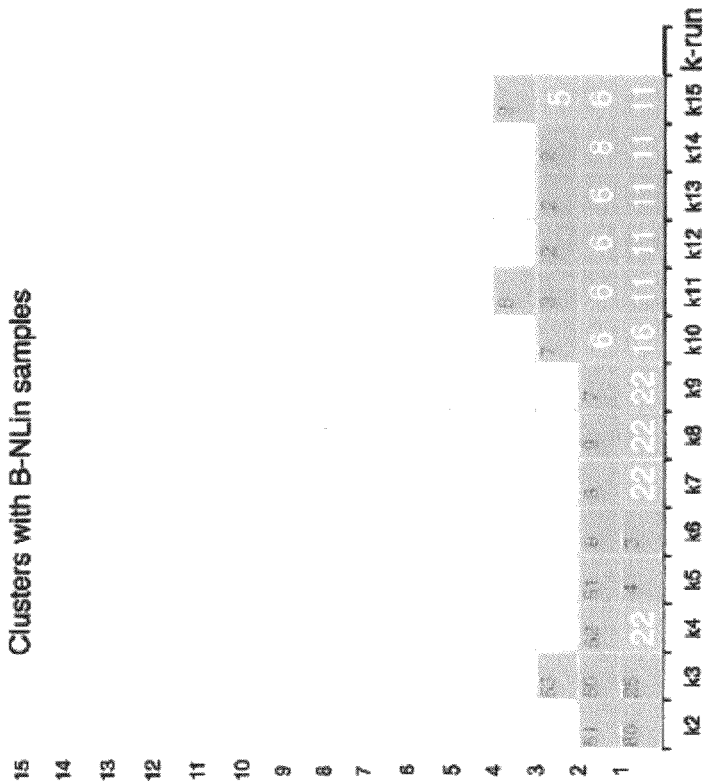
Figure 4B:
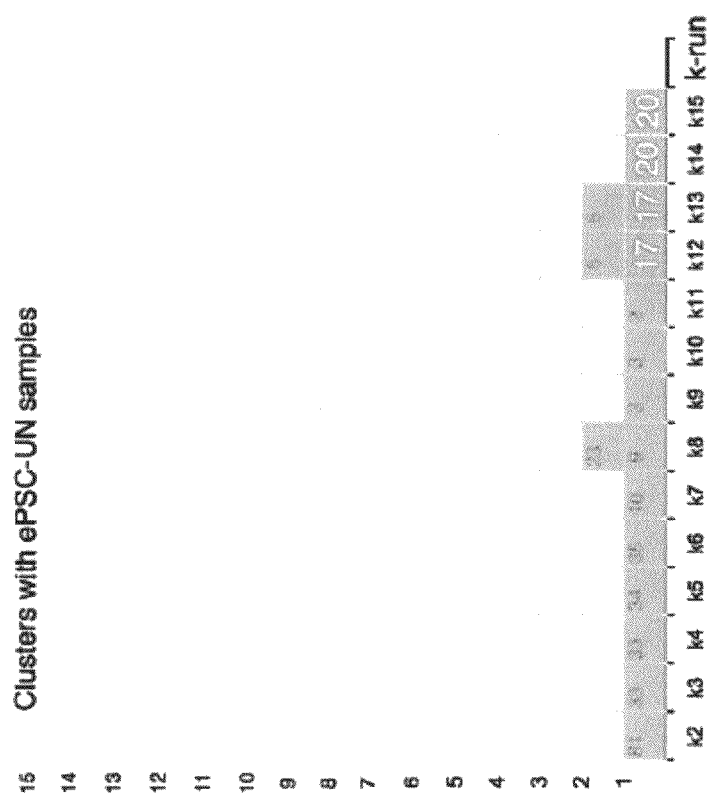
Figure 4C:
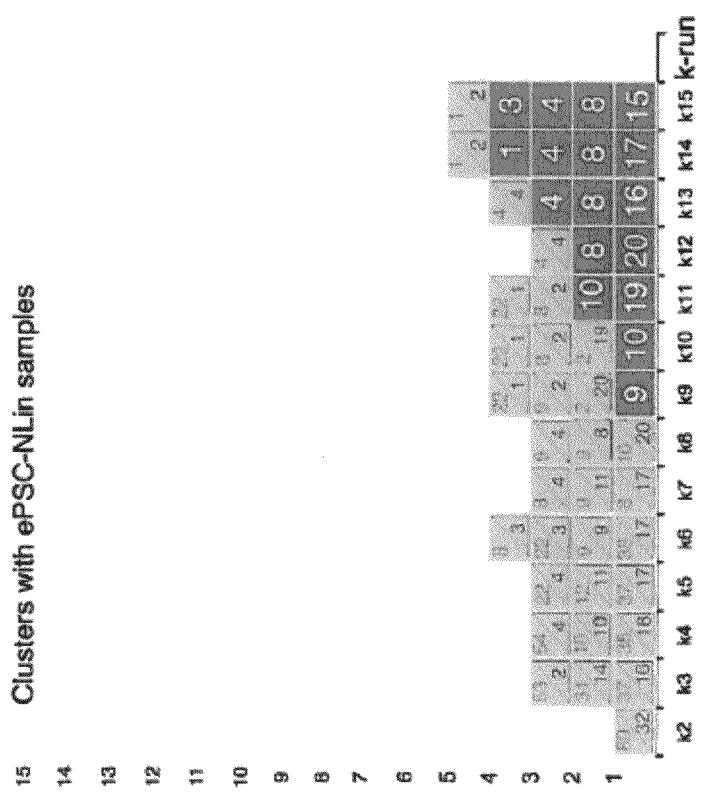

FIG. 4 shows the distribution of cell samples at different k values. The distribution of four input cell types (Source Codes: B-NLin, ePSC-UN, ePSC-NLin, and B-NLin-HANSE) is shown for each k-run (k=2-15). In each diagram, all of the possible clusters are indicated by squares. Clear squares indicate clusters that contain none of the designated samples. Grey squares containing numbers are mixed populations of the designated cell type (colored numbers) and other samples (grey numbers). Colored squares (colored according to input sample type as in FIG. 1) and white numbers in the squares indicate the number of designated samples that are in that cluster. A. Brain-derived neural lineage samples (25) were distributed into multiple clusters at all k-values. B. In contrast, undifferentiated embryonic pluripotent stem cell samples (ePSC; 20) were distributed into only one or two clusters. C. Samples designated as neural derivatives of ePSC fell into multiple clusters, even at the lowest k-values. D. The cell lines derived from surgical specimens (HANSE cells) were distributed into only one or two clusters at all k-values.

Figure 5C:
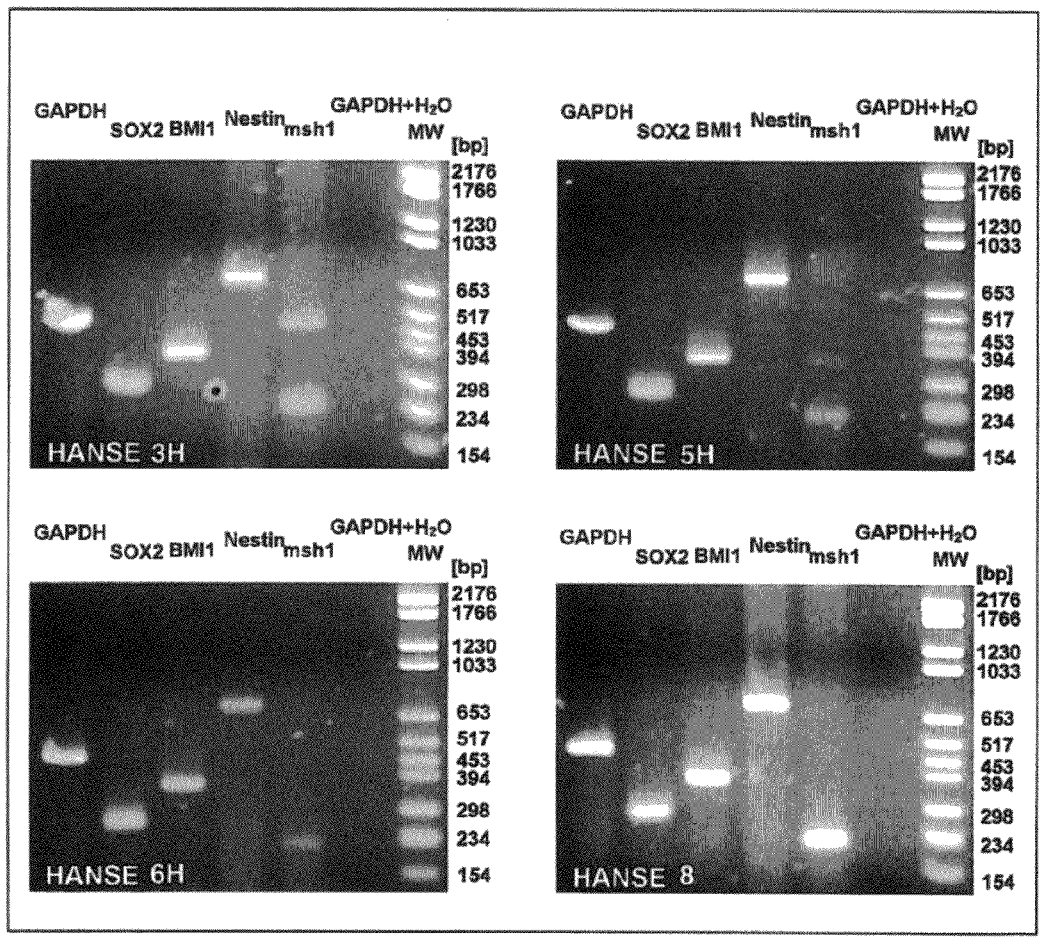

FIG. 5 displays properties of HANSE cells that have been assigned to other in vitro neural progenitor preparations. Cell suspensions of human adult brain parenchyma derived from surgical specimens were cultured under conditions reported to support the growth of neural stem cells. Within a few weeks, the cells formed morphologically homogenous adherent cell populations. Depending on the culture conditions, the resulting human adult neural progenitor cultures (HANSEs) could be extensively expanded as adherent monolayers (A. HANSE 5 h, passage 6; bar: 200 pm), or "neurospheres" (B. HANSE 8, passage 6; bar: 100 pm). C. mRNA expression of traditional stem cell markers such as SOX2, BMI1 NESTIN and MUSHASHI1 was confirmed by RT-PCR (representative data from HANSE cultures).

Figures 6A, 6B:
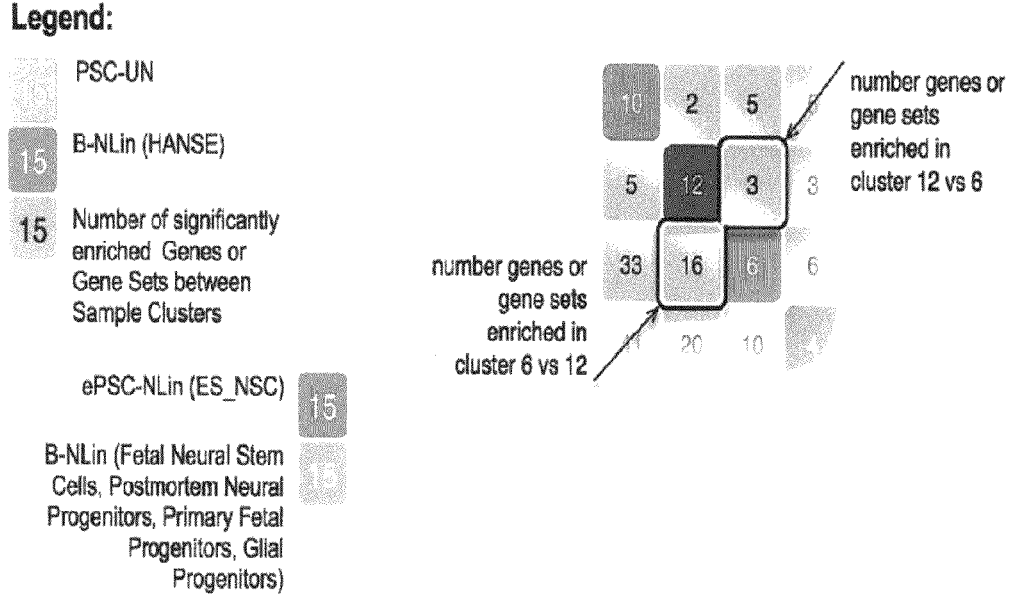

FIG. 6 illustrates pair-wise single gene and gene set analysis matrices. In order to elucidate, what the differences detected by NMF mean on the single gene as well as gene set level, each was compared with each cluster. Three methods were employed: (A) comparison of the differentially regulated genes between clusters with Student's t-test and used an FDR of ≦5% as cut-off point, (B) comparison of the gene set enrichment for 2700 genesets from public databases by means of the GSA method reported by Ephron and Tibshirani 2007 (FDR ≦10%) (Subramanian et al. PNAS 102:15545-50, 2005; Efron et al. The Annals of Applied Statistics 1:107-129, 2007.

For the identification of each cluster, n was plotted in the double column of squares on the left, each horizontal pair of squares represents a cluster; the cluster number is in the left-hand square and the number of samples in that cluster is given in the right-hand square of each pair. The color code relates to the Source Code (see also FIG. 2, Table 1-8, and FIG. 3) for types of input samples in each cluster. The legend gives the color code for each sample type. The cluster order and numbering from the k12 NMF results were used (see FIG. 1).

Figure 1:
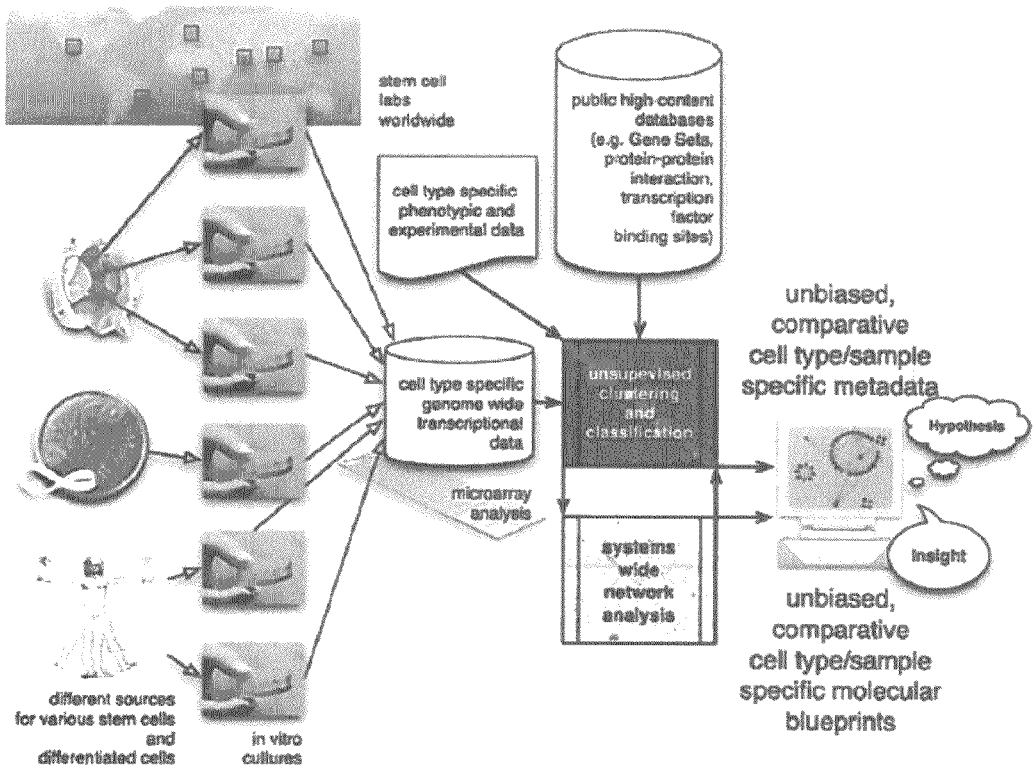
FIG. 1 is a schematic diagram of the sample collection and analysis for the stem cell matrix. Cell preparations for the stem cell matrix are cultured in the authors' laboratories or collected from other sources worldwide. Samples are assigned source codes that capture their biological origin and a relatively unbiased description of the cell type (such as BNLin for brain-derived neural lineage). Samples are collected and processed at a central laboratory for microarray analysis on a single Illumina BeadStation instrument. The genomics data are processed by unsupervised algorithms that are capable of grouping the samples based on non-obvious expression patterns encoded in transcriptional phenotypes. For pathway discovery, existing high-content databases with experimental data (for example, protein-protein interaction data or gene sets) are combined with the transcriptional database, a priori assumed identity of cell types and bootstrapped sparse non-negative matrix factorization (sample clustering) to produce metadata that can be mined with GSA software and topology-based gene set discovery methods (systems-wide network analysis). Web-based, computer-aided visualization methodologies can be used to formulate testable hypotheses and generate results and insights in stem cell biology. Two exemplary results are the classification of novel stem cell types in the context of other better understood stem cell preparations, and a molecular map of interacting proteins that appear to function together in pluripotent stem cells.

On the right, each matrix of squares is a representation of the consensus matrix shown in FIG. 1, and the diagonal line of squares contain the cluster numbers and the Source Code color code. The numbers in the rest of the diagram are the number of Genes or Gene Sets that were significantly different between pairs of clusters. See the legend for illustrations of the use of the matrix. See Table 11 for exemplary Gene Sets that differ between some of the pairs of clusters.

For the purpose of demonstrating the differences detected, the numbers of differentially regulated genes (A) or gene sets (B) are reported at the intersections between the clusters which are plotted on the diagonally from the upper left to the lower right corner.

Figure 7A:

FIG. 7 represents a pluripotent stem-cell-specific protein-protein interaction network detected by MATISSE. Clusters from the sNMF k=12 analysis were used in combination with the transcriptional database to identify protein-protein interaction networks enhanced in PSCs. A, A large differentially expressed connected subnetwork (PluriNet) shows the dominance of cell cycle regulatory networks in PSCs (see legend). All of the dark blue symbols are genes that are highly expressed in most PSCs compared to the other cell samples in the data set. Front nodes, as represented by stem cell matrix expression data, and back nodes, as inferred by MATISSE, are displayed with different color shades. Highlighted in red are the interactions of a group of proteins associated with pluripotency in murine ePSCs. This subnetwork shows a significant enrichment in genes that are targeted in the genome by the transcription factors NANOG (P=5.88×10$^{-4}$), SOX2 (P=0.058) and E2F (P=1.29×10$^{-16}$, all P-values are Bonferroni corrected). For an interactive visualization of PluriNet, see http://www.stemcellmatrix.org. B, illustrates the expression patterns of PluriNet in somatic and pluripotent cells. Heat map-like visualization of Plurinet genes for selected samples from the test dataset. Probes representing the 299 PluriNet genes were extracted from the quantile-normalized Stem Cell Matrix Core and Test Data Set, log 2-transformed for variance stabilization and gene-wise ("row-") normalized over all 219 samples. The expression values were mapped onto the PluriNet-PPI network and selected samples visualized. HUVECs (UC-EC, a-c, derived from three independent individuals), germ cell tumor-derived pluripotent stem cells (tPSC-UN, d-f, lines GCT-C4, GCT-72, GCT-27X, derived from three independent individuals) (Pera et al. Int J. Cancer 40:334-43, 1987; Para et al. Differentiation 42:10-23, 1989), induced pluripotent stem cells (iPSC-UN, g-i, BJ1-iPS12, MSC-iPS1, hFib2-iPS5, three independently derived lines from different somatic sources) and embryonic stem cells (ePSC-UN, j-l, lines Hues22, HSF6, ES2, derived from three independent blastocysts in three independent laboratories). Most PluriNet genes are markedly upregulated in iPSC-UN and ePSC-UN cells. tPSC-UN cells show a less consistent expression pattern. UC-EC cells show lower expression levels of most PluriNet genes. C, Analysis of genes from PluriNet in the context of phenotypes that have been reported to result from specific genetic manipulations (for example, gene knockout) in mice in the MGI 3.6 phenotype ontology database (http://www.informatics.jax.org/). There are significant over-representation of phenotypes 'lethality (perinatal/embryonic)', 'tumorigenesis', 'cellular', 'embryogenesis', 'reproductive system' and 'lifespan and ageing' among the genes in PluriNet. Although these broad categories might be rather unspecific surrogate markers for PSC function in mammals, this analysis might point towards PluriNet's role in vivo. For more details, see also FIG. 8A.

Figure 7B:
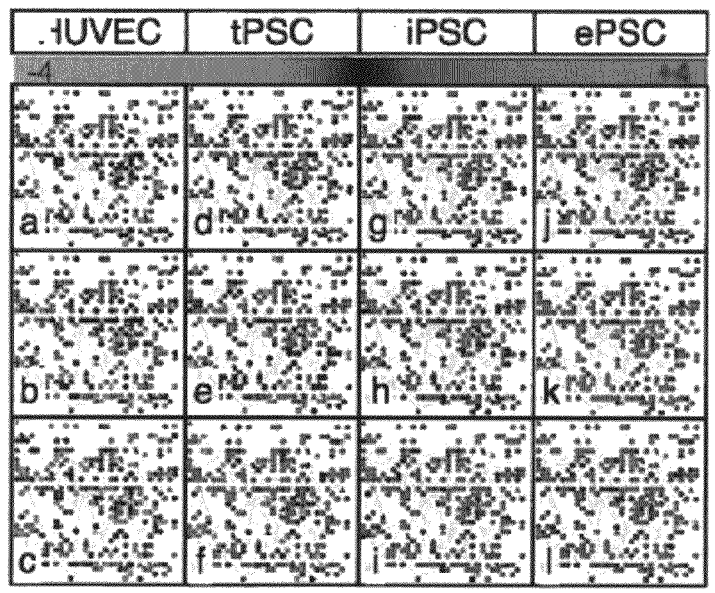
Figure 8A:
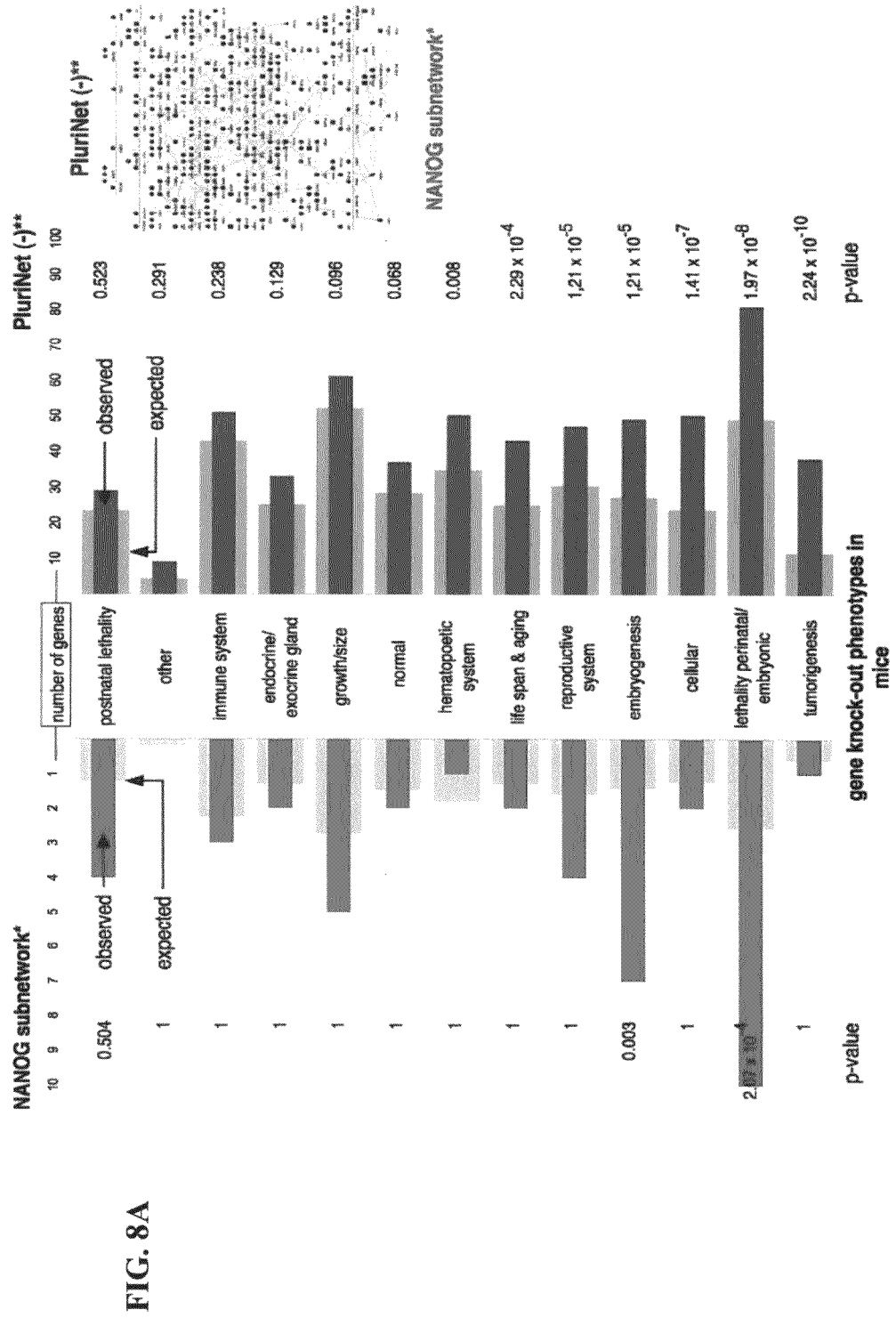

FIG. 7B illustrates the expression patterns of PluriNet in somatic and pluripotent cells. Heat map-like visualization of PluriNet genes for selected samples from the test dataset. Probes representing the 299 PluriNet genes were extracted from the quantile-normalized Stem Cell Matrix Core and Test Data Set, log 2-transformed for variance stabilization and gene-wise ("row-") normalized over all 219 samples. The expression values were mapped onto the PluriNet-PPI network and selected samples visualized. HUVEC (UC-EC, derived from three independent individuals), germ cell tumor derived pluripotent stem cells (tPSC-UN, lines GCT-C4, GCT-72, GCT-27X, derived from three independent individuals (Pera et al. Int J Cancer 40:334-43, 1987; Pera et al. Differentiation 42:10-23, 1989), induced pluripotent stem cells (iPSC-UN, BJ1-iPS12, MSC-iPS1, hFib2-iPS5, three independently derived lines from different somatic sources) and embryonic stem cells (ePSC-UN, lines Hues22, HSF6, ES2, derived from three independent embryos in three independent labs[47-51]).

Most PluriNet genes are markedly up-regulated in iPSC-UN and ePSC-UN. tPSC-UN do show a less consistent expression pattern. UC-EC show lower expression levels of most PluriNet genes.

Figure 7C:
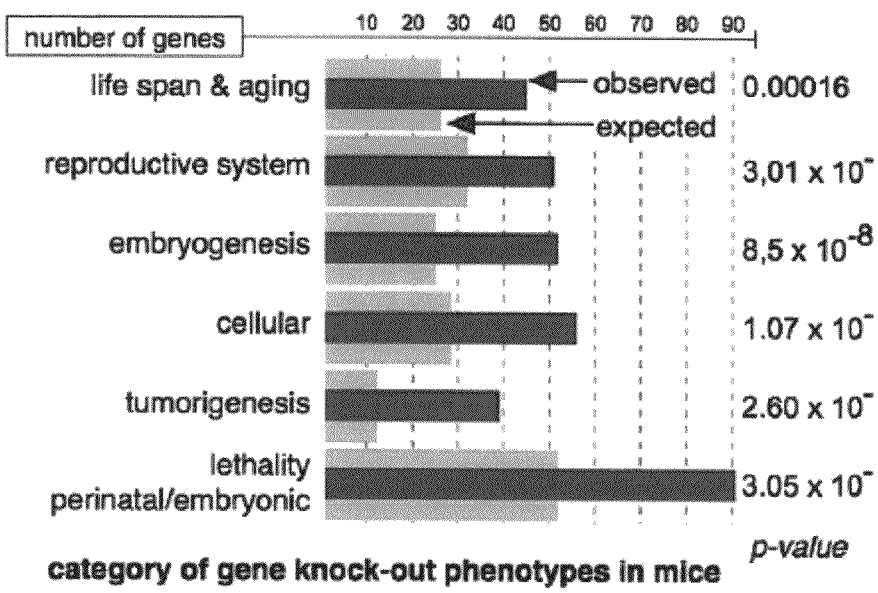
Figure 8B:
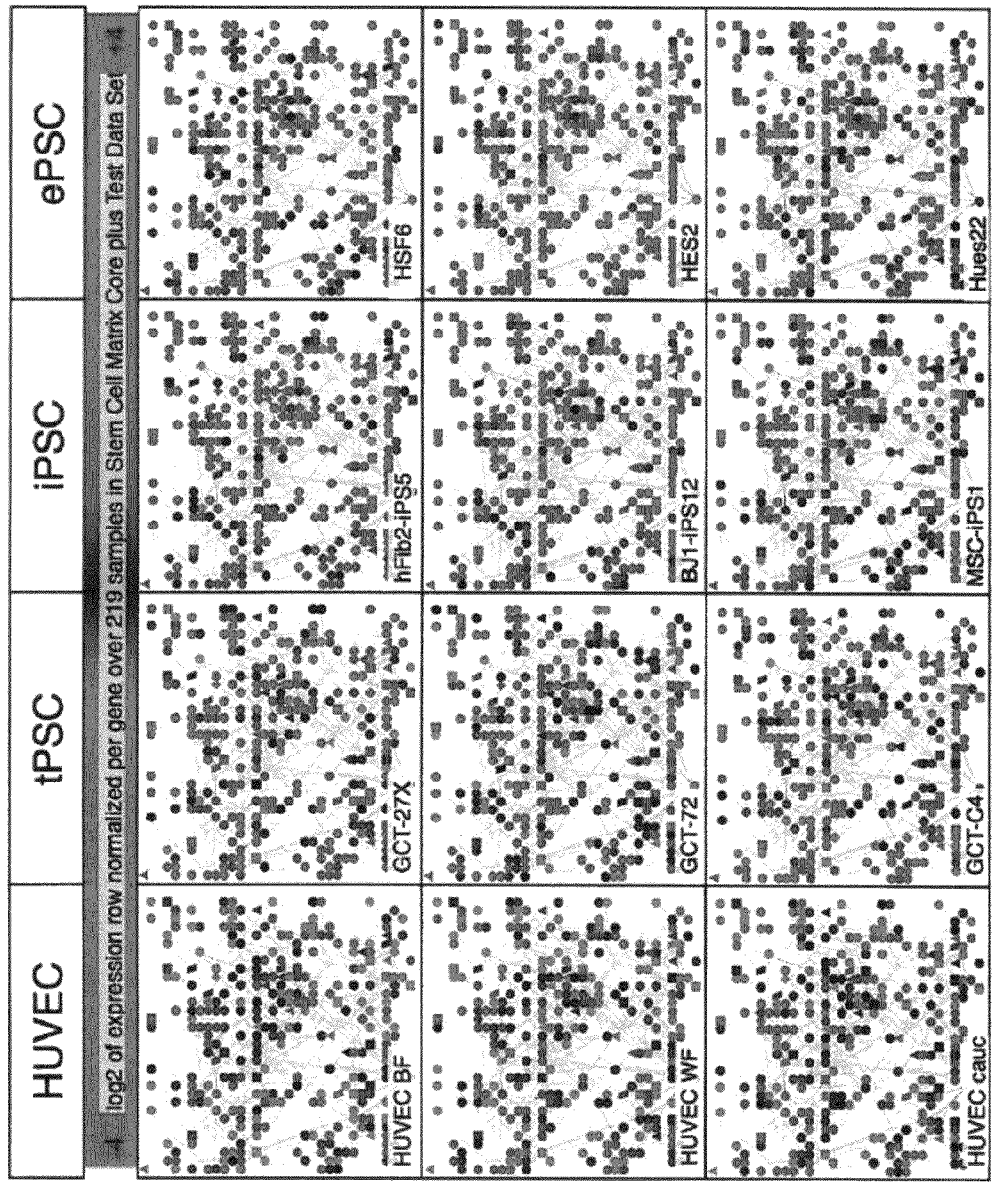
Figure 10A:
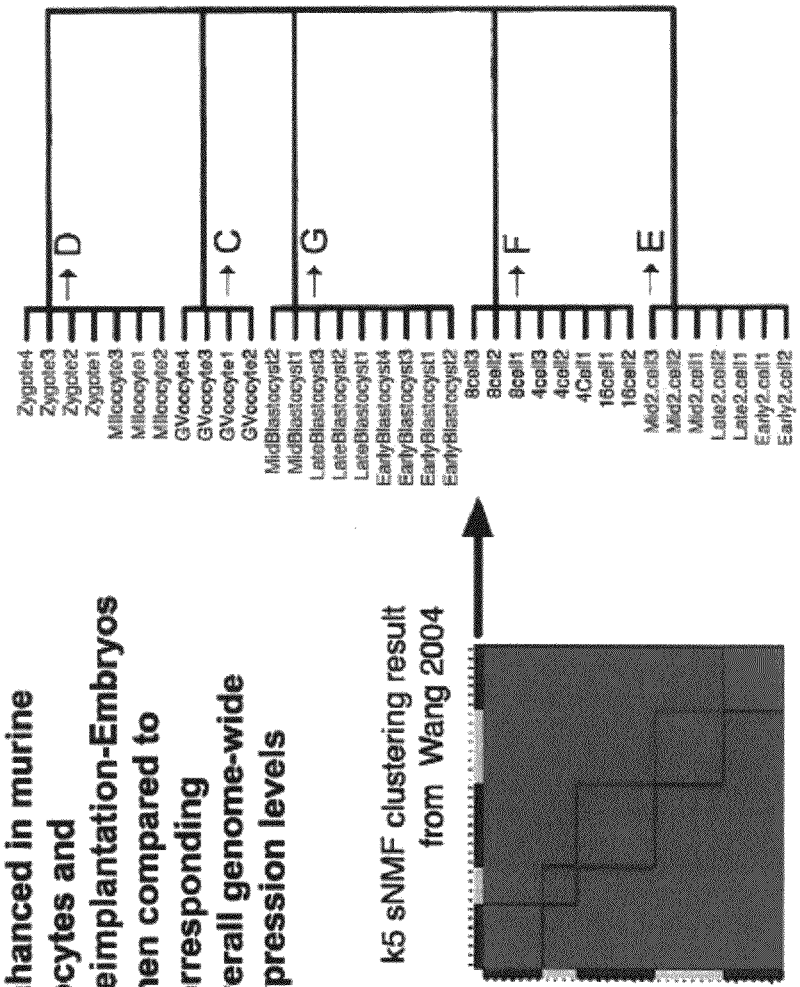
Figure 10B:
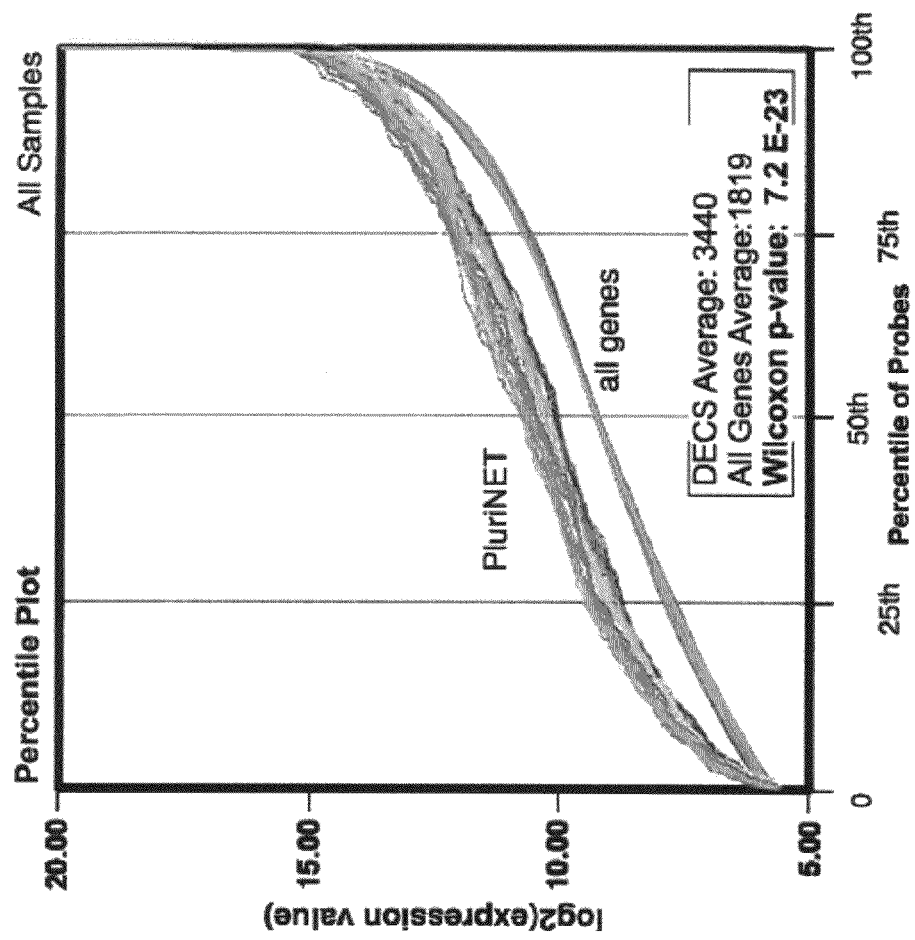
Figures 10C, 10D, 10E:
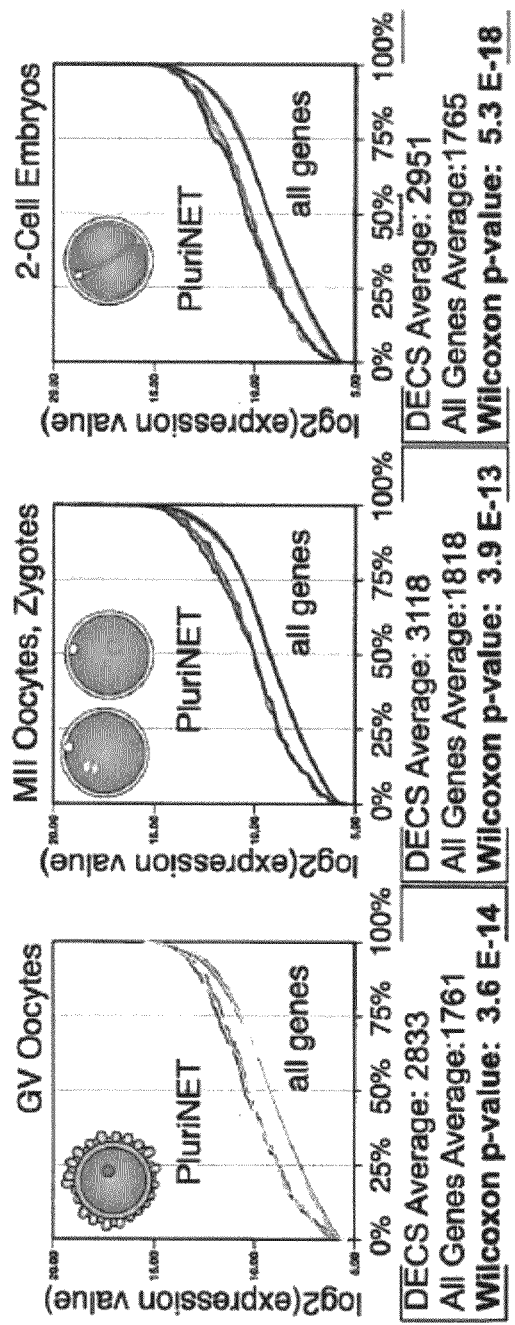
Figures 10F, 10G:
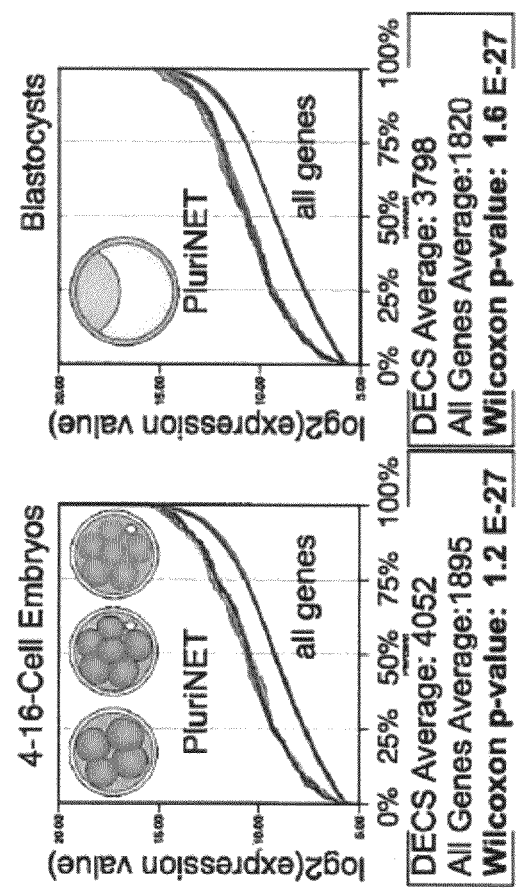
Figure 10G:
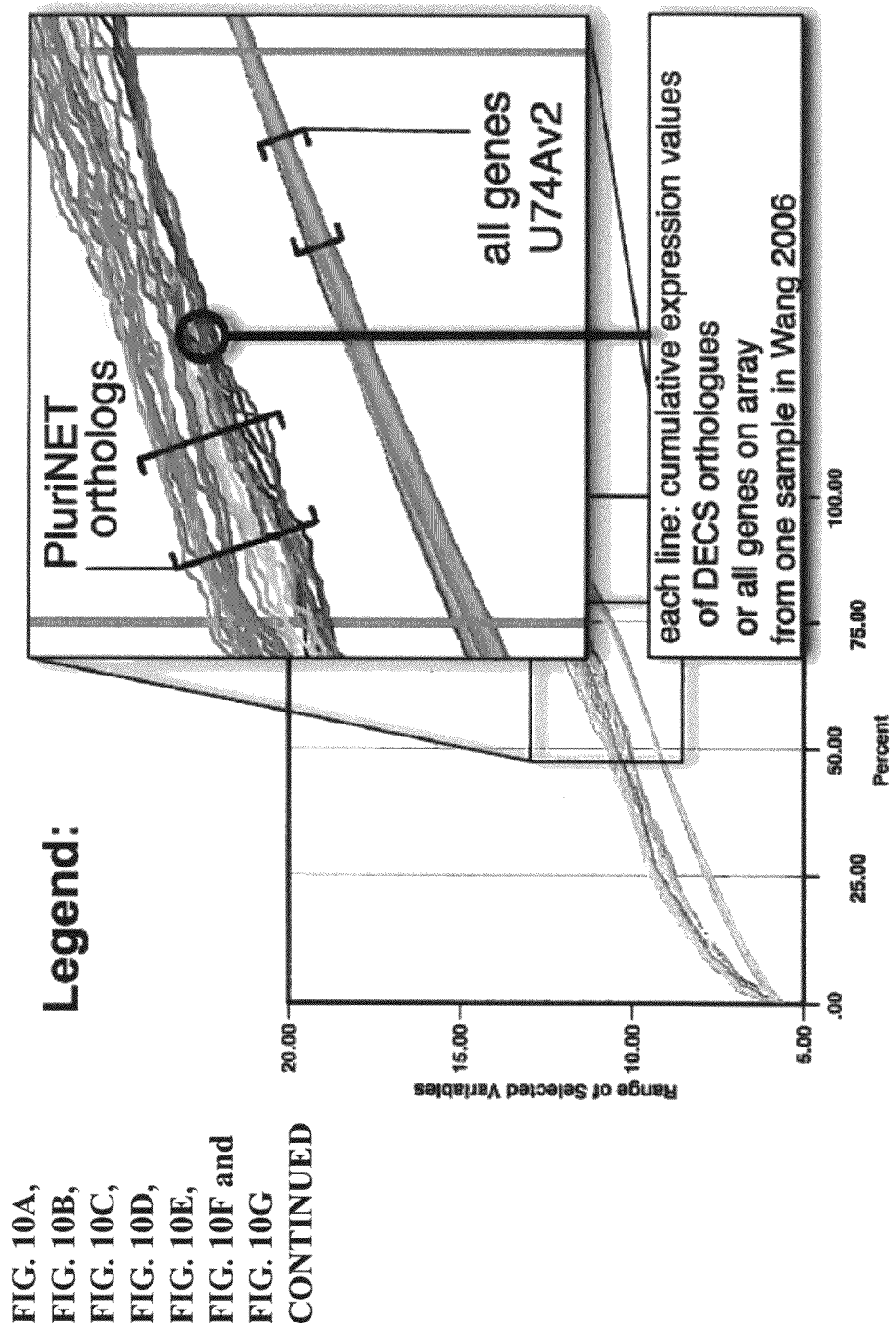

FIG. 8 illustrates that specific phenotypes that have been observed in genetically engineered mice are significantly linked to genes that are part of PluriNet. All available genotypes and annotations were retrieved from the Mouse Genome Informatics website (http://www.informatics.jax.org/, MGI 3.6) and searched for mammalian phenotype ontology categories, which were overrepresented in PluriNet (25,999 genotypes and 113,717 annotations as accessed on 22 Jan. 2008; see also FIG. 7C) (Eppig et al. Nucleic Acids Res 33:D471-5, 2005). Genes that had been previously described as components of a pluripotency-associated protein-protein network in murine PSC (Wang et al. Nature 444:364-8, 2006) (*; NANOG subnetwork, marked red) were differentiated from the remaining genes in PluriNet (**; PluriNet, marked blue, see also small network inset) in order to control for the possibility that this subnetwork can be the driving force for phenotypical over-representations in PluriNet. All p-values were Bonferroni corrected for multiple testing.

There were striking overrepresentations of ontological terms "tumorigenesis", "lethality (perinatal/embryonic)", "cellular", "embryogenesis", "reproductive system", "life span and aging" in the larger PluriNet context.

It is important to note that the ontological terms in the Mammalian Phenotype Ontology (Eppig et al. Nucleic Acids Res 33:D471-5, 2005) can represent broad, rather unspecific and possibly imprecise surrogate measures for mammalian PSC function in vivo. Yet the presence and increased expression of the PluriNet genes in human and murine PSC from different sources, in combination with the strong statistical connection between genetically modifying the genes' function and resulting phenotypes, suggest mechanistic links between PluriNet and stem cell functions in vivo.

FIG. 9 demonstrates that the PluriNet is up-regulated in human M11 Oocytes. Microarray datasets from human M11 Oocytes (Kocabas et al. PNAS 103:14027-32, 2006; Wood et al. J Clin Endorcrinol Metab 92:705-13, 2007) was accessed on the authors' or the journals' website respectively (http://www.crl.msu.edu/Supp WEB/Kocabas et al. Supp. Web Index.htm, http://jcem.endojournals.org/cgi/content/full/jc.2006-2123/DC1).

Panels A-D demonstrate by various means a significant presence of nearly all genes from PluriNet in the transcriptome of human oocytes, as well as a significant and marked up-regulation of most of these genes in these cells as compared to somatic tissues and cell types.

Panel A shows a heatmap of differentially regulated genes in normal human oocytes as compared to somatic tissues (Kocabas et al. PNAS 103:14027-32, 2006). The same data (Kocabas et al. PNAS 103:14027-32, 2006) as well as genes that were detected to be expressed but not differentially expressed are mapped onto the PluriNet in Panel B. Panel C displays the same view with genes that were detected to expressed in human oocytes from healthy women and patients with polycystic ovary syndrome. This study confirms largely the findings of the first dataset. In Panel C the "presence" calls is plotted as suggested by Wood and colleagues, but there is no computing up- and down-regulation of these genes, due to significant technical differences and lack of a sufficient number of microarray replicates (Wood et al. J clin Endocrinol Metab 92:705-13, 2007; R Development Core Team, R: A Language and Environment for Statistical Computing, help files 2007).

Panel D shows by means of Gen Set Enrichment Analysis that PluriNet is significantly up-regulated in oocytes as compared to somatic cell types in the dataset from Kocabas et al. 2006 (Subramanian et al. PNAS 102:15545-50, 2005; Kocabas et al. PNAS 103:14027-32, 2006). For this specific case gene set permutation was performed because the number of samples in each class were <7. With small datasets, there might not be enough random permutations of sample labels to generate a sufficient null distribution. In such cases, gene set randomization is a better choice (Subramanian et al. PNAS 102:15545-50, 2005).

FIG. 10 demonstrates that the PluriNet is significantly enhanced in murine oocytes and preimplantation-embryos compared to corresponding overall genome-wide expression levels. The Affymetrix microarray U74Av2 cell files were downloaded from Wang et al. (Wang et al. Dev Cell 6:133-44, 2004) and preprocessed the data (E-MEXP-51 at www.ebi.ac.uk/arravexpress; see also the Methods section). The dataset was subjected to sNMF consensus clustering for an unsupervised grouping of the samples. The k=5 result with the best cophenetic correlation coefficient was chosen because it provided us with an reasonable grouping of developmental stages and sufficient numbers of biological replicates for a statistically sound downstream analysis (A). When all of the arrays' probe intensities are compared with the subset (276 probes on U74Av2 that represent orthologs of genes from PluriNet and which can be matched with EMBL Biomart; http://www.biomart.org), PluriNet orthologs are expressed at significantly higher levels when compared to the whole transcriptome (each colored line in B-G represents either the cumulative expression values of PluriNet-orthologs or all genes represented on U74Av2 arrays for each sample from Wang 2004 (Wang et al. Dev Cell 6:133-44, 2004)). In every instance the orthologs' expression levels were higher than all other genes. There is also a trend towards increasing transcriptional levels as development progresses (C-G). The differences, when compared to the enrichment for PluriNet orthologs as gene set between sNMF sample clusters, are significant at an FDR >10% and a p-value <0.01 when the blastocyst or 4-16 cell stages are compared with GV oocytes or MII oocytes/zygotes by means of GSEA (Subramanian et al. PNAS 102:15545-50, 2005) (analysis not shown).

Figure 11A:
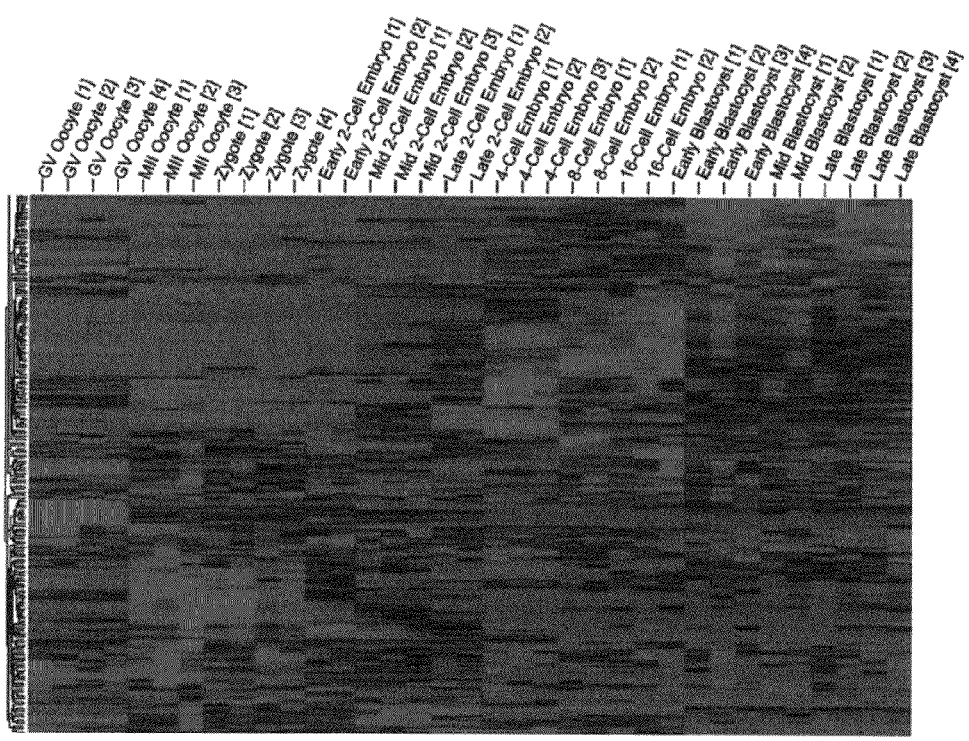
Figure 11B:
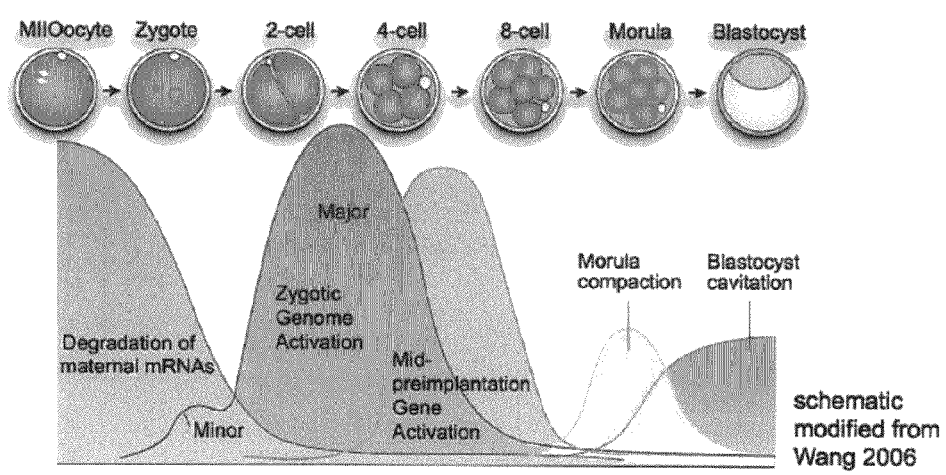

FIG. 11 shows that distinct patterns of expression of the PluriNet are found at sequential stages of murine oogenesis and preimplantation development. Although the whole transcriptome undergoes tremendous changes during development (see B, adapted from Wang 2006 (Wang et al. Nat Rev Genet. 7:185-99, 2006)), PluriNet is maintained at relatively high transcriptional levels throughout this process. The relative expression of PluriNet members was analyzed to determine whether the components changed with respect to each other during embryonic development. When the 276 orthologs of PluriNet genes in the dataset (Wang et al. Dev Cell 6:133-44, 2004) were analyzed in relationship to each other, distinctive expression patterns within PluriNet appeared (for more details see also FIG. 12 Significant and lasting transitions through development among the murine orthologs of PluriNet were found (A). This can mean that the protein-protein interaction networks require relative changes in the levels of individual components for adaptive functioning during oogenesis and early embryonic development.

Figure 12:
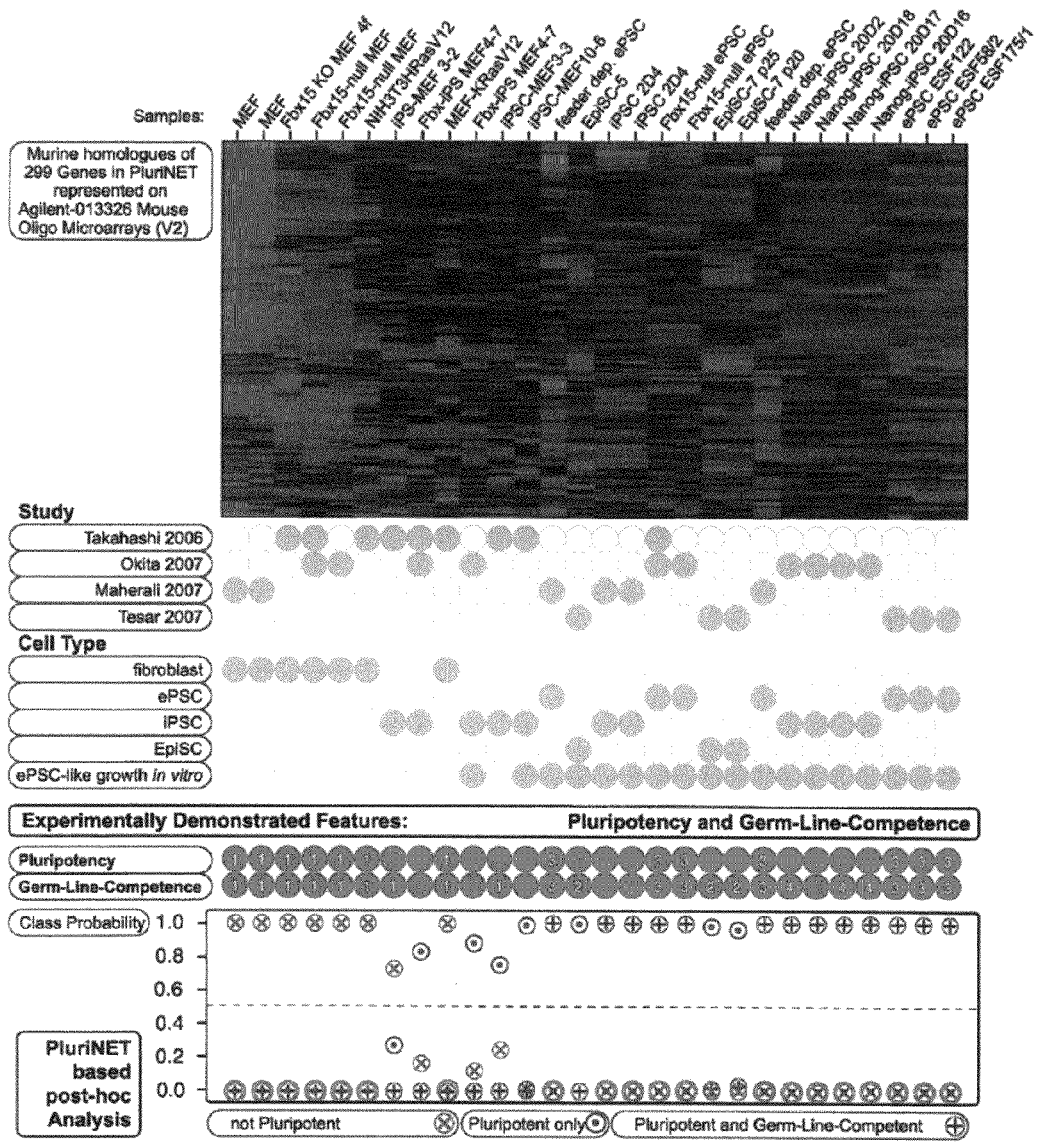
Figure 12:

FIG. 12 illustrates that the PluriNet is differentially expressed in murine Fibroblasts, Epiblast-derived Stem Cells, induced Pluripotent Stem Cells and murine Embryonic Pluripotent Stem Cells. Datasets from four different, recently published studies (Tesar et al. Nature 448:196-9, 2007; Okita et al. Nature, 2007; Maherali et al. Cell Stem Cell 1:55-70, 2007; Takahashi et al. Cell 126:663-76, 2006) were downloaded from NCBI GEO (http://www.ncbi.nlm.nih.gov/qeo/, DataSets GSE7902, GSE5259, GSE7815, GSE7841), assembled into one file, preprocessed and filtered for the murine homologues of the 299 human genes from the discovered PluriNet. The resulting genes and their expression values in each sample were subjected to the Prediction Analysis for Microarrays (PAM) algorithm by Tibshirani and colleagues (leave-one-out-cross-validation, categories: no pluripotence vs. pluripotence vs. germ-line-competence; class probabilities were re-computed 10 000 times; average scores are reported) (Lacayo et al. Blood 104:2646-54, 2004). Murine ePSC from blastocysts have been known for more than 25 years now, but only recently two groups have established protocols to derive Epiblast-derived Stem Cells (EpiSC) which can resemble human ePSC more than murine ePSC (Tesar et al. nature 448:196-9, 2007; Brons et al. Nature 448:191-5, 2007). Others have recently developed methods to reprogram fibroblasts into induced pluripotent stem cells (iPSC), which share in certain instances key similarities with murine ePSC, including pluripotence and germ line competence after blastocyst injection (Wernig et al. Nature, 2007; Maherali et al. Cell Stem Cell 1:55-70, 2007; Takahashi et al. Cell 126:663-76, 2006; Meissner et al. Nat Biotechnol, 2007). Features of each murine cell preparation were curated according to the published manuscripts or inferred from earlier publications of the same or similar cell preparations. The PluriNet could be useful as a post-hoc predictor for distinct features of pluripotent cells with only 2 samples out of 28 not categorized according to their experimentally verified features. This is remarkable, since the algorithms used for assembling the PluriNet were neither designed nor optimized for such a task and the differentially expressed connected subnetwork was discovered in a human system. Yet, retrospective re-analysis of published data points toward the fascinating possibility, that, in the future, unsupervised machine learning algorithms can construct reliable outcome predictions based on unbiased molecular and phenotypic stem cell models.

Figures 13A, 13B, 13C:
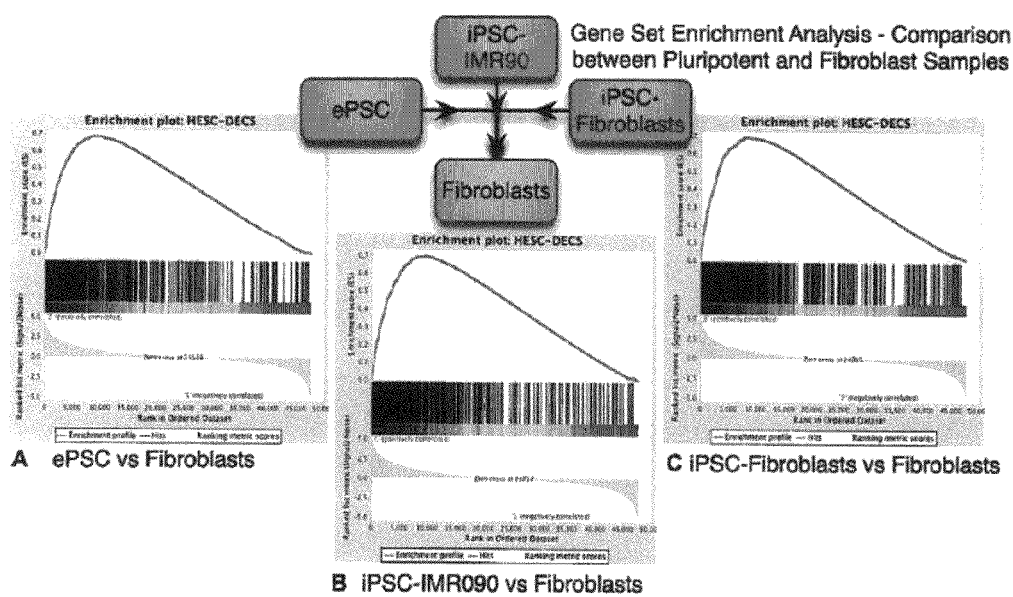
Figures 13D, 13E:
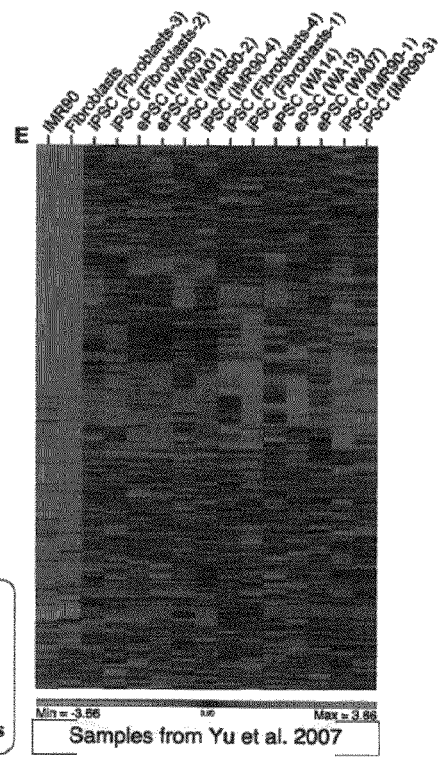

FIG. 13 illustrates that the PluriNet is differentially expressed in human Fibroblasts, ePSC and iPSC induced with LIN28, NANOG, OCT4 and SOX2. A microarray data-set from a recently published study (Yu et al. Science, 2007) was kindly provided by the authors (V. Ruotti, University of Wisconsin, personal communication) and analyzed by GSEA and heatmap inspection (Caraux et al. Bioinformatics 21:1280-1, 2005) of the 698 probes on custom Nimblegen *H. sapiens* hg 18-expression arrays (http://www.ncbi.nlm.nih.gov/geo/query/acc.cgi?acc=GPL5876; these probes represent 291 genes from PluriNet; all files used in this experiment are provided on the Supplementary Website).

Four independent groups have recently reported methods to reprogram human fibroblasts into induced Pluripotent Stem Cells (iPSC) (Yu et al. Science, 2007; Takahashi et al. Cell 131:861-72, 2007; Nakagawa et al. Nat Biotechnol, 2007; Takahashi et al. Nat Protocol 2:3081-9, 2007), which share properties with hESC, including in vitro pluripotence and teratoma formation after injection into immune-compromised mice. Only the microarray data-set from Thomson and colleagues[77] encompasses replicates of ePSC, iPSC and fibroblast preparations, thus enabling the rational application of bio-statistical methodologies (Allison et al. Nat Rev Genet 7:55-65, 2006). Yu et al. 2007 transfected fibroblasts with SOX2, NANOG, LIN28 and OCT4, which differs from the factor combinations used by Takahashi et al. (Takahashi et al. Cell 131:861-72, 2007) and Park et al. (Park et al. Nature 451:141-6, 2008).

The vast majority of transcripts from PluriNet are markedly up regulated in iPSC and ePSC when compared to the unmodified fibroblast cells (A, B, C). The high degree of statistical significance that can be associated with this enrichment by using standard methodologies (Subramanian et al. PNAS 102:15545-50, 2005) is remarkable (D, p-value, FDR and FWER <0.001 in all three cases). Inspection of a heatmap representation (E) (Caraux et al. Bioinformatics 21:1280-1, 2005) of the primary data reveals low expression levels of most of PluriNet transcripts in fibroblasts and consistent high levels in PSC, thus providing an intuitive explanation for the summary statistics results provided by GSEA.

This preliminary finding indicates that PluriNet network is significantly induced by different protocols in bio-engineered, human PSC.

Figure 14:
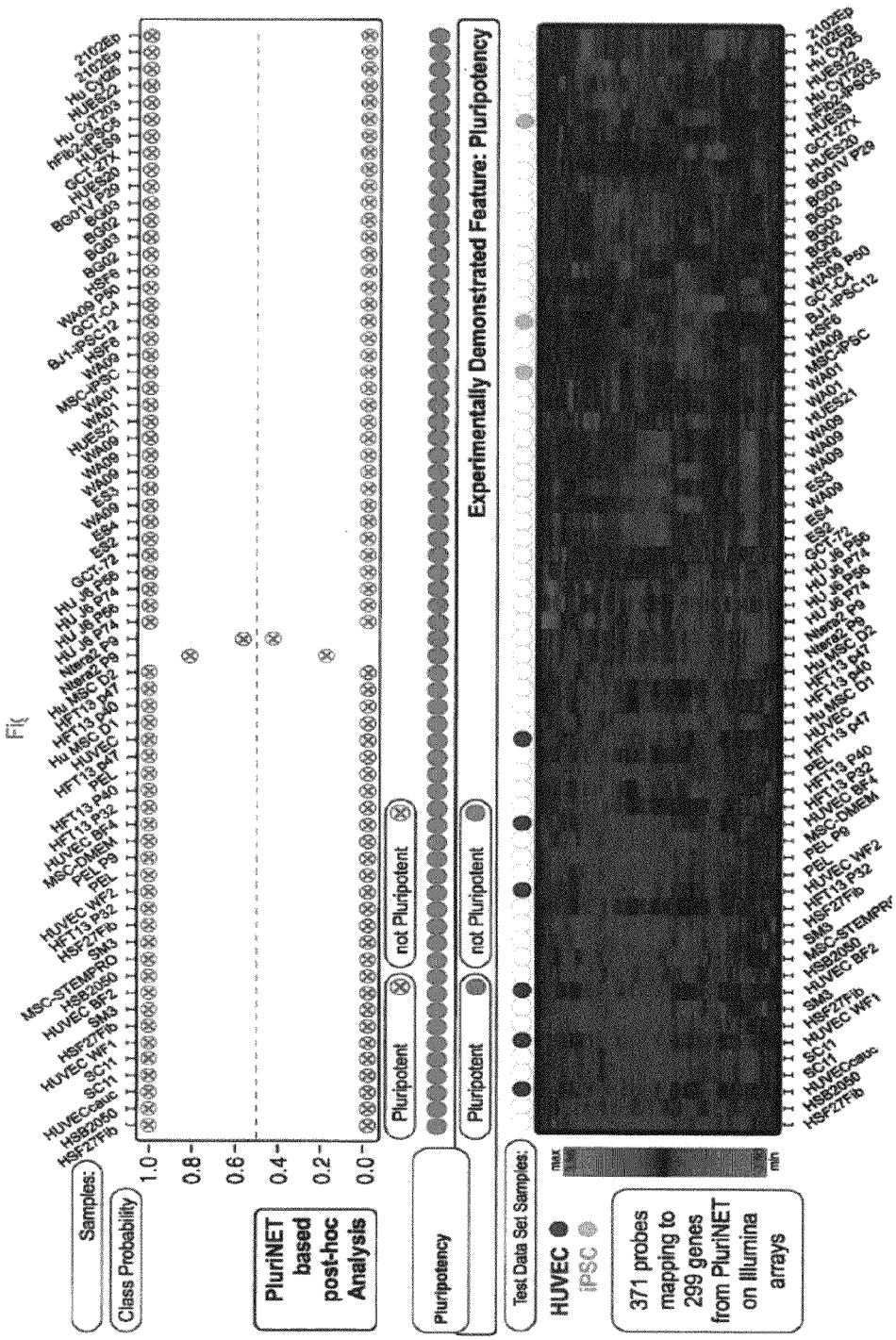

FIG. 14 shows that the PluriNet is differentially expressed in human somatic cell types, somatic stem cells, tumor-derived, pluripotent stems cells, embryonic pluripotent stem cells and induced pluripotent stem cells. The 371 probes on Illumina V1 expression arrays representing the 299 PluriNet genes (FIG. 2) from the Stem Cell Matrix (SCM) test dataset samples (see Table 7) were subjected to the Prediction Analysis for Microarrays (PAM) algorithm by Tibshirani and colleagues (leave-one-out-cross-validation, categories: no pluripotence vs. pluripotence, class probabilities were re-computed 10,000 times; average scores are reported) (Lacayo et al. Blood 104:2646-54, 2004).

Importantly, the samples from the test dataset were not part of the process that led to assembling PluriNet. Moreover, two "novel" sample categories were included, one somatic (HUVEC, Source Code EC-UN) and one presumably pluripotent cell type (induced pluripotent stem cells, Source Code: iPSC).

The results show that the expression pattern of PluriNet mirrors, in most cases, closely biological, experimentally verified features. An intuitive explanation of this finding is provided by heatmap inspection: PluriNet genes are regularly up-regulated in pluripotent cell types when compared to somatic in vitro preparations.

FIG. 15 shows Venn diagrams of Illumina probes from PluriNet and three studies that have screened for "essential" cell cycle genes or cyclic expressed genes during cell cycle progression.

FIG. 16 displays a set-to-set Leading Edge Analysis of human ePSC vs HeLa cells. (A) The color coded heat map indicates that the enrichment scores were not driven by genes that overlapped in between PluriNet and the cell cycle related gene sets that were analyzed between WA09 and HeLa samples. (B) Plotting the overlap score shows that there is only minimal leading edge signal (0.045) overlap between the Bar-Joseph G1/S common gene set and PluriNet but no overlap between PluriNet and any other gene set analyzed.

Figure 17:
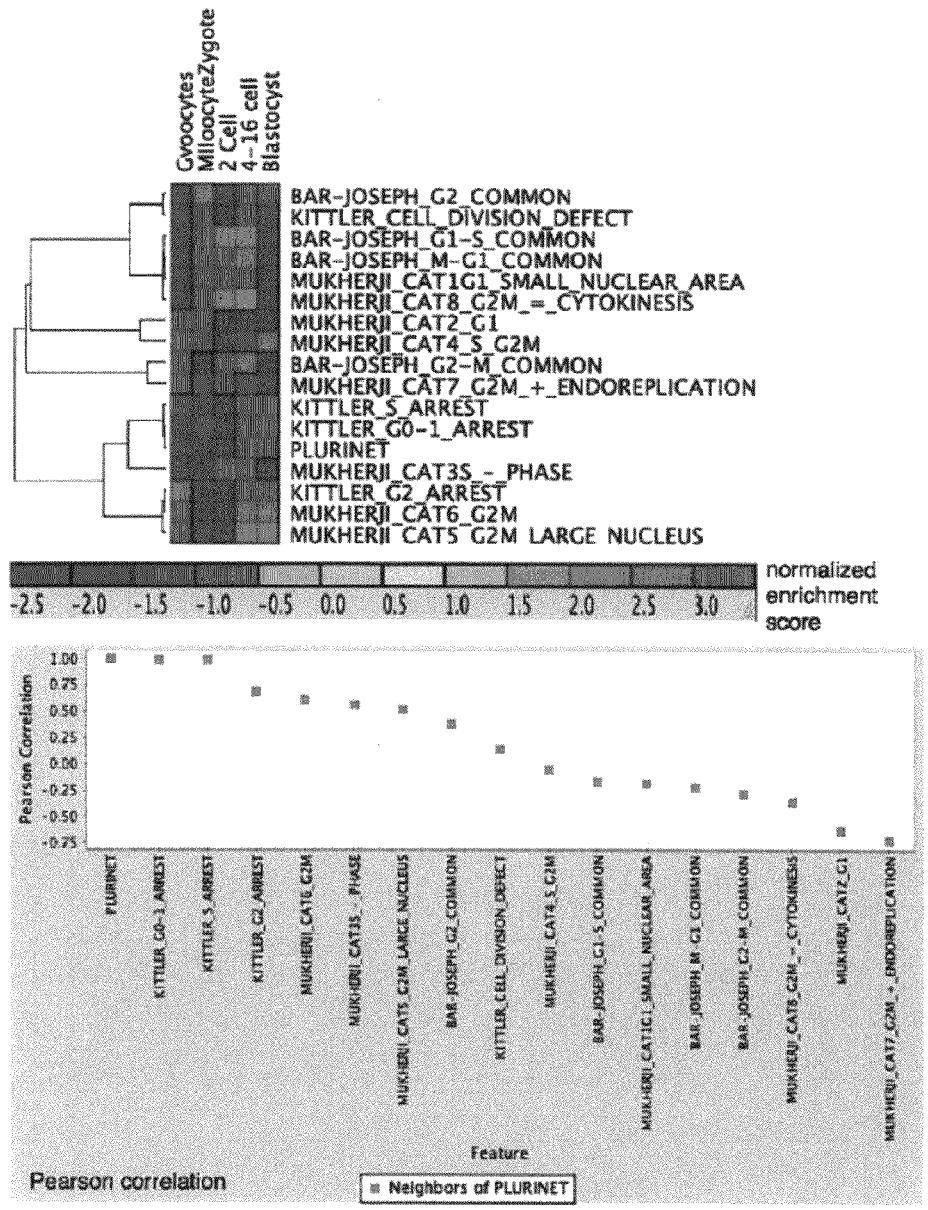

FIG. 17 shows the trends of cell cycle specific gene set and PluriNet expression during murine preimplantation development.

Figure 18:
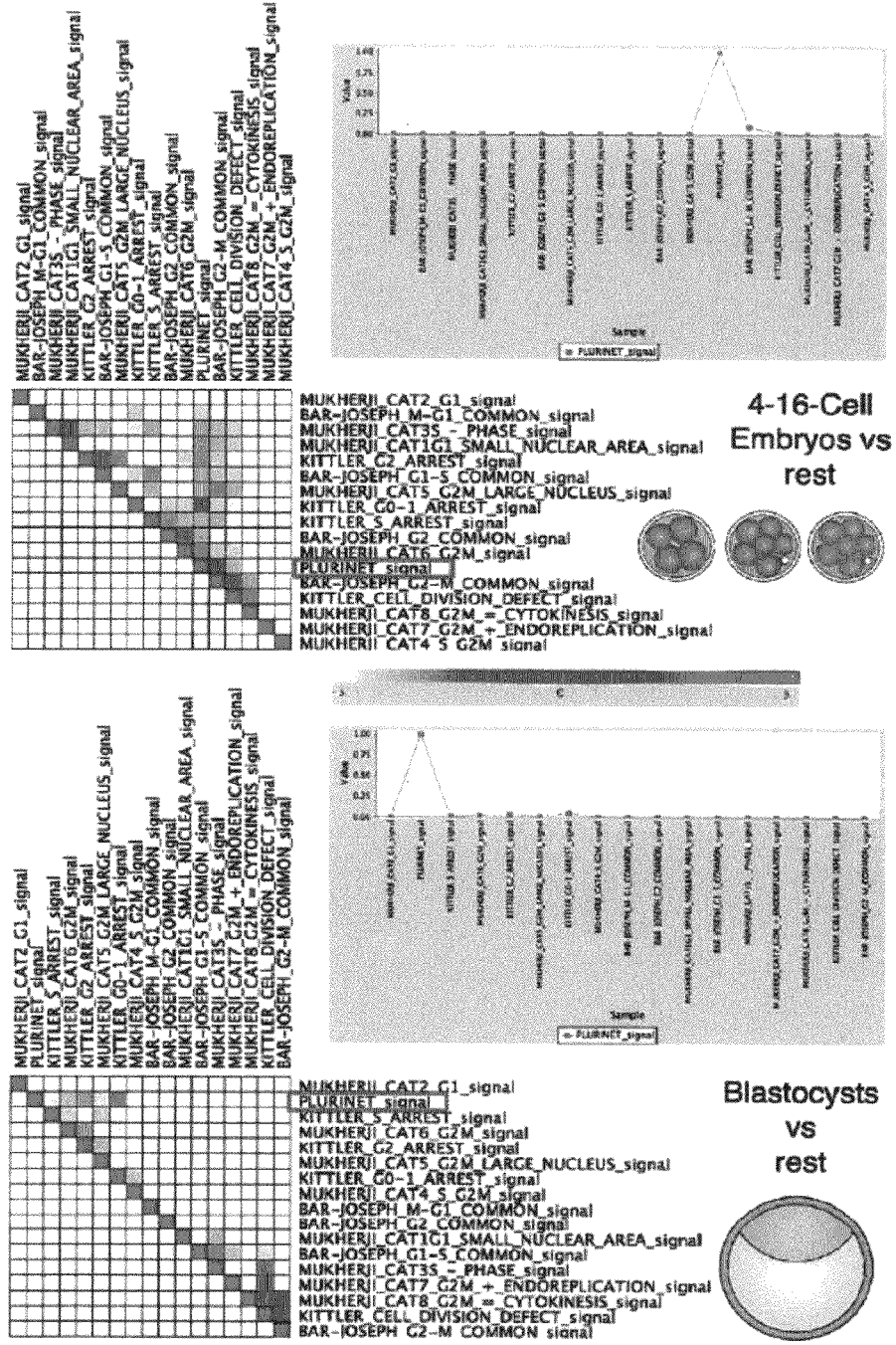

FIG. 18 shows a Murine preimplantation development leading edge analysis. The color-coded heat maps indicate, that the reported enrichment scores were not driven by genes that overlapped between PluriNet and the cell cycle-related gene. Plotting the overlap score in each developmental step shows that there is minimal leading edge signal overlap between only a few phase specific gene sets and PluriNet but not any other gene set that were analyzed.

FIG. 19 shows the cophenetic coefficient of Stem Cell Matrix datasets. (A) graph of the cophenetic coefficient at each number of clusters for the Stem Cell Matrix core dataset (153 samples, clusterings k=2 to 15) (Sokal et al. Taxon 11:33-40, 1962). Because of its stability, k=12 (indicated by red circle) was selected as the k value for further analysis. (B) Graph of the cophenetic coefficient at each number of clusters for the Stem Cell Matrix core plus test dataset (219 samples, clusterings k=2 to 17) (Sokal et al. Taxon 11:33-40, 1962). Because of its stability, k=15 (indicated by red circle) was selected as the k value for further analysis.

Figure 20A:
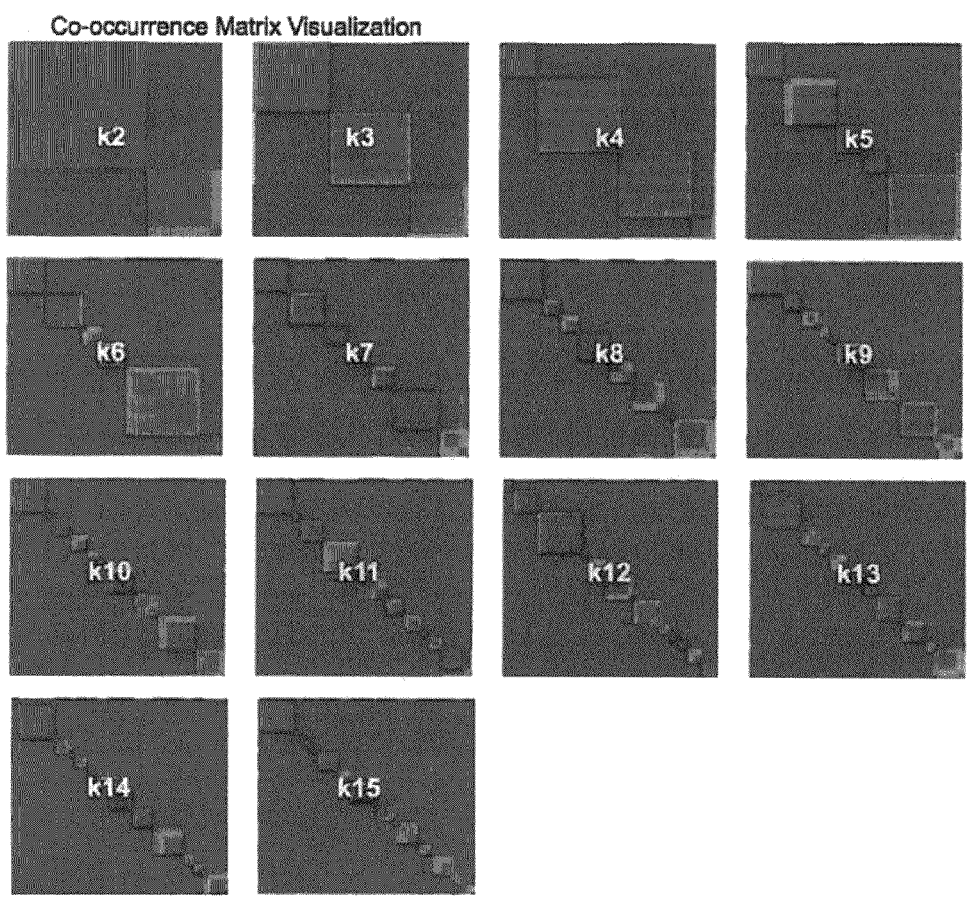
Figure 20B:
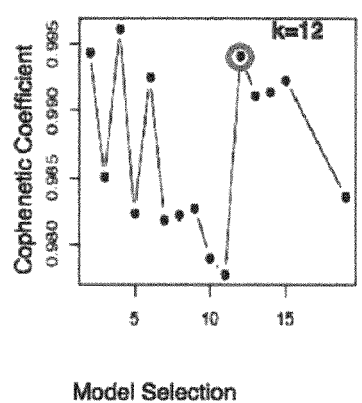
Figure 20C:
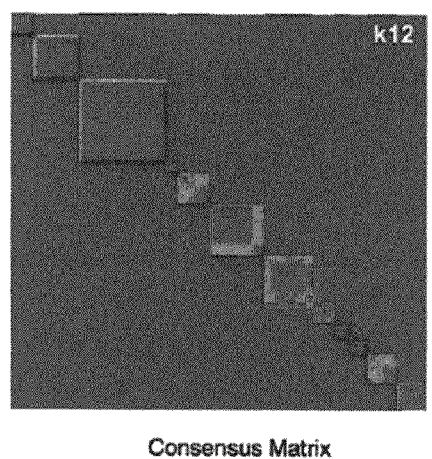

FIG. 20 shows the co-occurrence matrix visualization of Bootstrapped sparse Non-negative Matrix factorization.

Figure 21A:
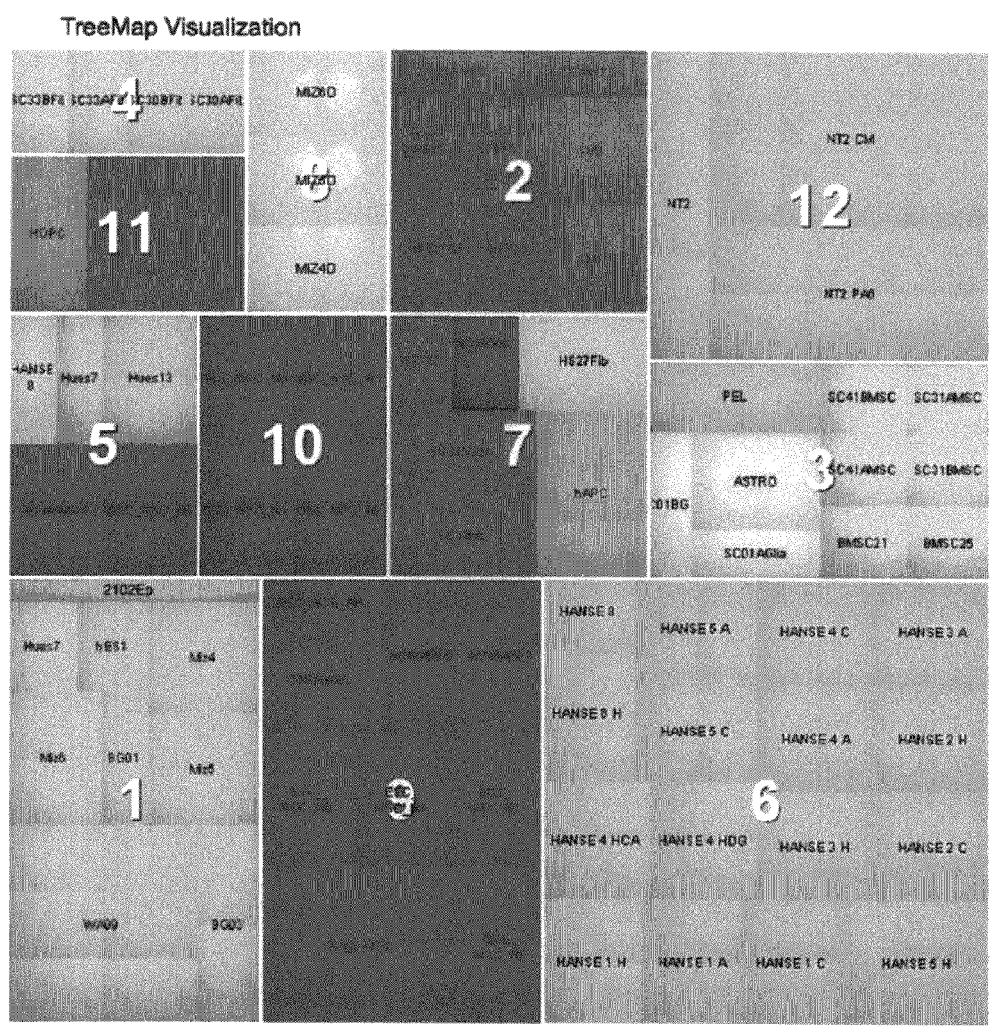

FIG. 21 shows the TreeMap visualization of the Bootstrapped sparse Non-negative Matrix factorization.

Figure 22A:
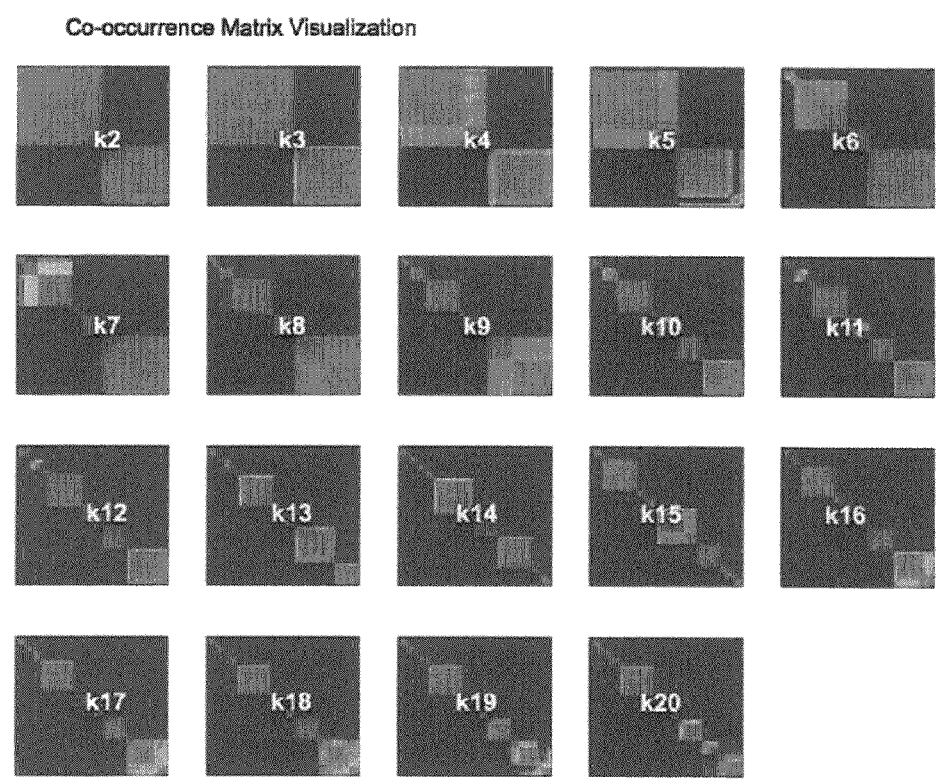
Figure 22B:
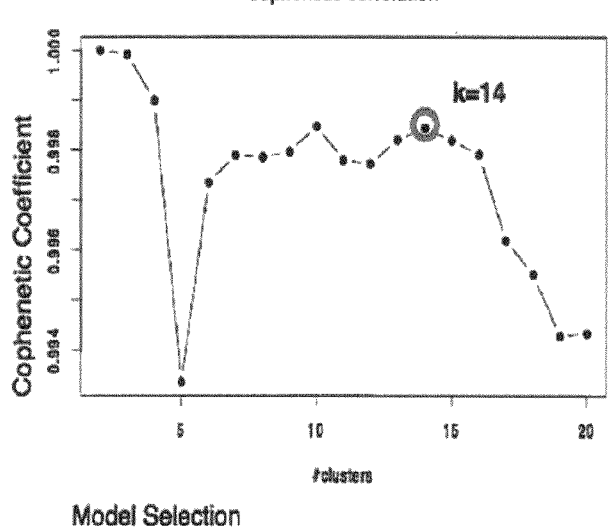
Figure 22C:

FIG. 22 shows the co-occurrence matrix visualization of Hierarchical Clustering.

Figure 23A:
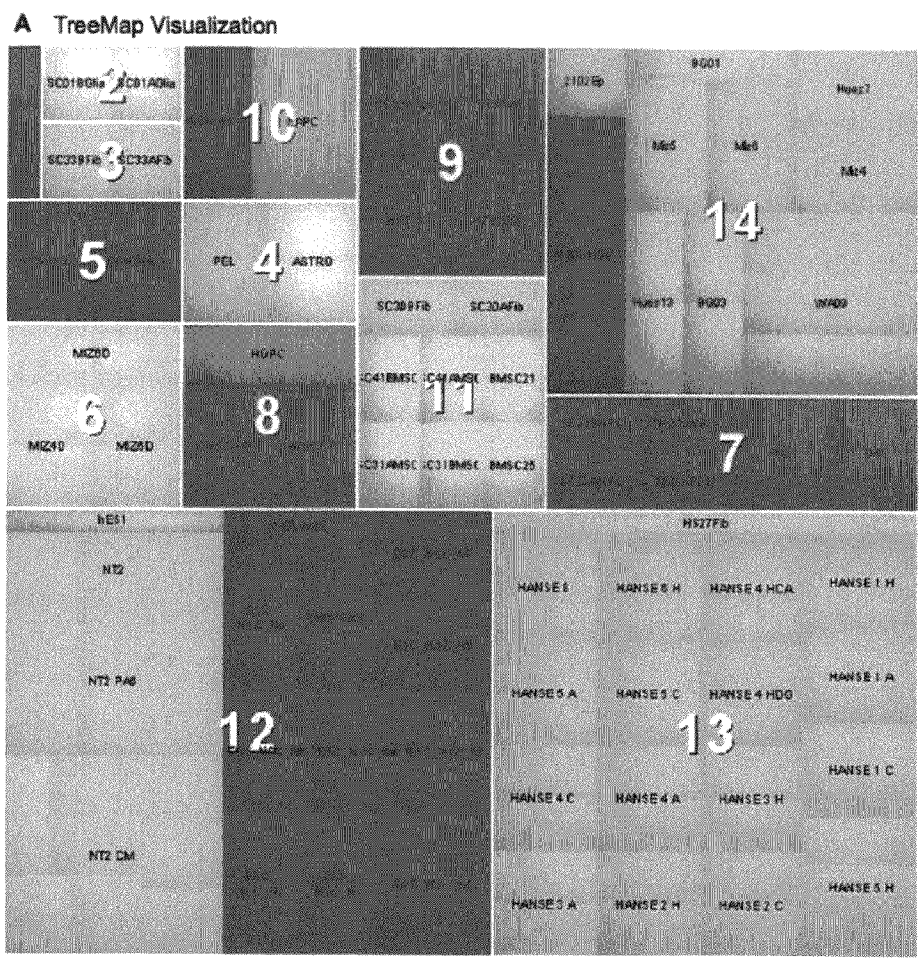
Figure 23B:
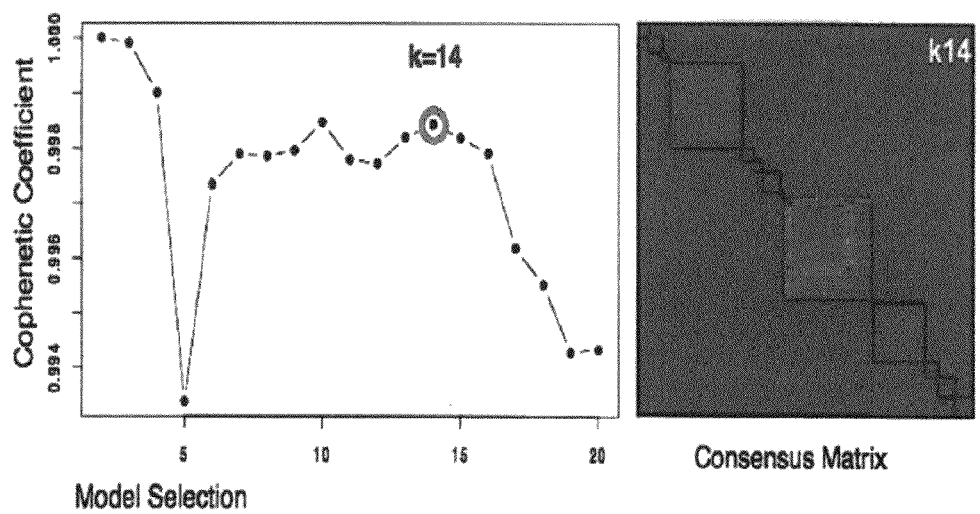
Figure 23C:

FIG. 23 shows the TreeMap visualization of the Hierarchical Clustering.

Figure 24A:
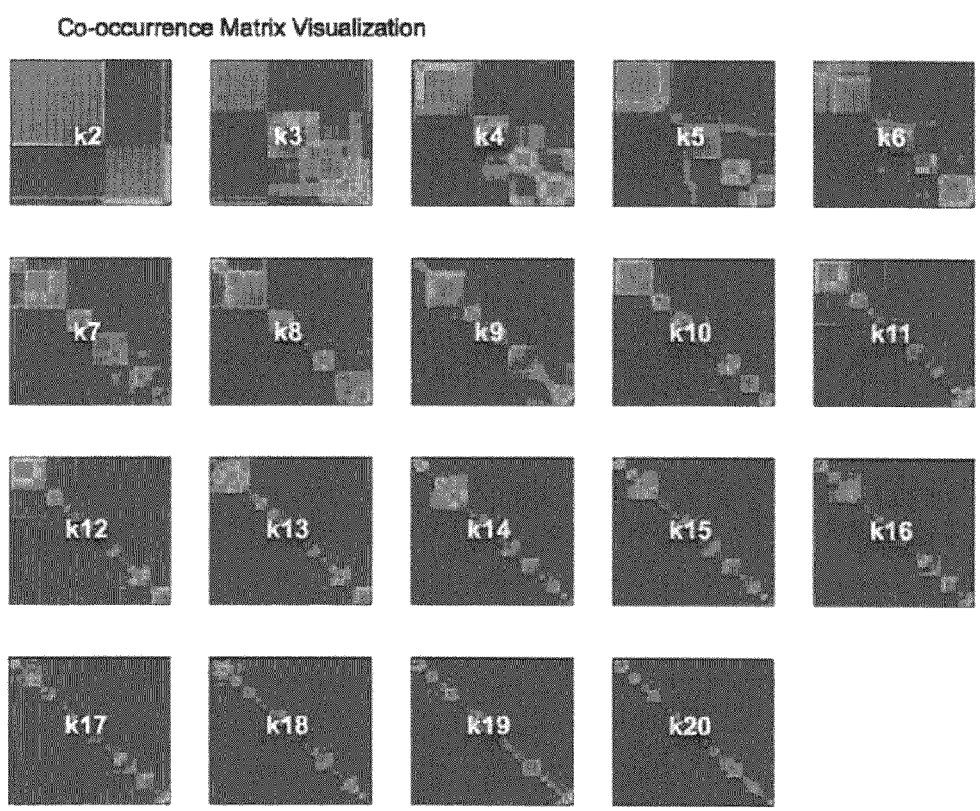
Figure 24B:
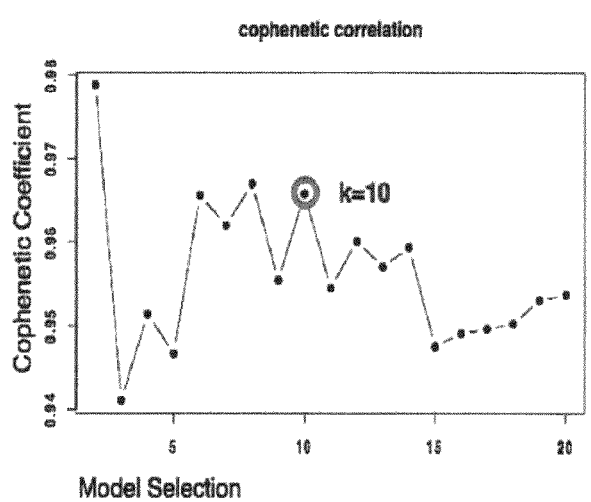
Figure 24C:
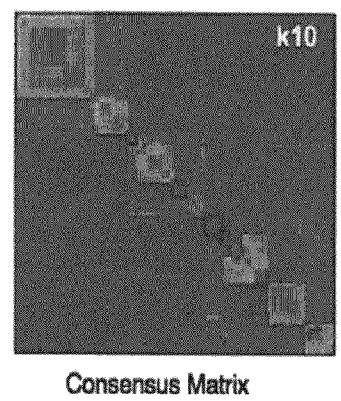

FIG. 24 shows the co-occurrence matrix visualization of K-means Clustering.

Figure 25A:
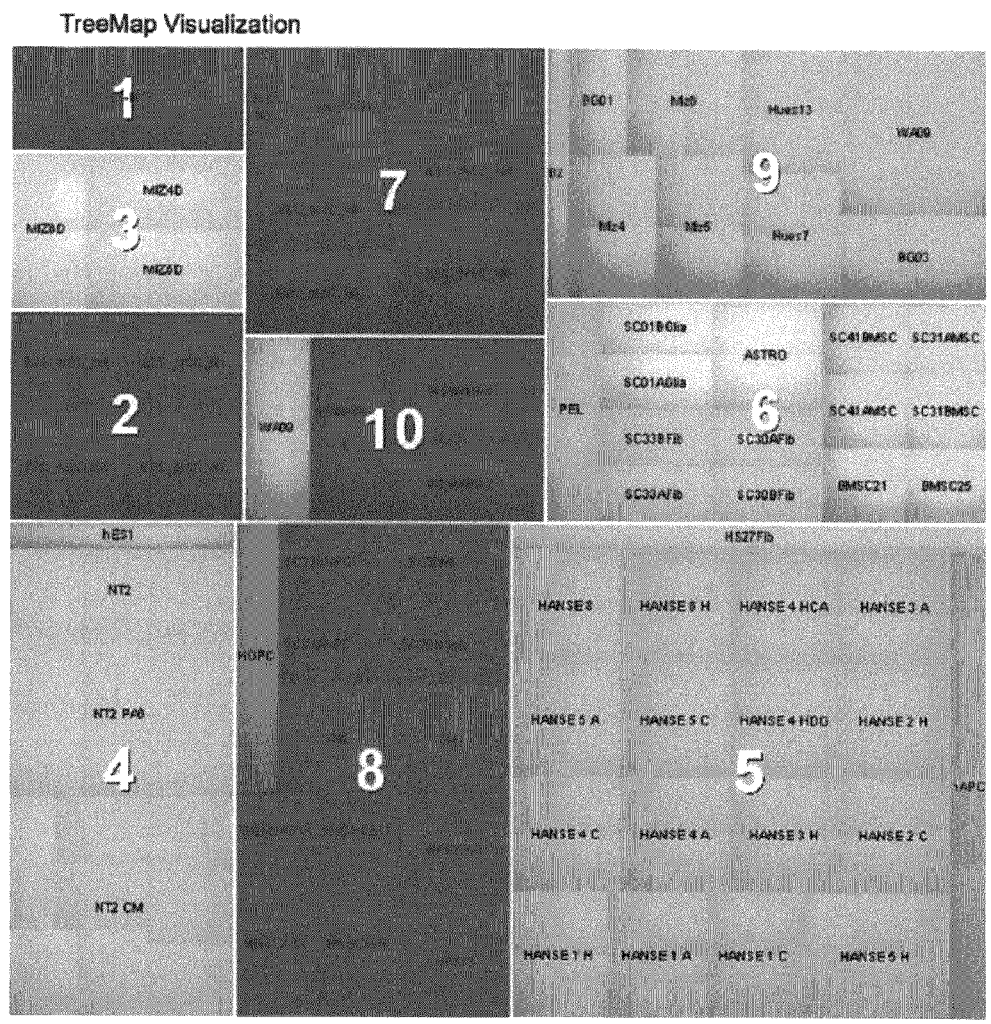
Figure 25B:
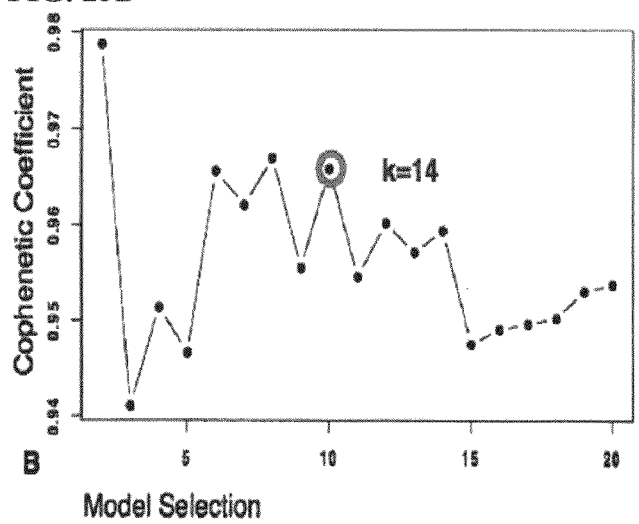
Figure 25C:

FIG. 25 shows the TreeMap visualization of the K-means Clustering.

Figure 26A:
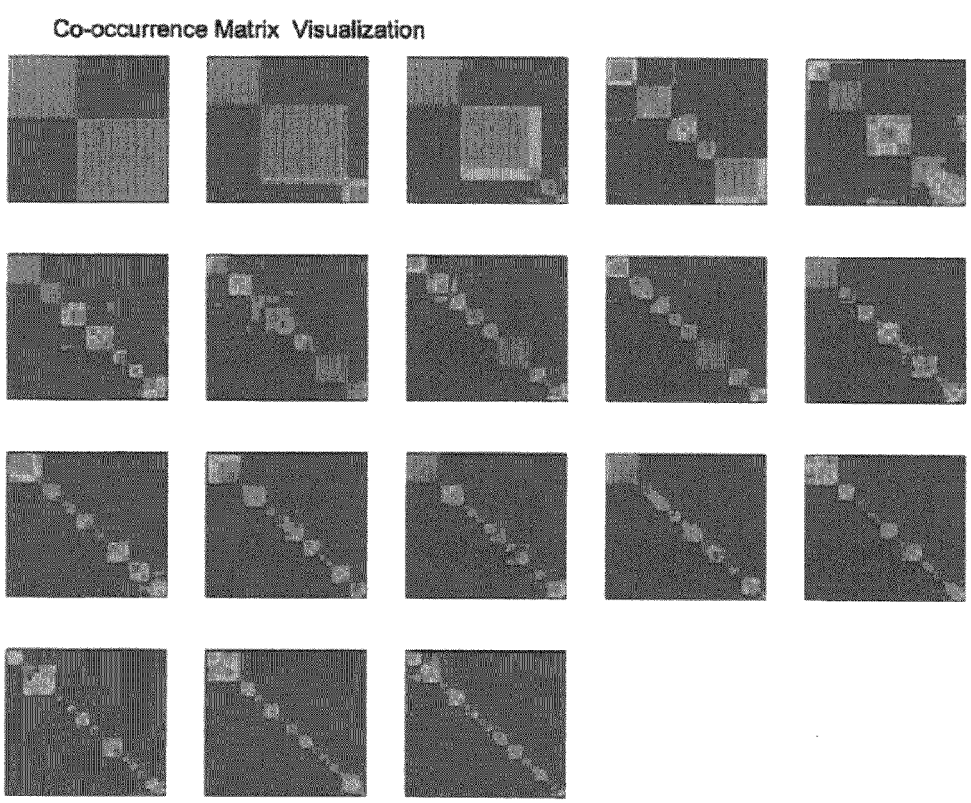
Figure 26B:
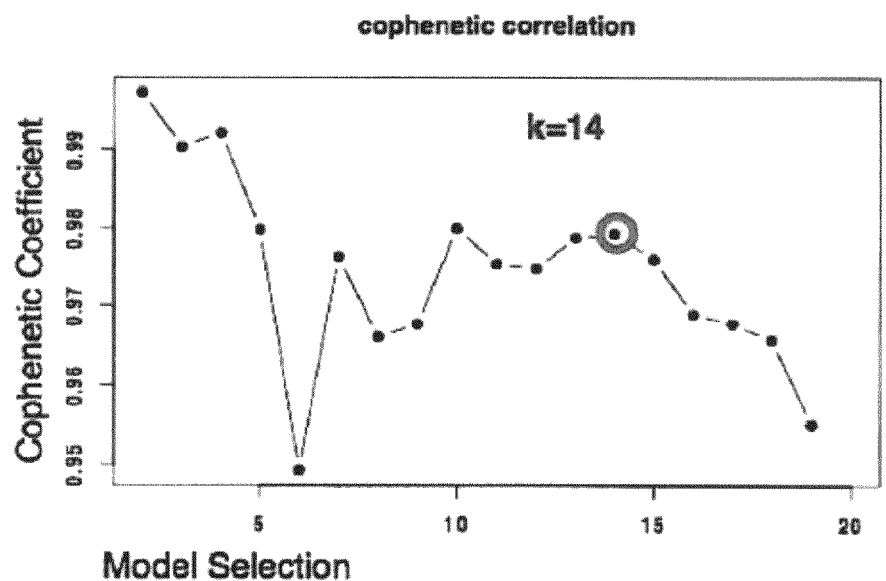
Figure 26C:
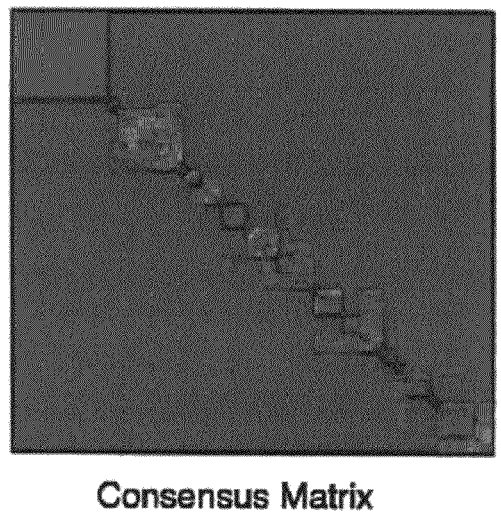

FIG. 26 shows the co-occurrence matrix visualization of Self-Organizing Maps.

Figure 27A:
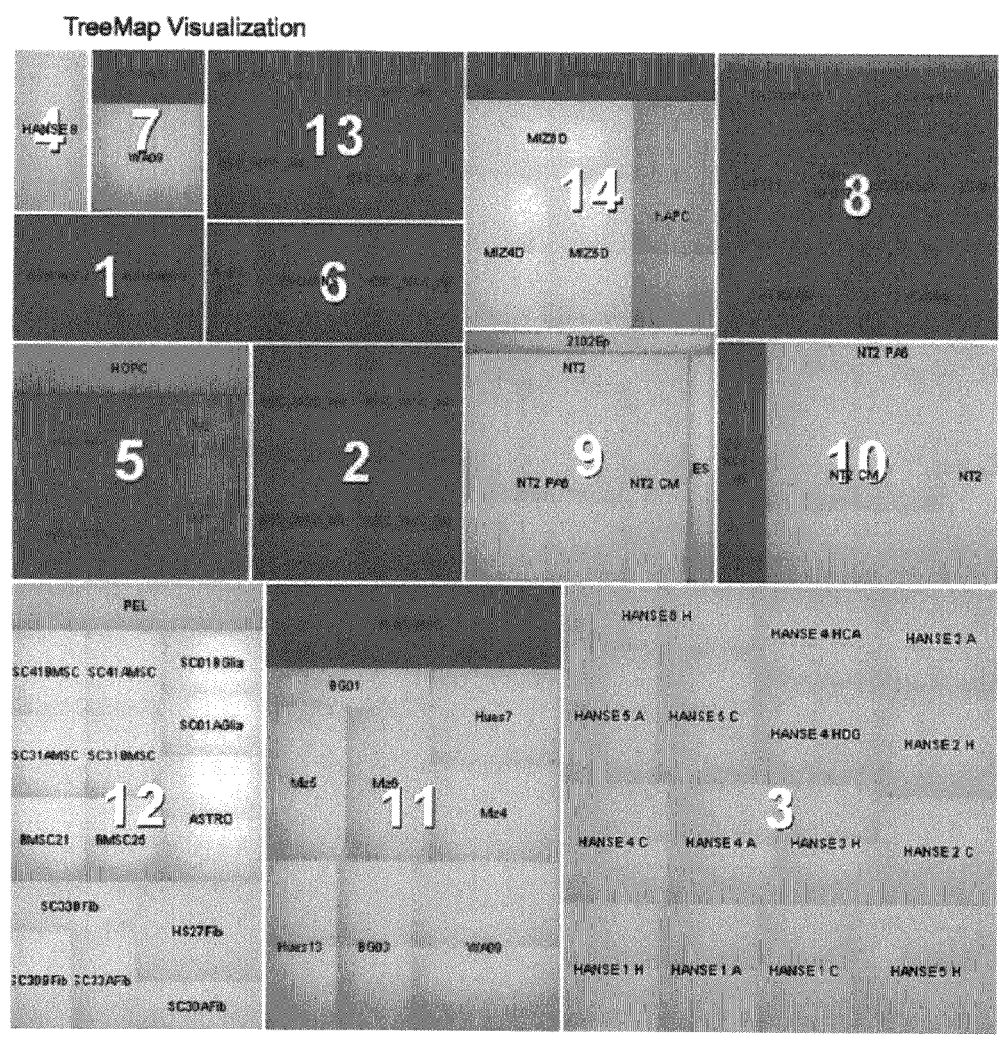
Figure 27B:
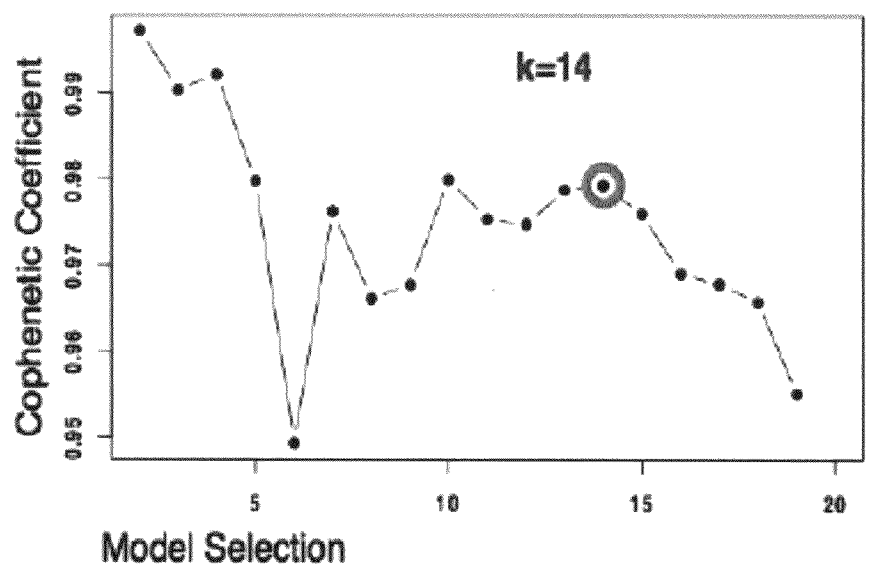
Figure 27C:
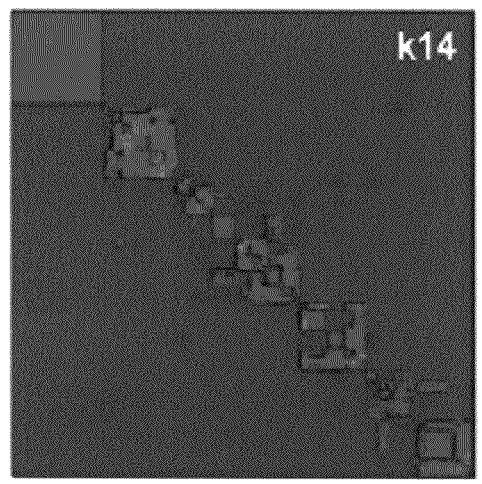

FIG. 27 shows the TreeMap visualization of Self-Organizing Maps.

Figure 28A:
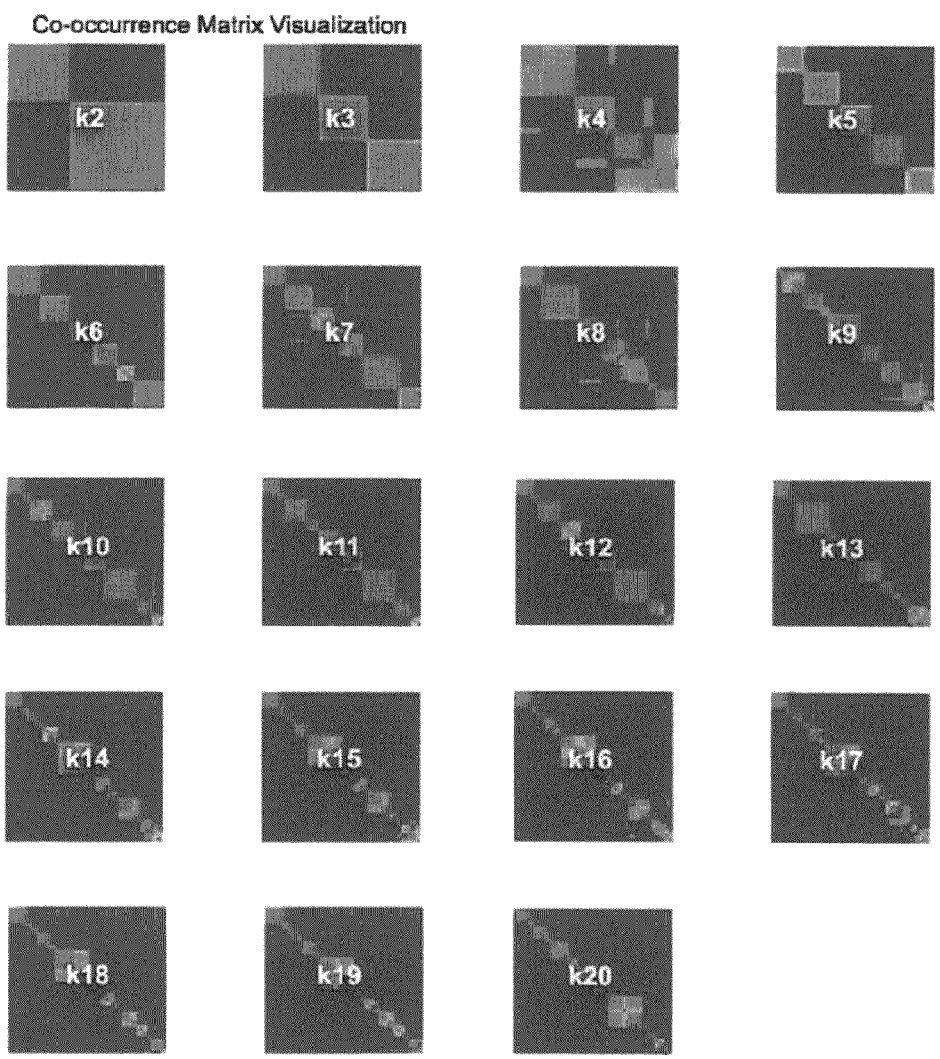
Figure 28B:
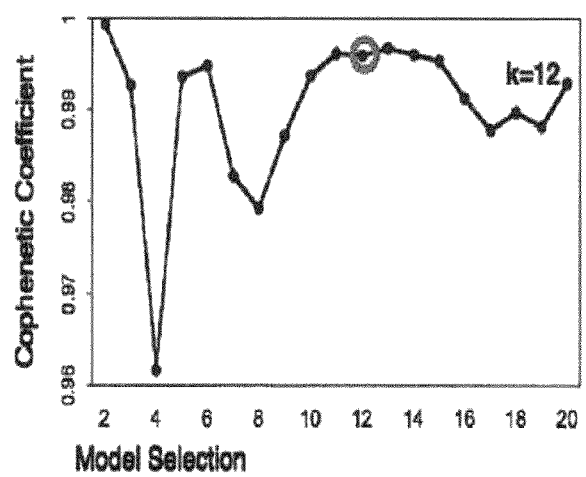
Figure 28C:
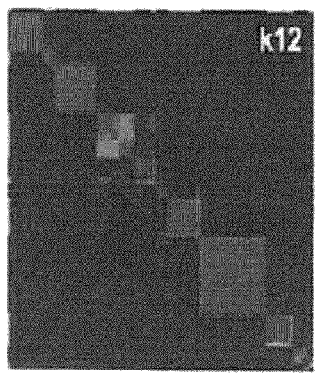

FIG. 28 shows the co-occurrence matrix visualization of Non-negative Matrix Factorization.

Figure 29A:
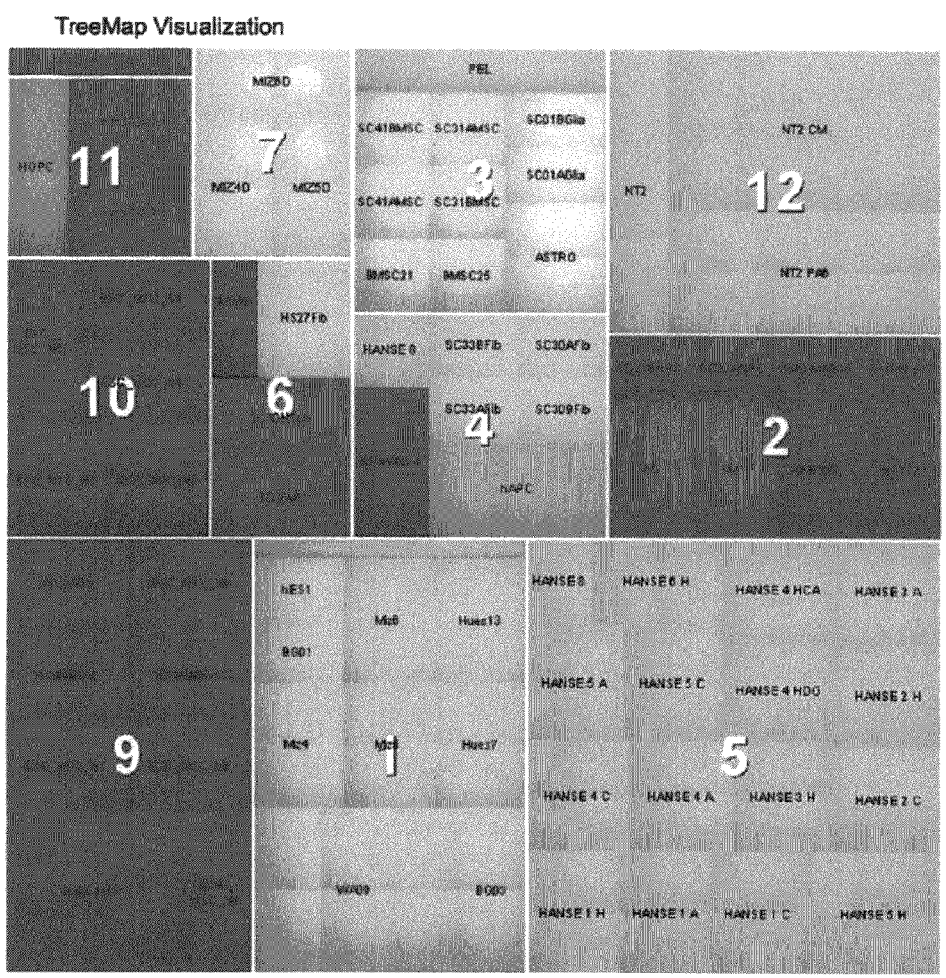
Figure 29B:
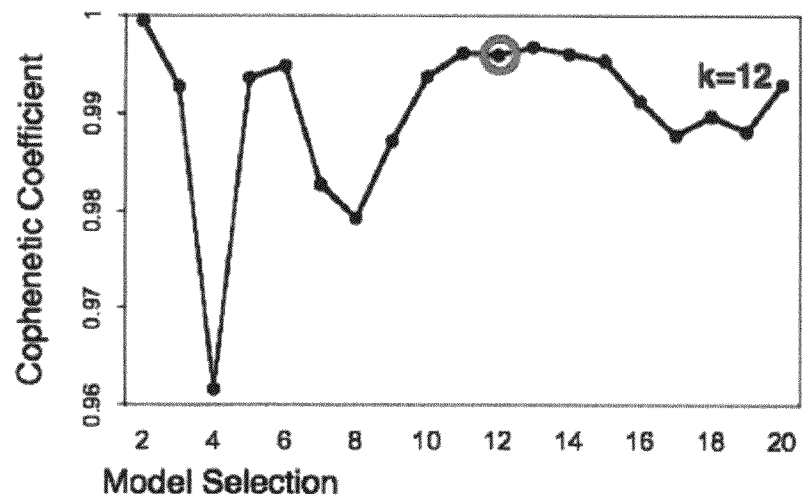
Figure 29C:
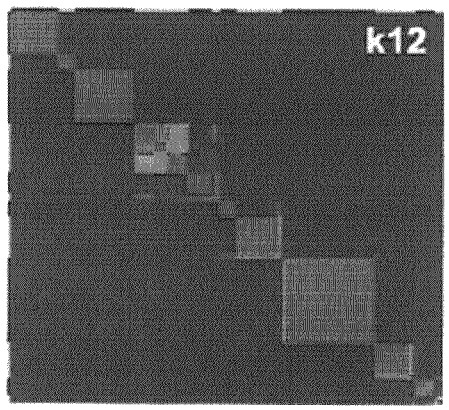

FIG. 29 shows the TreeMap visualization of Non-negative Matrix Factorization.

DETAILED DESCRIPTION OF INVENTION

A. Definitions

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

B. Definitions

1. A, An, The

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

2. About

About modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. Whether modified by the term "about" the claims appended hereto include equivalents to these quantities.

3. Abbreviations

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, "M" for molar, and like abbreviations).

4. Activity

As used herein, the term "activity" refers to a biological activity.

5. Cell

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

6. Cell Culture

"Cell culture" or "cell culturing" refers to the process by which either prokaryotic or eukaryotic cells are grown under controlled conditions. "Cell culture" not only refers to the culturing of cells derived from multicellular eukaryotes, especially animal cells, but also the culturing of complex tissues and organs.

7. Compound and Composition

Compounds and compositions have their standard meaning in the art. For the purposes of the present disclosure the terms "compound" and "composition" can be used for any reference of a molecule or like herein for the chemical entities described herein, including all enantiomeric forms, diastereomeric forms, salts, and the like.

8. Components

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these molecules may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

9. Comprise

Throughout the description and claims of this specification, the word "comprise" and variations of the word, such as "comprising" and "comprises," means "including but not limited to," and is not intended to exclude, for example, other additives, components, integers or steps.

10. Consisting Essentially of

"Consisting essentially of" in embodiments refers, for example, to a surface composition, a method of making or using a surface composition, formulation, or composition on the surface of the biosensor, and articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agents, a particular cell or cell line, a particular surface modifier or condition, a particular ligand candidate, or like structure, material, or process variable selected. Items that may materially affect the basic properties of the components or steps of the disclosure or may impart undesirable characteristics to the present disclosure include, for example, decreased affinity of the cell for the biosensor surface, aberrant affinity of a stimulus for a cell surface receptor or for an intracellular receptor, anomalous or contrary cell activity in response to a ligand candidate or like stimulus, and like characteristics.

11. Global Profiling

A global profile is a profile of a characteristic, such as, but not limited to, expression of mRNA, microRNA, DNA methylation, DNA sequence, transcription factor binding, proteins, proteome-wide phospho-proteins, in which there is not a preselection of what genes, DNA sites or what proteins or what subset of the characteristic should be profiled with a specific technique (e.g. microarrays).

12. Higher

The terms "higher," "increases," "elevates," or "elevation" or variants of these terms, refer to increases above basal levels, e.g., as compared to a control. The terms "low," "lower," "reduces," or "reduction" or variation of these terms, refer to decreases below basal levels, e.g., as compared to a control. For example, basal levels are normal in vivo levels prior to, or in the absence of, or addition of an agent such as an agonist or antagonist to activity.

13. Inhibit

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

14. Labeled RNA Binder,

A "labeled RNA binder" or like terms refers to a molecule comprising a detection agent.

15. Optionally

"Optional" or "optionally" means that the subsequently described event or circumstance may or may not occur, and that the description includes instances where said event or circumstance occurs and instances where it does not.

16. Optional

"Optional" or "optionally" or like terms means that the subsequently described event or circumstance can or cannot occur, and that the description includes instances where the event or circumstance occurs and instances where it does not. For example, the phrase "optionally the composition can comprise a combination" means that the composition may comprise a combination of different molecules or may not include a combination such that the description includes both the combination and the absence of the combination (i.e., individual members of the combination).

17. Primers

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

18. Protein-Protein Network

A protein-protein network is a list of pairwise interacting proteins. These interactions have been derived from previous studies where e.g. the binding of a protein "A" to protein "B" has been shown with biochemical, functional or other biological assays. This interaction can represent a physical covalent or non-covalent binding event of protein "A" with protein "B" or the transient binding of protein "A" to protein "B" in a short lived biochemical reaction such as when protein "A" phosphorylates protein "B".

19. Probes

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

20. Prevent

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

21. Publications

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

22. Or

The word "or" or like terms as used herein means any one member of a particular list and also includes any combination of members of that list.

23. Ranges

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

24. Reduce

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

25. Sample

By sample or like terms is meant an animal, a plant, a fungus, etc.; a natural product, a natural product extract, etc.; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

26. Stem Cell Matrix

A stem cell matrix is a collection or database of global profiling data, such as global molecular analysis profiles, which may be gene expression profiles, microRNA expression profiles, non-coding RNA profiles, DNA methylation profiles, transcription factor binding profiles, proteomic profiles, global proteome-wide phospho-protein profiles, DNA sequence profiles, or a combination of elements of the mentioned global profiles.

27. Subject

As used throughout, by a subject or like terms is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) and mammals, non-human mammals, primates, non-human primates, rodents, birds, reptiles, amphibians, fish, and any other animal. In one aspect, the subject is a mammal such as a primate or a human. The subject can be a non-human.

28. Treatment

"Treating" or "treatment" does not mean a complete cure. It means that the symptoms of the underlying disease are reduced, and/or that one or more of the underlying cellular, physiological, or biochemical causes 29. Transcriptional Profile A transcriptional profile is the complete or partial set of data obtained from a cell or a population of cells that can be determined from a single time point or over a period of time, consisting of the RNA types that are transcribed from the genome. These RNA types include, but are not limited to, mRNA, microRNA (miRNA), PIWI-interacting RNAs (piRNAs), endogenous small interfering RNAs (e-siRNAs), TINY RNAs (tiRNA), long non coding RNAs or a combination of the mentioned RNA-types 30. Computer Network A computer network or like terms are one or more computers in operable communication with each other.

31. Computer Implemented

Computer implemented or like terms refers to one or more steps being actions being performed by a computer, computer system, or computer network.

32. Computer Program Product

A computer program product or like terms refers to product which can be implemented and used on a computer, such as software.

33. Unsupervised Classification

Unsupervised classification is a computational, algorithm-based classification system, which builds models based on a set of inputs where not all labels for all samples are available or known or understood. As disclosed herein, what has been defined by others as semi-supervised machine learning, which combines both labeled and unlabeled examples to generate an appropriate function or classifier, as unsupervised classification system, can be used.

34. Unsupervised Cluster Method

An unsupervised cluster method is an unsupervised machine learning approach to cluster transcriptional profiles of the cell preparations into stable groups.

For example, consensus clustering (Monti, S., P. Tamayo, J. Mesirov and T. Golub (2003). "Consensus Clustering: A Resampling-Based Method for Class Discovery and Visualization of Gene Expression Microarray Data." *Machine Learning* 52 (1-2): 91-118.) outputs a sample-wise distance matrix where the distance between every sample to every other sample in the dataset is represented by a value set between 1 (indistinguishable similar in the context of the data set) and 0 (no similarity detectable in the context of the dataset). A cluster is defined in the consensus clustering framework of a set of samples with high similarity based on the sample-wise distance matrix based on a cutoff set by the consensus clustering algorithm individually for each model. Every other algorithm which outputs a fitting clustering model with and distance measure among all samples can be used instead of the consensus clustering algorithm.

35. Similar Label Profile

A similar label profile could be a common regulatory biochemical or metabolic activity. A similar label profile could be labels from the reference data set (e.g. induced pluripotent stem cells), labels which were derived computationally (e.g. some or all samples belonging to one or more specified clusters) or a combination thereof (e.g. some or all induced pluripotent stem cells which also belong to one or more computationally derived clusters). This could be the identification of a set of marker genes, proteins or pathways different among computationally derived clusters, which can be identified in the future with other biochemical techniques and thus allow identification of computationally identified cluster members with a biochemical assay.

36. Labeled Associated Biological Classes

A labeled associated biological class is a class based upon a biological definition of a cell, such as by markers or expression, with the main characteristic being that the class is determined by a subset of the total possible profile information.

37. Cell Characteristic Analysis System

A cell characteristic analysis system is a system which can assay a characteristic of a cell, such as gene expression, microRNA expression, or methylation patterning.

38. Obtaining

Obtaining as used in the context of data or values, such as characteristic data or values refers to acquiring this data or values. It can be acquired, by for example, collection, such as through a machine, such as a micro array analysis machine. It can also be acquired by downloading or getting data that has already been collected, and for example, stored in a way in which it can be retrieved at a later time.

39. Outputting Results

Outputting or like terms means an analytical result after processing data by an algorithm.

40. Updated Reference Database

An updated reference database or like terms is a reference database which has had a dataset merged into it.

41. Cell Datasets

A cell dataset or like terms refers to any collection of characteristic data.

42. Characteristic Data

Characteristic data refers to any data of a cell, such as gene expression, microRNA expression, or for example, methylation patterning.

43. Values

Specific and preferred values disclosed for components, ingredients, additives, cell types, markers, and like aspects, and ranges thereof, are for illustration only; they do not exclude other defined values or other values within defined ranges. The compositions, apparatus, and methods of the disclosure include those having any value or any combination of the values, specific values, more specific values, and preferred values described herein.

Thus, the disclosed methods, compositions, articles, and machines, can be combined in a manner to comprise, consist of, or consist essentially of, the various components, steps, molecules, and composition, and the like, discussed herein. They can be used, for example, in methods for characterizing a molecule including a ligand as defined herein; a method of producing an index as defined herein; or a method of drug discovery as defined herein.

44. Weight %

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

C. Methods

Defining what characterizes a specific type of cell has plagued scientists for many years. Sometimes a cell or collection of cells is defined by what the cell does or is expected to do. For example, a pancreatic islet cell produces insulin, a neuron releases a neurotransmitter or makes and electrical connection, and a pluripotent stem cell is defined as a cell that can divide indefinitely without differentiating, but can under the appropriate conditions differentiate into all three germ layers, mesoderm, ectoderm, and endoderm. While this type of definition is very helpful, it also is problematic. For example, functional definitions can only identify cells at a specific time point, under a specific set of conditions. Cells may, as part of their particular identity, have multiple functions or characteristics that change over time. Another problem is that, just as in structural biology many protein structures exist to solve a given functional problem, so also more than one cell type can exist which achieves a given set of functional properties. Are these different cells then, or the same cell? This problem is magnified when cells are removed from their sites in the body and are placed into tissue culture. An example of this can be found in the pluripotent stem field. Embryonic germ cells, embryonic stem cells, and induced pluripotent stem cells all purportedly meet the functional definition provided above for a pluripotent stem cell. However, the cells express different markers, have different ratios of proteins, and look morphologically different. Are they the same cell type or a different cell type?

Scientists have attempted to address the limitations of functionally defining cells by defining them based on observable "markers." Marker as used in this context is a particular protein or gene or glycoprotein, for example, which is present, or not present, on the cell type of interest relative to another cell type. Typically this type of structural definition uses many markers. Problems exist with this type of definition as well. For example, expression markers believed to be typical of a specific cell type are often found on other types of cells. Thus, markers are not sufficient to distinguish specific cell types.

Lastly, cells can be defined by where they come from, for example, from a liver organ, a heart organ, or a muscle. A cell isolated from this type of tissue and then cultured is a cell that makes up the particular tissue. This way of defining a cell ultimately has problems as well, as the cells change after repeated doublings in culture, so that they may no longer be similar to the type of cell that makes up the organ.

The compositions, methods, algorithms, and systems disclosed herein are designed to produce a new way of defining a cell. This new way is called a computed definition and the previous types of definitions are referred to as biological definitions (functional, structural, genesis). The computed definition is related to a biological definition, but as discussed herein, the computed definition provides a more robust and accurate way of comparing two different cells and determining whether they are the same type of cell or different cell types.

1. Reference Databases

The computed definition refers to the use of computational analysis of information to arrive at the definition. Disclosed are databases of information about one or more cells. For example, some of the databases are reference databases. A reference database can comprise cell datasets that are produced from cell data for at least two known cell lines, tissues, or primary cells. By known cell line, tissue, or primary cell is meant a cell line for which some characteristic, such as phenotype, such as a stem cell, such as an embryonic stem cell can and has been identified by conventional biological assays, e.g. derivation method, source material, biochemical assays (e.g. alkaline phosphatase activity) or markers like specific, identified proteins which are thought to be able to identify a specific cell type. A computed phenotype can be defined by the global profiling methods, such as gene expression (or other molecular profiling method) which is then utilized in the methods disclosed herein. Biological phenotypes, such as whether a cell is a stem cell or differentiated cell, which have been determined using subsets of profiling data, such as a subset of markers or gene expression, can be used and incorporated into the methods in the form of labeled associated biological classes.

A reference database can be a stable database which is compiled and is stable and can be used over and over again, like an atlas. However, a reference database can also be self-evolving. By self-evolving is meant that each time the database has something compared to it, it is used as a control or comparison to some other cell having a question about a property for which the database has been sorted, the reference database can be updated with the a new member. This can be referred to as an updated reference database. It is understood that an updated reference database is also a reference database.

In certain embodiments, the reference database and updated reference databases can exist in a shared way, such that multiple users can access them and update them, such as a central database.

The reference database is made up of cell datasets, and each cell dataset is made up of characteristic data. Characteristic data are output from, for example, mRNA expression analysis, microRNA expression analysis, protein expression analysis, post-translational protein modification analysis, non-coding RNA expression analysis, DNA methylation pattern analysis, histone modification analysis, transcription factor—DNA site binding analysis, DNA sequence analysis or any other type of cell characteristic.

The methods, compositions, and machines, disclosed herein typically use cell types that are important or desired in research, such as medical research or developmental research. For example, the cells could be stem cells, such as pluripotent stem cells, or the cells could be chosen to include every cell type from the human body, genetically engineered or not engineered, cultured or isolated from tissues or organs, from embryonic, fetal, or adult material. While the database can be produced with a subset of cells from a given biological class, the database can also be produced from a "complete" set of the biological classes. For example, a reference database comprised of pluripotent cells could have 10 cell lines or the database could be comprised of as many of the pluripotent cell lines as possible. Generally, for most purposes the database is produced to include more datasets.

The characteristic data is obtained by global profiling. Global profiling refers to obtaining characteristic data from whole genome transcriptional profiling, and can include for a Stem Cell Matrix, whole genome methylation profile, whole genome microRNA expression profiles, whole genome non-coding RNA profiles, whole genome histone modification profiles, or DNA sequence profiles, for example. Typically one wants to examine as much data as possible, and incorporate this into the database. As used herein, a matrix refers to a reference database of a particular set of biologically defined cells, for example, stem cells or liver cells. A key aspect of global profiling is the lack of predetermined data biasing. For example, with stem cells one can examine the mRNA expression of a set of biologically defined stem cells. The literature related to these particular stem cells may identify, for example, a set of 25 genes that are expressed in a cell that the literature identifies as a "stem cell." To arrive at a computed definition of these cells, the reference database is made up of the cell dataset which is made up of the characteristic data, which in this case is the mRNA expression data, but when obtaining the mRNA expression data it is not limited to the 25 genes, it is made up of 100, 500, 1000, 5000, or even 25,000 genes. The biological definition of the known gene expression of the biologically defined stem cells is used to pick the initial set of cells, but it is not used to arrive at the computed definition.

This concept can be applied for any characteristic made up in a global profile, which is the set of all different characteristics for which data are obtained for the reference database. Described in another way, a global profile can be made up of one dataset as disclosed herein for one characteristic, but it can also include more than one dataset for more than one characteristic.

It is not required that there be a certain number of members in the dataset, however generally more members are preferred. But what is required is that a prespecified marker set, as discussed herein, not be used. One way of achieving this is to use microarrays, or the like, and examine all of the elements of the array, not just a subset. One could, for example, examine all expressed genes. A key aspect to the overall success of the computed definition occurs in the implementation of a like global profiling method for comparing a dataset of a cell to the reference database. For example, in certain embodiments if three different characteristics, such as mRNA expression, microRNA expression, and DNA methylation of 100 cells are used to produce a reference database, and 1000 members are assayed for each characteristic (i.e. the expression of 1000 genes), when comparing the next cell (unknown cell) to the database at least 80%, 85%, 90%, 95%, 97%, 99%, or 100% of the members are assayed for the unknown cell. This is particularly important if the dataset for the unknown cell will be used to update the reference database. Thus, the global profiling of an unknown should match at least 80%, 85%, 90%, 95%, 97%, 99%, or 100% to the global profiling of the reference database the unknown is being compared to or updating.

It should be noted that the concept of examining "all" expression of a cell is contrary to the accepted way of examining a cell. The standard way of achieving comparison is to look at a subset of markers, for example, expressed genes. This subset, however, is a form of a biological definition, not the computed definition of a cell disclosed herein.

A computed definition takes datasets and lets an algorithm group the datasets into computed clusters. A computed cluster is a subset of a datasets that meet similarity requirements.

After, during, or before, clustering, a dataset can be produced which includes biological definitions, labels, and characteristics of the cell or cells. This type of information can be, for example, impressions such as morphological observations that led a researcher to consider that the cell is a stem cell.

A test dataset is a dataset that is produced from a cell for which a computed definition is desired. It is produced from characteristic data for an unknown cell line, tissue, or primary cell. Unknown in this context means that a computed definition is desired. Typically the test dataset will be comprised of a global profile as discussed herein as it relates to the global profile of the reference database. The test dataset can be merged with the reference database forming an updated reference database. In certain embodiments this can be as simple as adding the data to an existing spreadsheet.

At some point after a reference database is received the methods can include performing unsupervised classification. This means that a new sorting of the data is performed, with no preconceptions about the results of the sorting. The sorting is typically performed multiple times, at least 5, 10, 20, 50, 100, 200, 300, 500, for example. The sorting results are analyzed for a result that is stable, meaning that the result of the sorting is providing the same result, or a similar result (at least 80%, 85%, 90%, 95%, 97%, 99% or 100% of the previous result). The re-sorting of the data can be performed completely de novo or it can start with certain assumptions.

The methods include performing automatic model selection, meaning that a model selection system can be obtained from the unsupervised clustering. For example, a consensus cluster method can be used. This consensus clustering method sorts samples into many groups and tests each grouping for stability. It does the same classification over and over again, but starts from another point. If the groupings or clusterings are stable, the method will always arrive at the same or nearly the same members in each group. There are multiple algorithms for testing the stability of groups; the essential part is that the method provides multiple choices of models.

Typically, it is desirable to determine how many groups or clusters are in the data under analysis, and the goal is to find the optimal solution for a given dataset. In certain embodiments, the grouping that is being sought is the one that best reveals the underlying biological mechanisms that cause samples to be grouped together. In certain embodiments, one introduces perturbations into the dataset and clusters the data again. The algorithm in certain embodiments may start at a different point. One may do this over and over, including at least 5, 10, 30, 50, 100, 300, or 500 or more times.

Typically, the methods also include selecting a best fitting classification model, wherein the best fitting classification model can have the samples identical to the matrix samples, the samples are similar, but not identical to the matrix samples, or the samples are different from all matrix samples. A definition of best fitting classification model is a model among all models that the algorithm identifies is the most stable to random perturbations; by stable is meant that the computation comes to the same or very similar conclusion at least 10 times.

Disclosed are methods of assaying a cell comprising, receiving a reference database, wherein the reference database comprises cell datasets produced from characteristic data for at least two known cell lines, tissues, or primary cells, wherein the data was obtained by global profiling, wherein the data was associated with one or more labeled associated biological classes of the cells, receiving a test dataset, wherein the test dataset comprises data produced for an unknown cell line, tissue, or primary cell, wherein the test dataset was obtained by a similar global profiling as for the reference database, merging the test dataset into the database producing an updated reference database, performing unsupervised classification of the updated reference database producing a computed label classification of the cells in the test dataset, and/or any limitation or characteristic disclosed herein alone or in combination.

Also disclosed are methods, further comprising the step of performing automatic model selection producing a best fitting classification model, wherein the best fitting classification model contains one or more clusters of the cells through reference to the clustering of the cell datasets; further comprising identifying which cluster or clusters the unknown cell is grouped in; further comprising outputting a computed definition of the unknown cell wherein the computed definition is referenced to the cluster the unknown cell resides in; wherein the best fitting classification model can cluster the individual datasets such that each dataset within a cluster is indistinguishable from each other dataset within the cluster; wherein the best fitting classification model can cluster the individual datasets such that each dataset within a cluster is similar to each other individual dataset in the cluster; wherein the best fitting classification model can cluster the individual datasets such that each dataset within a cluster is different from each other individual dataset; and/or any limitation or characteristic disclosed herein alone or in combination.

Also disclosed are methods, further comprising identifying computationally derived class labels only based on biological characteristics; further comprising identifying differences in at least one dataset for at least one label between at least two samples in at least two clusters; further comprising filtering within a cluster for samples within having a similar label profile, such as common regulatory biochemical or metabolic activity; further comprising defining differentially regulated networks; further comprising using the networks to define a class membership, manipulate class membership, or define biological function of an unknown cell; and/or any limitation or characteristic disclosed herein alone or in combination.

Disclosed are methods of characterizing cells as stem cells comprising: isolating cells and extracting RNA; analyzing the cellular RNA; isolating cells and extracting DNA; analyzing the DNA; isolating cells and extracting cellular proteins; analyzing the cellular Proteins; grouping the cells with an unsupervised machine learning approach to cluster RNA, DNA and/or Protein profiles; classifying the cells based on computationally derived protein-protein networks, and/or any limitation or characteristic disclosed herein alone or in combination.

Also disclosed are methods, wherein the stem cells are embryonic stem cells; wherein the stem cells are induced pluripotent stem cells; wherein the stem cells are somatic multipotent cells, such as neural stem cells, mesenchymal stem cells, or cardiac stem cells; wherein the analysis of cellular RNA consists of microarray analysis; wherein the unsupervised machine learning approach comprises a bootstrapping sparse non-negative matrix factorization; wherein the transcriptional profile is a global gene expression profile called a stem cell matrix; wherein the protein-protein network is the PluriNet; and/or any limitation or characteristic disclosed herein alone or in combination.

Disclosed are methods of characterizing cells comprising: global profiling of known and unknown samples; collecting reference data from known samples into a matrix database; merging the unknown sample data with the matrix database; grouping the cells with a machine learning algorithm; determining the identity of the unknown sample based on its similarity to the known sample matrix, and/or any limitation or characteristic disclosed herein alone or in combination.

Also disclosed are methods, wherein the sample is a cell line, primary cell or tissue; wherein the global profile is a transcriptional profile; wherein the matrix consists of known class labels; wherein the machine learning algorithm is an unsupervised classification; wherein the unsupervised machine learning algorithm comprises a bootstrapping sparse non-negative matrix factorization; wherein the machine learning algorithm is a supervised classification; wherein the method is a computer implemented method; further comprising the step of outputting results from the unsupervised classification; and/or any limitation or characteristic disclosed herein alone or in combination.

Disclosed are methods of analyzing a cell comprising; receiving an updated reference database; performing unsupervised classification on the database and outputting results from the unsupervised classification; wherein the method is a computer implemented method; wherein receiving the updated reference database comprises receiving the updated reference database from a storage medium; wherein receiving the updated reference database comprises receiving the record from a computer system; wherein receiving the updated reference database comprises receiving the record from an array analysis system; wherein receiving the updated reference database comprises receiving the updated reference database via a computer network; and/or any limitation or characteristic disclosed herein alone or in combination.

Disclosed are one or more computer readable media storing program code that, upon execution by one or more computer systems, causes the computer systems to perform any of the methods disclosed herein; and/or any limitation or characteristic disclosed herein alone or in combination.

Also disclosed are computer program products comprising a computer usable memory adapted to be executed to implement any of the methods disclosed herein; and/or any limitation or characteristic disclosed herein alone or in combination.

Disclosed are computer programs and products, comprising a logic processing module, a configuration file processing module, a data organization module, and a data display organization module, that are embodied upon a computer readable medium; and/or any limitation or characteristic disclosed herein alone or in combination.

Also disclosed are computer program products, comprising a computer usable medium having a computer readable program code embodied therein, said computer readable program code adapted to be executed to implement a method for generating the unsupervised classification of claim 31, said method further comprising: providing a system, wherein the system comprises distinct software modules, and wherein the distinct software modules comprise a logic processing module, a configuration file processing module, a data organization module, and a data display organization module; and/or any limitation or characteristic disclosed herein alone or in combination.

Disclosed are methods further comprising a computerized system configured for performing the method; and/or any limitation or characteristic disclosed herein alone or in combination.

Also disclosed are methods further comprising the outputting of the results from the unsupervised classification; and/or any limitation or characteristic disclosed herein alone or in combination.

Also disclosed are computer-readable media having stored thereon instructions that, when executed on a programmed processor perform any of the methods disclosed herein; and/or any limitation or characteristic disclosed herein alone or in combination.

Disclosed are unsupervised classification systems, the systems comprising: a data store capable of storing cell datasets; a system processor comprising one or more processing elements, the one or more processing elements programmed or adapted to: receive cell datasets; store the cell datasets in the data store as a reference database; update the reference database with a dataset from an unknown cell, perform unsupervised classification on the updated reference database; and output a computed label classification of the updated reference database based upon the comparison of the cell datasets within the updated reference database; and/or any limitation or characteristic disclosed herein alone or in combination.

Also disclosed are systems, wherein the system receives the cell datasets from a computer readable media; wherein the system receives the cell datasets via a computer network; further comprising a cell characteristic analysis system; and/or any limitation or characteristic disclosed herein alone or in combination.

D. Computer Readable Media, Computer Program Product, Processors

Computer Usable Memory, Computer Systems

In some embodiments, instructions stored on one or more computer readable media that, when executed by a system processor, cause the system processor to perform the methods described above, and in greater detail below. Further, some embodiments may include systems implementing such methods in hardware and/or software. A typical system may include a system processor comprising one or more processing elements in communication with a system data store (SDS) comprising one or more storage elements. The system processor may be programmed and/or adapted to perform the functionality described herein. The system may include one or more input devices for receiving input from users and/or software applications. The system may include one or more output devices for presenting output to users and/or software applications. In some embodiments, the output devices may include a monitor capable of displaying to a user graphical representation of the described analytic functionality.

The described functionality may be supported using a computer including a suitable system processor including one or more processing elements such as a CELERON, PENTIUM, XEON, CORE 2 DUO or CORE 2 QUAD class microprocessor (Intel Corp., Santa Clara, Calif.) or SEMPRON, PHENOM, OPTERON, ATHLON X2 or ATHLON 64 X2 (AMD Corp., Sunnyvale, Calif.), although other general purpose processors could be used. In some embodiments, the functionality, as further described below, may be distributed across multiple processing elements. The term processing element may refer to (1) a process running on a particular piece, or across particular pieces, of hardware, (2) a particular piece of hardware, or either (1) or (2) as the context allows. Some implementations can include one or more limited special purpose processors such as a digital signal processor (DSP), application specific integrated circuits (ASIC) or a field programmable gate arrays (FPGA). Further, some implementations can use combinations of general purpose and special purpose processors.

The environment further includes a SDS that could include a variety of primary and secondary storage elements. In one preferred implementation, the SDS would include registers and RAM as part of the primary storage. The primary storage may in some implementations include other forms of memory such as cache memory, non-volatile memory (e.g., FLASH, ROM, EPROM, etc.), etc. The SDS may also include secondary storage including single, multiple and/or varied servers and storage elements. For example, the SDS may use internal storage devices connected to the system processor. In implementations where a single processing element supports all of the functionality a local hard disk drive may serve as the secondary storage of the SDS, and a disk operating system executing on such a single processing element may act as a data server receiving and servicing data requests.

It will be understood by those skilled in the art that the different information used in the systems and methods for respiratory analysis as disclosed herein may be logically or physically segregated within a single device serving as secondary storage for the SDS; multiple related data stores accessible through a unified management system, which together serve as the SDS; or multiple independent data stores individually accessible through disparate management systems, which may in some implementations be collectively viewed as the SDS. The various storage elements that comprise the physical architecture of the SDS may be centrally located or distributed across a variety of diverse locations.

In addition, or instead, the functionality and approaches discussed above, or portions thereof, can be embodied in instructions executable by a computer, where such instructions are stored in and/or on one or more computer readable storage media. Such media can include primary storage and/or secondary storage integrated with and/or within the computer such as RAM and/or a magnetic disk, and/or separable from the computer such as on a solid state device or removable magnetic or optical disk. The media can use any technology as would be known to those skilled in the art, including, without limitation, ROM, RAM, magnetic, optical, paper, and/or solid state media technology.

Disclosed herein are machines, apparati, and systems, which are designed to perform the various methods disclosed herein. It is understood that these can be multipurpose machines having modules and/or components dedicated to the performance of the disclosed methods. For example, a computer can be modified as described herein so that it contains a module and/or component which for example, a) produces an updated reference database, which identifies one or more clusters, identifies one or more cell computed definition, and/or performs an unsupervised classification, such as an unsupervised classification alone or in any combination.

Thus, the methods and systems herein can have the data, in any form uploaded by a person operating a device capable of performing the methods disclosed herein. The methods can also be associated with the computer as described herein, either incorporated into these systems or being on device which is connected to them.

E. Examples

1. Example 1

Cultured cell populations are traditionally classified as having the qualities of stem cells by their expression of immunocytochemical or PCR markers (Carpenter et al. Cloning Stem Cells 5:79-88). This approach can often be misleading if these markers are used to categorize novel stem cell preparations or predict inherent multipotent or pluripotent features. To develop a more robust classification system, a framework for identifying putative novel stem cell preparations by their whole-genome messenger RNA expression phenotypes was created (FIG. 1). The core reference data set, 'stem cell matrix', includes cultures of human cells that have been reported to have either stem cell or progenitor qualities, including human embryonic stem cells, mesenchymal stem cells and neural stem cells. To provide the context in which to place the stem cells, non-stem cell samples such as fibroblasts and differentiated embryonic stem cell derivatives were included. To avoid biasing the classification methods, terminology that carried as little preconception about their identity as possible was used. The nomenclature ('source code') has two components: the first is the tissue or cultured cell line of origin. The second term captures a description of the culture itself. Tables 1-8 summarize the descriptions of the core samples and their assigned source codes.

TABLE 1

| Contributors nomenclature | SourceCode | | | |
|---|---|---|---|---|
| | Term 1 | Term 2 | % | |
| Embryonic Stem Cells Undifferentiated | ePSC | UN | 13% | ||||||||||||||||| 20 |
| Embryonic Stem Cell derived Neural Stem Cells | ePSC | Nlin | 21% | |||||||||||||||||||||||||||||| 32 |
| Embryonic Stem Cell derived Extraembryonic Endodermal Lineage | ePSC | XE | 1% | || 2 |
| Embryoid Bodies | ePSC | EB | 4% | |||||| 6 |
| Teratocarcinoma Cells Undifferentiated | tPSC | UN | 1% | | 1 |
| Teratocarcinoma Cells Differentiated into Dopaminergic Neural Lineage | tPSC | Nlin | 12% | ||||||||||||||||| 19 |
| Fetal Neural Stem Cell Line | B | Nlin | 7% | |||||||| 10 |
| Primary Fetal Neural Precursor Cells | B | Nlin | 3% | |||| 4 |
| Fetal glial restr. Progenitors | B | Nlin | 1% | || 2 |
| Fetal astrocyte precursors | B | Nlin | 2% | ||| 3 |
| Adult Neural Precursor, surgery (HANSE) | B | Nlin | 21% | |||||||||||||||||||||||||||||| 32 |

TABLE 1-continued

|  | SourceCode | | |
|---|---|---|---|
| Contributors nomenclature | Term 1 | Term 2 | % |
| Postmortem Neural Precursors | B | Nlin | 4% ‖‖‖ 6 |
| Astrocytes, surgery | B | AS | 1% ‖ 2 |
| Postmortem Astrocytes | B | AS | 1% ‖ 2 |
| Bone Marrow Mesenchymal Stem Cells | BM | Mlin | 4% ‖‖‖ 6 |
| Feeder Fibroblasts | CT | Fib | 4% ‖‖‖ 6 |
|  |  |  | 100% 153 Number Arrays/Samples |

The input samples were categorized according to the descriptive name (contributor's nomenclature) of the cell type based on classical criteria (origin, culture methods, and markers). The Source Code is a labeling structure for the nomenclature: Term 1 indicates the source tissue or cell type (ePSC: embryonic stem cell; tPSC; teratocarcinoma cell lines, iPSC; induced pluripotent stem cell B: brain, BM: bone marrow, CT: connective tissue). Term 2 is a descriptor of the differentiated state or lineage of the cells. (UN: undifferentiated, NLin: neural lineage, XE: extraembryonic endodermal lineage, AS: astrocyte, MLin: mesenchymal lineage, Fib: fibroblastic cell). The percentage is the fraction of the total samples represented by that cell type, and the histogram shows the number of microarrays/samples of each input cell type.

TABLE 2

| Source | Code 1 | Source | Code 2 |
|---|---|---|---|
| Embryonic stem cell line | ePSC | Not differentiated | UN |
| Germ cell tumor stem cell line | ePSC | Neural lineage | NLin |
| Induced pluripotent stem cell line | iPSC | Astrocytic lineage | AS |
| Brain | B | Fibroblasts | Fib |
| Bone marrow | BM | Mesenchymal lineage | MLin |
| Umbilical cord | UC | Extraembryonic endodermal lineage | XE |
| Connective tissue | CT | | |
|  |  | Embroid bodies | EB |
|  |  | Endothelial cell | EC |

To create a nomenclature (Source Code) that makes as few assumptions as possible about the identity of the cells before they were analyzed, a simple system that designates the source of the sample was used (ESC line→embryonic pluripotent stem cell, ePSC, teratocarcinoma or germ cell tumor line→tumor-derived pluripotent stem cell, tPSC, induced pluripotent stem cell lien→iPSC, brain→B, bone marrow→BM, connective tissue→CT) and the presumed derived phenotype of the cells (undifferentiated→UN (for ESC), neural lineage→NLin, extraembryonic endoderm lineage→XE, astrocytes→A, fibroblasts→Fib). For a detailed overview see Tables 3-8.

TABLE 3

| ePSC-Line Code | ePSC-Line (NIH Code) | ePSC line published |
|---|---|---|
| ePSC1 | H9 (WA09) | Thomson et al. Science, 1998 |
| ePSC2 | BG03 (hESBGN-03) | Brimble et al. Stem Cells Dev 2004 |
| ePSC3 | hES1 | Mandel et al. Differentiation 2006 |
| ePSC4 | BG01 (hESBGN-01) | Brimble et al. Stem Cells Dev 2004 |
| ePSC4v | BG01 (hESBGN-01v) | Brimble et al. Stem Cells Dev 2004; Plaia et al. Stem Cells 2006 |
| ePSC5 | Miz-hES5 | Son et al. Stem Cells 2005 |
| ePSC6 | Miz-hES4 | Son et at. Stem Cells 2005 |

TABLE 3-continued

| ePSC-Line Code | ePSC-Line (NIH Code) | ePSC line published |
|---|---|---|
| ePSC7 | Miz-hES6 | Son et al. Stem Cells 2005; Yoo et al. Exp Mol Med 2005 |
| ePSC8 | Hues13 | Cowan et al. NEJM 2004 |
| ePSC9 | Hues7 | Cowan et al. NEJM 2004 |
| ePSC10 | HES1 (ES01) | Reubinoff et al. Nat Biotech 2000; Richards et al. Nat Biotech 2002 |
| ePSC11 | I6 (TE06) | Amit et al. J Anat 2002 |
| ePSC12 | HES3 (ES03) | Reubinoff et al. Nat Biotech 2000 |
| ePSC13 | SNUhES-16 | Unpublished; Xie et al. Nature 2005 |
| ePSC14 | BG02 (hESBGN-02) | Brimble et al. Stem Cells Dev 2004 |
| ePSC15 | HSF-6 (UC06) | Son et al. Stem Cells 2005 |
| ePSC16 | H1 (WA01) | Thomson et al. Science 1998 |
| ePSC17 | H7 (WA07) | Thomson et al. Science 1998 |
| ePSC18 | Hues9 | Cowan et al. NEJM 2004 |
| ePSC19 | Hues20 | Cowan et al. NEJM 2004 |
| ePSC20 | Hues21 | Cowan et al. NEJM 2004 |
| ePSC21 | Hues22 | Cowan et al. NEJM 2004 |
| ePSC22 | Hues22 | Cowan et al. NEJM 2004 |
| ePSC23 | CyT25 | Hoffman et al. Stem Cells 2005 |
| ePSC24 | Hu DM3 | Not published |
| ePSC25 | Hu-J3 (TE07) | Amit et al. J Anat 2002 |
| ePSC26 | Hu-J6 | Amit et al. J Anat 2002 |
| ePSC27 | HES2 (ES02) | Ruebinoff et al. Nat Biotech 2000; Richards et al. Nat Biotech 2002 |
| ePSC28 | HES4 (ES04) | Ruebinoff et al. Nat Biotech 2000; Richards et al. Nat Biotech 2002 | ePSC, embryonic pluripotent stem cell line;
for abbreviations and acronyms of specific cell lines, please refer to the original publications.

TABLE 4

| Cell line code | Cell line | Method/Line published |
|---|---|---|
| tPSC1 | NTera2 | Andrews et al. Lab Invest 1984; Schwartz et al. Stem cells Dev 2005 |
| tPSC2 | 2102Ep | Andrews et al. Int J Cancer 1982; Josephson et al. Stem Cells 2007 |
| tPSC3 | GCT-72 | Pera et al. Cancer Res 1987 |
| tPSC4 | GCT-27X | Pera et al. Differentiation 1989 |
| tPSC5 | GCT-C4 | Pera et al. Int J Cancer 1987 | ePSC, embryonic pluripotent stem cell line;
for abbreviations and acronyms of specific cell lines, please refer to the original publications.

TABLE 5

| Cell line code | Cell line | Method/Line published |
|---|---|---|
| iPSC1 | BJ1-iPS12 | Park et al. Nature 2008 |
| iPSC2 | MSC-iPS1p | Park et al nature 2008 |
| iPSC3 | hFIB2-iPS5 | Park et al. nature 2008 | iPSC, induced pluripotent stem cell line;
for abbreviations and acronyms of specific cell lines, please refer to the original publications.

TABLE 6

| Tissue Code | Tissue source | Following protocol/method/line published |
|---|---|---|
| B | fetal brain | Imitola et al. PNAS 2004; Liu et al. Dev Biol 2004; Bibikova et al. Genome Res 2006 |
| | postmortem brain | Palmer et al. Nature 2001; Schwartz et al. J Neurosci Res 2003 |
| | adult brain | Palmer et al. Nature 2001; Schwartz et al. J Neurosci Res 2003 |
| BM | bone marrow | Bibikova et al. Genome Res 2006; Smith et al. Stem Cells 2004 |
| CT1 | connective tissue | Liu et al. BMC Dev Biol 2006 |
| CT2 | connective tissue | Fibroblasts prepared from skin biopsy specimens taken from postmortem patients enrolled in the NHNSCR protocols (www.nhnscr.org) according to standard procedures: (Sly et al. Methods Enzymol 1979) |
| UC | umbilical cord | Jaffe et al. J Clin Invest 1973 |

TABLE 7

| differentiated cell type code | putative cell type in vitro | Following protocol/method/line published |
|---|---|---|
| UN | undifferentiated | See protocol in cited publication on undifferentiated cell line |
| EB | embryoid body | Martin et al. PNAS 1975 |
| NLin1 | neural lineage | Itsykson 2005 |
| NLin2 | neural lineage | Shin et al. Neuordegener Dis 2006 |
| NLin3 | neural lineage | R. Gonzales, BMIR, unpublished |
| NLin4 | neural lineage | Reubinoff et al. Nat Biotech 2001; Ben-Hur et al. Stem Cells 2004 |
| NLin5 | neural lineage | Moon Lab, unpublished |
| NLin6 | neural lineage | Shin and Rao, unpublished method |
| NLin7 | neural lineage | Shin and Rao, unpublished method |
| NLin8 | neural lineage | Shin and Rao, unpublished method |
| NLin9 | dopaminergic neural lineage | Schwartz et al. Stem Cells Dev 2005 |
| XE | extra embryonic endoderm | Rodolpho Gonzales, in press |

TABLE 8

| derived cell type code | putative cell type in vitro | Following protocol/method/line published |
|---|---|---|
| AS | astrocytes | In-house samples taken from post-mortem patients enrolled in the NHNSCR protocols (www.nhnscr.org) using methods described in [108] |
| Fib | fibroblasts | Liu et al. BMC Dev Biol 2006; Sly et al. Methods Enzymol 1979 |
| ELin | endothelial lineage | Jaffe et al. J Clin invest 1973 |
| NLin10 | neural lineage | Sciencell, (Liu 2004), United States Patent 20050214940, Bibikova et al. Genome Res 2006 |
| NLin11 | neural lineage | Imitola et al. PNAS 2004; Sidman et al. Brain Res 2007 |
| NLin12 | neural lineage | White et al. Cell Transplant 1999, U.S. Pat. No. 7,041,283 |
| NLin13 | neural lineage | Sciencell(Liu et al. Dev Biol 2004), United States Patent 20050214940 |
| NLin14 | neural lineage | Windrem et al. Nat Med 2004 |
| NLin15 | neural lineage | Palmer et al. Nature 2001; Schwartz J Neurosci Res 2003 |
| MC | mesenchymal cell | CD105+, CD34− MSCs prepared from in-house bone marrow specimens harvested from patients enrolled in the NHNSCR protocols (www.nhnscr.org) and prepared according to Bibikova et al. Genome Res 2006; Smith et al. Stem Cells 2004 |

Figure 2A:
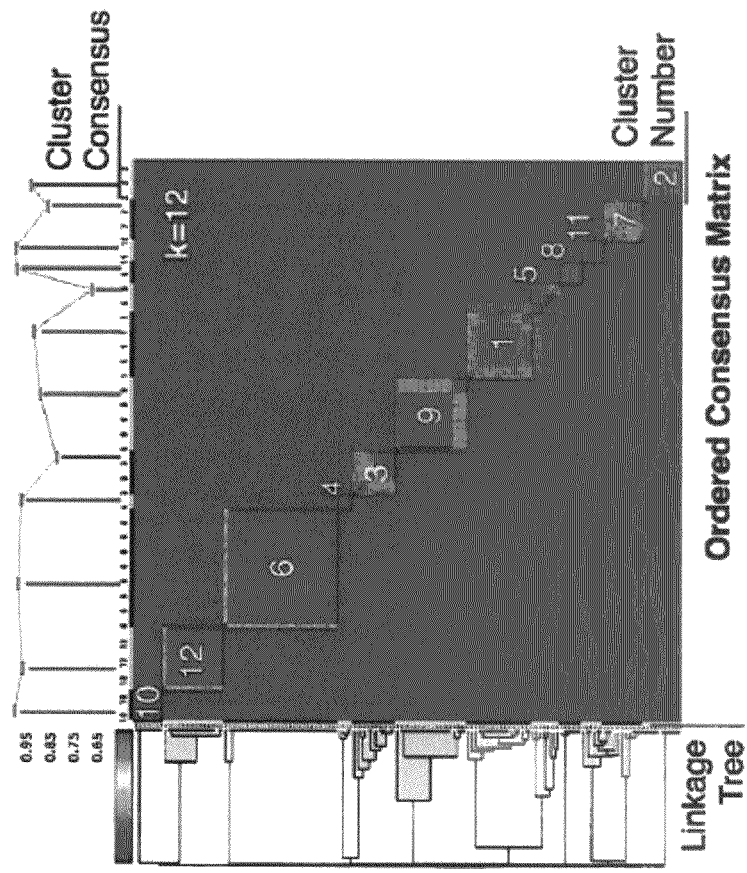
FIG. 2 identifies clusters of samples based on machine learning algorithm. Samples were distributed on the basis of their transcriptional profiles into consensus clusters using sNMF. a, Consensus matrix from consensus clustering results (centre matrix plot). The consensus matrix is a visual representation of the clustering results and the separation of the sample clusters from each other. Blue indicates no consensus; red indicates very high consensus. The numbers (1-12) on the diagonal row of clusters indicate the number assigned to the cluster by sNMF. These numbers (cluster 1 to cluster 12) are used throughout the text to indicate the group of samples in that cluster. The bar graph above the consensus matrix plot shows the summary statistics assessing the overall quality of each cluster. The cluster consensus value (0-1) is plotted above the corresponding cluster in the matrix plot. Note that most clusters (clusters 10, 12, 6, 4, 9, 1, 8, 11, 7 and 2) have a high-quality measurement. To the left of the consensus matrix is another view of the consensus data, visualized as a dendrogram. This is a representation of the hierarchical clustering tree of the consensus matrix. b, The content of the sample clusters resulting from the same sNMF run are displayed. Numbers are the same cluster numbers assigned by the consensus clustering algorithm that are used throughout the text and figures. For more information on samples, source code and references see Tables 1-10. No., number of samples. The symbol '¶' indicates that samples were derived from adult brain specimens.
Figure 2B:
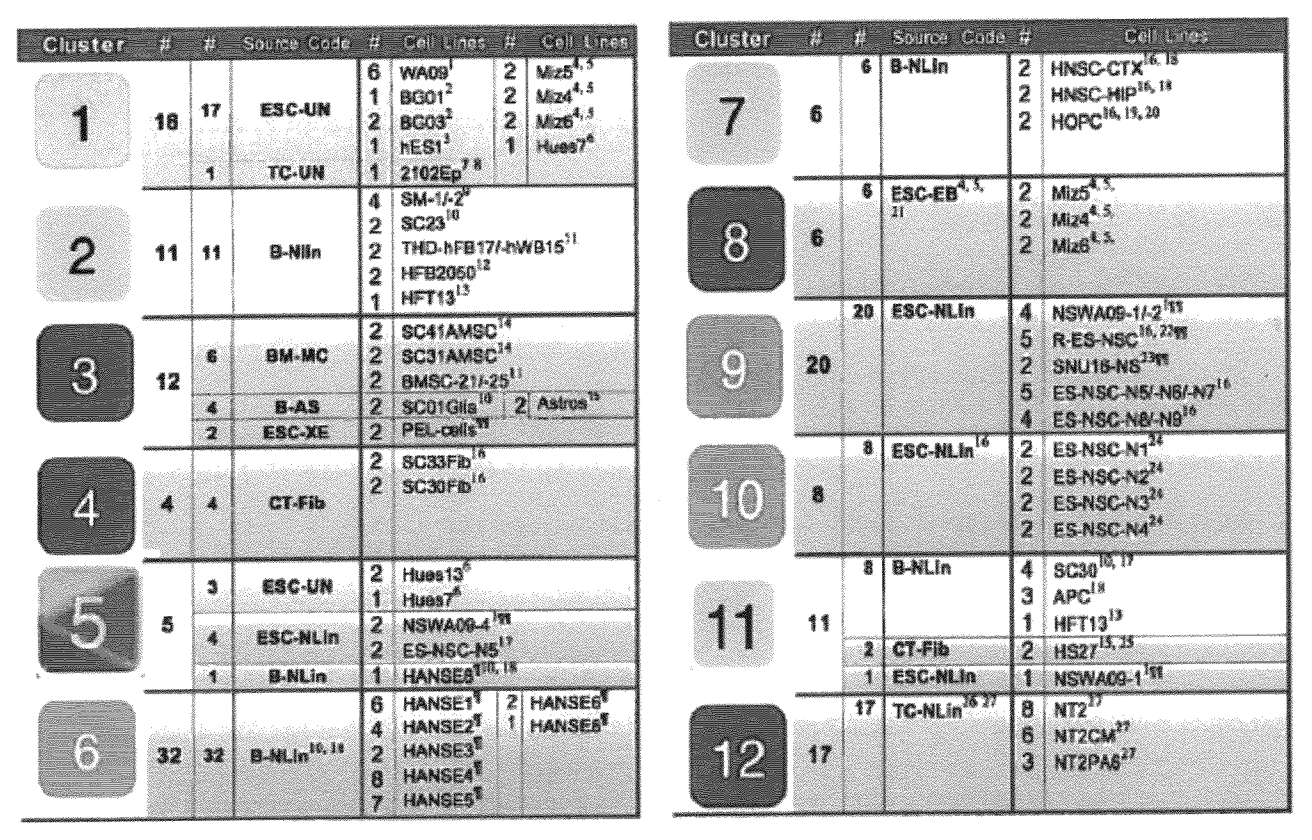
Figure 3:
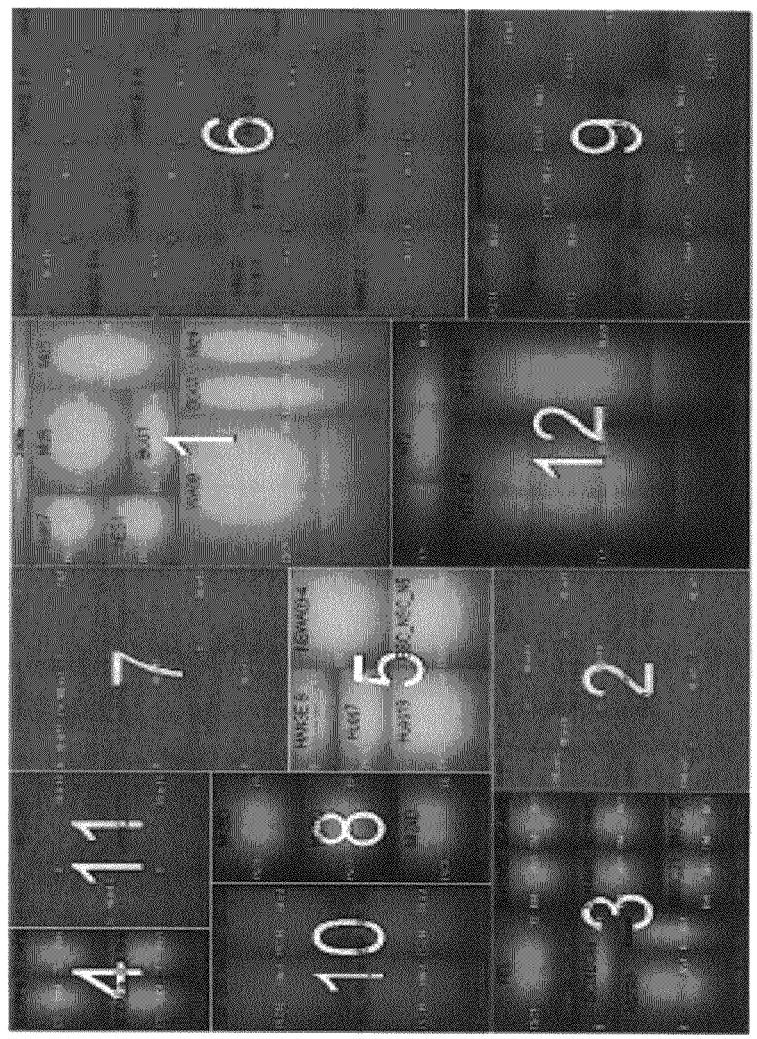
FIG. 3 displays the clustering results as a TreeMap visualization using k=12 sNMF. A TreeMap is a visualization tool that illustrates complex relationships between categories of objects. The dendrogram view that is often used to illustrate hierarchical clustering of microarray data is a visualization metaphor that predates genomics, and has been used for decades to represent phylogenetic trees or cladograms, and genealogical relationships. Because of this historical context, using dendrograms for microarray data can be confusing in some situations. For example, when the data was examined from a variety of stem cell preparations, including a large number of different cell lines, but also including the differentiated derivatives of some of the individual cell lines, the dendrograms can be wrongly inferred to illustrate relationships (such as between a stem cell line and its progeny) that are not intended. The TreeMap shown here illustrates the sample clusters from the k12 sNMF run (see FIG. 1 and Table 14). Each tile represents a sample, and each occupies the same area; the length and width of tiles are adjusted with the squarifying TreeMap algorithm to ensure a space efficient representation of the 153 samples. Numbers denote the Cluster Numbers used throughout the figures and text. Sample names are displayed on the center top of tiles of the same name, and the putative stem cell class is displayed on the bottom center of homonymous samples. The color code relates to the Source Code (see also FIG. 2, and FIG. 6) for types of input samples in each cluster. The Source Codes of samples with the same name are written on the left and right side of the tiles. For more information on sample and Source Code IDs see Tables 1-8.
Figure 4D:
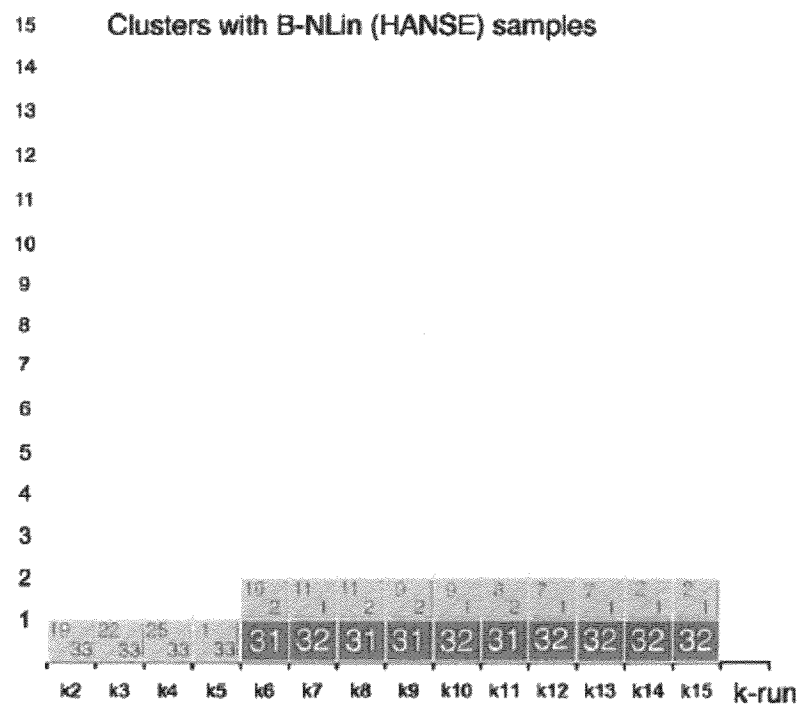

To sort the cell types an unsupervised machine learning approach to cluster transcriptional profiles of the cell preparations into stable distinct groups was used. Sparse non-negative matrix factorization (sNMF) was adjusted for this task by implementing a bootstrapping algorithm to find the most stable groupings, or clusters (Brunet et al. PNAS 101:4164-4169; 2004; Gao et al. Bioinformatics 21:3970-3975, 2005). The stability of the clustering (Monti et al. Mach Learn 52:91-118, 2003) indicated that the data set most likely contained about 12 different types of samples (FIG. 2a). The composition of the stable clusters revealed both predictable and unpredicted groupings of a priori designations (FIG. 2b and FIG. 3). The 20 samples identified as undifferentiated human pluripotent stem cell (PSC) preparations were grouped together in one dominant cluster (FIG. 2, cluster 1) and one secondary cluster (FIG. 2, cluster 5). Sixty-two of the samples were brain-derived cells that were described as neural stem or progenitor cells based on their source, culture methods and classical markers. Most of the designated neural stem cells were distributed among multiple clusters, indicating a great deal of diversity in neural stem cell preparations. But one group of the brain-derived lines, those derived from surgical specimens from living patients (HANSE cells, see below), remained together throughout the iterative clusterings (FIG. 2, cluster 6; see also FIG. 4). The HANSE cell group consisted of transcriptional profiles that were derived from neurosurgical specimens following published protocols for multipotent neural progenitor derivation and propagation (Palmer et al. Nature 411:42-43, 2001; Schwartz et al. J Neurosci Res 74:838-851, 2003). These cells expressed markers that are commonly used to identify neural stem cells (Kornblum et al. Nature Rev Neurosci 2:843-846, 2001) (see FIG. 5), but the clustering clearly separated them from the other samples that had been derived from post-mortem brains of prematurely born infants (SC23 and SC30, see FIG. 2b) (Palmer et al. Nature 411:42-43, 2001; Schwartz et al. J Neurosci Res 74:838-851, 2003).

Sixty six samples comprising new cultures derived from PSC lines that were already in the matrix, preparations that were not yet included (but their presumptive cell type was already represented), or new cell types were added to the data set. Two new types of cells were chosen: a differentiated cell type (umbilical vein endothelial cells (HUVECs)) and a recently developed new source of pluripotent cells called induced pluripotent stem cells (Takahashi et al. Cell 126:663-676, 2006; Takahaski et al. Cell 131: 861-872, 2007; Yu et al. Science 318:1917-1920, 2007; Park et al. Nature 451:141-146, 2008) (iPSCs, Table 9). iPSCs have been generated from somatic cells, including adult fibroblasts, by genetic manipulation of certain transcription factors (Takahaski et al. Cell 126:663-676, 2006; Yu et al. Science 318:1917-1920, 2007;

Park et al. Nature 451:141-146, 2008; Okita et al. Nature 448:313-317, 2007). Clustering results including the test data set (Table 10) were recomputed. All of the HUVEC samples clustered together and formed a distinct group. Most of the additional PSC lines (human embryonic stem cells (embryonic PSCs; ePSCs) and iPSCs) from several different laboratories were placed into a context that contained solely PSC lines. Three additional germ cell tumor lines clustered together with the tumor-derived pluripotent stem cell (tPSC) line 2102Ep and samples of three human embryonic stem (ES) cell lines: BG01 v (Zeng et al. Restor Neurol Neurosci 22:421-428, 2004), Hues7 (Cowan et al. NEJM 350:1353-1356, 2004) and Hues13 (Cowan et al. NEJM 350:1353-1356, 2004). BG01 v is an established aneuploid variant line and the two Hues lines are aneuploid variants of the originally euploid lines (not shown).

Although GSA is valuable for discovering specific differences among sample groups, it is limited to curated gene lists and cannot be used to discover new regulatory networks. The MATISSE algorithm (Ulitsky et al. BMC Syst Biol 1:8, 2007) (http://acgt.cs.tau.ac.il/matisse) takes predefined protein-protein interactions (for example, from yeast two-hybrid screens) and seeks connected subnetworks that manifest high similarity in sample subsets. The modified version used in this analysis is capable of extracting subnetworks that are co-expressed in many samples but also significantly upregulated or downregulated in a specific sample cluster.

Because the PSC preparations were consistently clustered together MATISSE was used to look for distinctive molecular networks that might be associated with the unique PSC qualities of pluripotency and self-renewal. A Nanog-associated regulatory network has been outlined in mouse embryonic

TABLE 9

| Number Arrays | | % | Contributors nomenclature | SourceCode 1&2 | % | | Number Arrays |
|---|---|---|---|---|---|---|---|
| 22 ‖‖‖‖‖‖‖‖‖‖‖‖‖‖‖‖‖‖‖‖‖‖ | | 33% | ESC undifferentiated | ePSC UN | 10% | ‖‖‖‖‖‖‖‖‖‖‖‖‖‖‖‖‖‖‖‖‖‖ | 22 |
| 3 ‖‖ | | 5% | iPS undifferentiated | iPSC UN | 1% | ‖‖ | 3 |
| 7 ‖‖‖‖‖‖‖ | | 11% | Teratocarcinoma cells | tPSC UN | 3% | ‖‖‖‖‖‖‖ | 7 |
| 6 ‖‖‖‖‖ | | 9% | HUVEC | UC ELin | 3% | ‖‖‖‖‖ | 6 |
| 3 ‖‖ | | 5% | Feeder Fibroblasts | CT Fib | 1% | ‖‖ | 3 |
| 8 ‖‖‖‖‖‖‖‖ | | 12% | Fetal NSC cell line | B NLin | 5% | ‖‖‖‖‖‖‖‖‖‖ | 10 |
| 2 ‖ | | 3% | Fetal NPC, primary | | | | |
| 2 ‖ | | 3% | Postmortem Astrocytes | B AS | 1% | ‖ | 2 |
| 4 ‖‖‖ | | 6% | Mesenchymal Stem Cells | BM Mlin | 2% | ‖‖‖ | 4 |
| 3 ‖‖ | | 5% | Primitive Endodermal Cells | ePSC XE | 1% | ‖‖ | 3 |
| 66 | | 100% | | | 100% | | 153 + 66 |
| | | % of Test Dataset | | | % in Minimal Matrix plus Test Dataset | | |

Sixty six samples not included in the 153-sample core dataset (see Table 1) were used to validate the utility of this approach in classifying new cell types. A Source Code scheme similar to that used for the main dataset was used. The test dataset contains several undifferentiated ePSC lines (WA01, WA09, HSF6, Hues9, Hues20, Hues21, Hues22, Cyt25, Cyt203, BG01v, BG02, BG03, HES2, HES3, HES4, J3, J6). The WA09, BG02, and BG03 samples were new examples of the cell line that was included in the core dataset, and the other lines were not represented by samples in the core dataset. Also included were 7 samples from five different germ tumor cell lines, which had been previously reported to have pluripotent features (tPSC: Ntera2, 2102Ep, GCT-C4, GCT-27X, GCT-72). Also included were six preparations of human umbilical vein endothelial cells (HUVEC) from three individuals and three samples from three induced pluripotent stem cell lines (BJ1-iPS12, MSC-iPS1, hFib2-iPS5) in order to test how two novel (supposedly not yet represented) cell types performs within the contextual environment provided by the core dataset and bootstrap sparse NMF. For references regarding the specific cell lines, please see Tables 1-8.

A combination of analysis tools was used to explore the basis of the unsupervised classification of the samples in the core data set. Gene Set Analysis (GSA) (Efron et al. Ann Appl Stat 1:107-129, 2007) is a means to identify the underlying themes in transcriptional data in terms of their biological relevance.

GSA uses lists of genes (Efron et al. Ann Appl Stat 1:107-129, 2007) that are related in some way; the common criterion is that the relationships among the genes in the lists are supported by empirical evidence (Efron et al. Ann Appl Stat 1:107-129, 2007). GSA highlighted numerous significant differences among the computationally defined categories. (FIG. 6, and http://www.stemcellmatrix.org).

PSCs (Wang et al. Nature 444:364-368, 2006), and the elements of this network in human PSCs were identified using an unbiased algorithm. The algorithm predicts that human PSCs possess a similar NANOG-linked network (FIG. 7A; elements labeled in red). However, the human NANOG network seems to be integrated as a small component of a much larger protein-protein interaction network that is upregulated in human PSCs (FIG. 7). Notably, this PSC-specific network (termed pluripotency-associated network, PluriNet) contains key regulators that are involved in the control of cell cycle, DNA replication; DNA repair, DNA methylation, SUMOylation, RNA processing, histone modification and nucleosome positioning (see also http://www.openstemcellwiki.org). Many of the genes in the PluriNet have been linked to embryogenesis, tumorigenesis and ageing (FIG. 7C and FIG. 8). Pluripotency is closely linked to PluriNet expression by analyzing published gene expression data sets from human oocytes, various types of PSCs and murine embryos (see Table 10 for a summary of findings in various model systems). Analysis of a microarray data set (Wange et al. Dev Cell 6:133-144, 2004) that spans development from murine oocytes to the late blastocyst stage revealed that the PluriNet expression is dynamic and upregulated during early mammalian embryogenesis (Table 10 and FIGS. 9-11) (Chambers et al. Nature 450:1230-1234, 2007). Also, preliminary analyses indicate that the PluriNet is strongly upregulated in mouse PSCs, mouse iPSCs and mouse epiblast-derived stem cells (Tesar et al. Nature 448:196-199, 2007) when compared to somatic cells. Therefore the PluriNet can be useful as a biologically inspired gauge for classifying both murine and human PSC phenotypes (Table 10 and FIGS. 12-14.

TABLE 10

PluriNet expression patterns in various model systems for pluri-potency a. Expression of PluriNet genes in murine model systems

| Cell type | Upregulated/downregulated |
|---|---|
| MII oocytes | Upregulated* |
| Zygote | Upregulated* |
| Embryo (two-cell blastocyst) | Upregulated* |
| ePCS | Upregulated† |
| EpiSC | Upregulated† |
| Fibroblasts (normal) | Downregulated† |
| Fibroblasts (transformed) | Downregulated† | b. Successful PluriNet-based, post-hoc classification in murine model systems

| Cell type | Upregulated/downregulated | Pluripotency (PAM) | Germline transmission (PAM) |
|---|---|---|---|
| ePSC | Upregulated | Yes‡ | Yes‡ |
| EpiSC | Upregulated | Yes‡ | Yes‡ |
| iPSC | Upregulated | Yes‡ | Yes‡ |
| Fibroblasts (normal) | Downregulated | Yes‡ | Yes‡ |
| Fibroblasts (transformed) | Downregulated | Yes‡ | Yes‡ | c. Expression of PluriNet genes in human model systems

| Cell type | Upregulated/downregulated |
|---|---|
| MII oocytes | Upregulated§ |
| tPSC | Upregulated\|\| |
| ePSC | Upregulated\|\| |
| iPSC | Upregulated\|\| |
| ePSC-derived cell types | Downregulated\|\| |
| Somatic cell types | Downregulated\|\| |
| Somatic cancer cell line (HeLa) | Downregulated# | d. Successful PlurNet-based, post-hoc classification in human model systems

| Cell type | Upregulated/downregulated | Pluripotency (PAM) |
|---|---|---|
| tPSC | Upregulated | Yes** |
| ePSC | Upregulated | Yes** |
| iPCS | Upregulated | Yes** |
| ePSC-derived cell types | Downregulated | Yes** |
| Somatic cell types | Downregulated | Yes** |

*For more details see FIG. 10 and 11.
†For more details see FIG. 12.
‡For more details see FIG. 12.
§For more details see FIG. 9.
\|\|For more details see FIG. 7B and FIG. 14.
¶For more details see FIG.13.
For more details see Example 2 below.
**For more details see FIG. 14.

This table summarizes the expression patterns of PluriNet in various model systems of pluripotency and differentiation. More details on the specific tests and explanations of the data sources for the results can be found as indicated below. EpiSC, epiblast-derived stem cells (Tesar et al. Nature 448: 196-9, 2007); PAM, prediction analysis of microarray, classifier with leave-one-out cross validation (Lacayo et al. Blood 104:2646-54, 2004), 'Yes' in parts b and d indicates correct classification of pluripotent state (pluripotent or not pluripotent) in >90% of samples.

FIG. 9 shows a significant presence of nearly all genes from PluriNet in the transcriptome of human oocytes, as well as a significant and marked up-regulation of most of these genes in these cells as compared to somatic tissues and cell types.

Oocytes are derived from germ cell precursors and are thought to be the progeny of pluripotent precursors that are set aside during development before somatic tissue differentiation. Primordial germ cells undergo mitotic proliferation followed by meiosis. By the time the oocyte reaches the MII stage, it represents a unique cell type which has the potential to reprogram the sperm nucleus and to induce totipotency in the diploid zygote. This ability appears to be conserved between both ePSC and oocytes since both cell types share the capacity to reprogram a somatic nuclei and confer pluripotent-like features in mammals (Tada et al. Curr Biol 11:1553-8, 2001; Byrne et al. Curr Biol 13:1206-13, 2003; Cowan et al. Science 309:1369-73, 2005).

It has been demonstrated by others that murine ePSC can be differentiated into primordial germ cells, which then can give rise to oocyte-like, and sperm-like cells (Hubner et al. Science 300:1251-6, 2003; Kehler et al. Semin Reprod Med 23, 222-33, 2005; West et al. Nat Protocol 1:2026-36, 2006; Geijsen et al. Nature 427:148-54, 2004).

It has been proposed that a common set of genes in oocytes and ePSC can be responsible for reprogramming somatic nuclei, pluripotency and germ-line transmission (Kocabas et al. PNAS 103:14027-32, 2006). Interestingly, PluriNet is highly enriched for genes that have been functionally linked to the cell cycle in various experimental systems and species ranging from yeasts to humans. Surprisingly, MII oocytes, which are by their very nature and identity in Meiosis II and are not progressing through the cell cycle, do express almost all genes from the network that was defined as PluriNet.

Notably is the absence of NANOG (yellow marked node in Panel B) in human oocytes as assessed by microarray hybridization. This is in line with studies in other mammals, where NANOG appears to stabilize self-renewal and pluripotency, but is only essential to germ cell development (Chambers et al. Nature 450:1230-4, 2007). The presence of this transcription factor in PluriNet but absence in cells poised to become pluripotent and germ-line competent (such as oocytes, cells from the early cleavage stages of embryogenesis or induced pluripotent cells up to 7 days after transfection with Oct4, Sox2, KIf4 and c-myc) (Mitsue et al. Cell 113:631-42, 2003; Hatano et al. Mech Dev 122:67-79, 2005; Wernig et al. Nature, 2007) supports the idea that PluriNet is a comprehensive molecular map of pluripotency that also contains key factors that are dispensable under certain conditions and at certain points in time.

An unbiased global molecular profiling approach combined with a transcriptional phenotype collection using suitable machine learning algorithms can be used to understand and codify the phenotypes of stem cells (Brunet et al. PNAS 101:4164-4169, 2004; Gao et al. Bioinformatics 21:3970-3975, 2005; Golub et al. Science 286:531-537, 1999). The data set and PluriNet have already proved useful for categorizing cell types using unbiased criteria. As more stem cell populations become available, cultured by new methods, isolated from new sources, or induced by new methods, the PluriNet and the stem cell matrix can be used as a reference system for phenotyping the cells and comparing them with existing cell lines.

2. PluriNet and Cell Cycle Regulation

A) Gene Sets from Unbiased Whole Genome Cell Cycle Studies

Two recent studies used RNAi for an unsupervised, genome-wide screen for genes essential for progression through specific cell cycle phases. These landmark studies are the first genome-wide mechanistic dissections of the mammalian cell cycle. Other studies focusing on similar questions by arrest-release paradigms and subsequent microarray analysis have been disputed because of intrinsic experimental problems (Cooper et al. J Theor Biol 249:574-81, 2007; Cooper Trends Biotechnol 22:274-6, 2004).

RNAi was used to knock down in vitro about 25,000 genes and 20,000 genes, respectively, in human cell lines. The morphological patterns of the cells were then tested for evidence of cell cycle phase-specific arrest phenotypes (Mukherji et al. PNAS 103:14819-24, 2006; Kittler et al. Nat Cell Biol 9:1401-12, 2007).

The cell cycle-related genes identified in these studies were mapped to Illumina microarray probes. When analyzing the overlap of the PluriNet genes with all the genes identified as cell cycle-related in the knock-down screens, a small but significant overlap was identified: 13 probes were common to PluriNet and the two other studies, (PluriNet and Kittler et al. 2007: 56 probes, PluriNet and Mukherji et al. 2006: 36 probes, FIG. 15.

Interestingly, only a few genes (represented by 112 probes on Illumina arrays) were in common between the two cell cycle studies. A consistent up- or down-regulation of these independently generated groups of genes in a dataset that consists of an undifferentiated embryonic PSC (ePSC-UN) line and of a cell type that has been used for both of the RNAi screens for cell cycle regulators was checked.

Four cell cycle-specific gene sets (G1/S common, G2 common, G2/M common M/G1 common, 480 genes altogether) were included from a recent paper by Bar-Joseph and colleagues. In this study, the authors had analyzed genome-wide cyclic gene expression patterns (from about 20,000 candidates in karyotypically normal cells) using microarrays and computationally deconvoluted the hybridization signals to "single cell" expression profiles (Bar-Joseph et al. PNAS 105:955-60, 2008).

When looking for overlap between PluriNet and the three studies, a significant, but not dominating overlap was found: 56 genes of the 299 genes from PluriNet are also members of the 480 genes identified by Bar-Joseph (Bar-Joseph et al. PNAS 105:955-60, 2008). The overlap of two of the four gene sets with PluriNet is significant: G1/S common (23 genes, p-value=1.30E-14) and G2/M common (29 genes, p-value=9.15E-17).

All these independently and experimentally gathered gene sets collectively represent more than 2000 genes that have been implicated in cell cycle progression that can be analyzed in light of the topological and expression patterns of PluriNet.

b) Generation of Independent Expression Profiles from ePSC and a Cancer Cell Line Six biological replicates of ePSC-UN samples (line WA09 [H9]) and HeLa-cultures were profiled using Illumina microarrays.

c) Gene Set Enrichment Analysis of Cell Cycle Phases in ePSC-UN and HeLa cells.

Using Gene Set Enrichment Analysis (GSEA) (Subramanian et al. PNAS 102:15545-50, 2005), it was found that, as expected, PluriNet is up-regulated in ePSC relatively to HeLa cells (p-value, FDR, FWER all <0.001). In addition, twelve of the twenty cell cycle phase-specific gene sets were up-regulated in ePSC-UN (see Table 13 below).

The following gene groups from Mukherji 2006 were up-regulated in ePSC-UN: G1-Phase, S-Phase. These findings were supported by the simultaneous up-regulation of the corresponding gene sets as defined by Kittler et al in ePSC-UN: G0/1 arrest, S-arrest. These gene sets from Bar-Joseph were upregulated in ePSC-UN: G2 common, G1/S common.

Interestingly, gene groups from Kittler et al., which one would expect to be equivalent to the G2/M-phase related ones as defined by Mukherji et al. and Bar-Joseph et al. were up-regulated in HeLa cells and not in ePSC-UN: G2 arrest, Cell Division defect.

While some discordance was found between the expression patterns of the phase-specific gene sets from both RNAi studies and the microarray study, a simultaneous up-regulation in ePSC-UN of genes that were found to be essential for (G1/)S-phase progression was found in all three papers (See Tables 11 and 12).

TABLE 11

Gene sets enriched in phenotype ePSC (6 samples, gene set permutation)

| | Gene Set | SIZE | ES | NES | NOM p-val | FDR q-val | FWER p-val |
|---|---|---|---|---|---|---|---|
| 1 | PLURINET | 370 | 0.56 | 1.93 | 0 | 0 | 0 |
| 2 | BAR-JOSEPH CATEGORY G2 COMMON | 23 | 0.66 | 1.51 | 0.035 | 0.04 | 0.066 |
| 3 | MUKHERJI CAT3: S-PHASE | 78 | 0.48 | 1.38 | 0.042 | 0.098 | 0.234 |
| 4 | MUKHERJI CAT6: G2M | 345 | 0.39 | 1.32 | 0.017 | 0.131 | 0.377 |
| 5 | MUKHERJI CELLCYCLE ALL | 1204 | 0.35 | 1.31 | 0 | 0.107 | 0.381 |
| 6 | KITTLER CATEGORY G0/1 ARREST | 797 | 0.33 | 1.21 | 0.019 | 0.202 | 0.689 |
| 7 | MUKHERJI CAT5: G2M LARGE NUCLEUS | 262 | 0.36 | 1.19 | 0.115 | 0.2 | 0.739 |
| 8 | BAR-JOSEPH CAT: G1/S COMMON | 174 | 0.37 | 1.17 | 0.132 | 0.203 | 0.802 |
| 9 | MUKHERJI CAT7 G2M&ENDOREPLICATION | 73 | 0.37 | 1.06 | 0.351 | 0.403 | 0.978 |
| 10 | KITTLER S-ARREST | 253 | 0.32 | 1.05 | 0.326 | 0.399 | 0.985 |
| 11 | MUKHERJI CAT2: G1 | 165 | 0.31 | 0.97 | 0.512 | 0.575 | 1 |
| 12 | MUKHERJI CAT8: G2M = CYTOKINESIS | 42 | 0.33 | 0.84 | 0.707 | 0.865 | 1 |

Abbreviations:
SIZE, number of probes of array per group;
ES, enrichment score;
NES, normalized enrichment score;
NOM p-val, nominal p-value;
FDR q-val, false discovery rate,
FWER q-val, family wise error rate;

TABLE 12

Gene sets enriched in phenotype HeLa (6 samples, gene set permutation)

| | Gene Set | SIZE | ES | NES | NOM p-val | FDR q-val | FWER p-val |
|---|---|---|---|---|---|---|---|
| 1 | BAR-JOSEPH CATEGORY G2/M COMMON | 209 | −0.52 | −1.7 | 0 | 0.009 | 0.011 |
| 2 | BAR-JOSEPH CELL CYCLE ALL | 465 | −0.41 | −1.45 | 0 | 0.058 | 0.124 |
| 3 | BAR-JOSEPH CATEGORY M/G1 COMMON | 59 | −0.5 | −1.38 | 0.054 | 0.077 | 0.232 |
| 4 | KITTLER CELL CYCLE ALL | 1498 | −0.33 | −1.25 | 0 | 0.144 | 0.503 |
| 5 | KITTLER CATEGORY G2 ARREST | 134 | −0.39 | −1.25 | 0.086 | 0.123 | 0.525 |
| 6 | KITTLER CELL DEVISION DEFECT | 315 | −0.35 | −1.22 | 0.041 | 0.121 | 0.585 |
| 7 | MUKHERJI CAT1 G1 SMALL NUCL. AREA | 158 | −0.34 | −1.09 | 0.243 | 0.288 | 0.935 |
| 8 | MUKHERJI CAT4: S G2M | 79 | −0.35 | −1.03 | 0.381 | 0.378 | 0.981 |

Abbreviations:
SIZE, number of probes of array per group;
ES, enrichment score;
NES, normalized enrichment score;
NOM p-val, nominal p-value;
FDR q-val, false discovery rate,
FWER q-val, family wise error rate This is also consistent with the observation that about 60-70% of all PSCs in a culture dish appear to go through S-phase as contrasted by only about 20% of HeLa cells (Fluckiger et al. Stem Cells 24:547-56, 2006; Becker et al. J Cell Physiol 210:517-26, 2007; Becker et al. J Cell Physiol 209:883-93, 2006).

Four of these gene sets received some statistical support (FDR <0.15). Interestingly, the two highest scoring up-regulated gene sets in ePSC (PluriNet and S-Phase) overlapped by only three probes.

Notably, ePSC-UN lines have been reported to have culture doubling times longer than 32 hours (Gearhart NEJM 350:1275-6, 2004) (H9 [WA09] 43 hrs+/−11 hrs) (Ware et al. Stem Cells 24:2677-84, 2006) and HeLa cells cultures do double every 23 hours (Jacobson et al. Tissue Cell 14:69-83, 1982). This suggests that higher replication times are not responsible for the enrichment of cell cycle related genes in PluriNet.

These observations indicate that there is significant but not dominating overlap between PluriNet and certain gene sets that represent cell cycle phases. There is a high up-regulation of PluriNet in ePSC-UN, and to a lesser degree and significance, up-regulation of specific cell cycle phases, especially the ones relating to G1/S-phase progression.

These results could have two interpretations relating to the relationship between PluriNet and the "essential" cell cycle transcriptome: (1) PluriNet and the cell cycle transcriptome are parts of the same molecular program and (2) PluriNet and the cell cycle transcriptome represent two separate biological modules in PSCs with many interactions between them.

d) Post-GSEA Analysis: Leading-Edge Subset Similarity and Clustering

In analyzing the top-scoring gene sets resulting from GSEA, it was determined whether their GSEA enrichment signal derives from a shared subset of genes. Shared subsets could determine whether one should interpret the sets as representatives of independent processes, or if, in fact, they result from the same common mechanism (Efron et al. The Annals of Applied Stats 1:107-129, 2007). The "leading-edge subset" can be interpreted as the core of a gene set that accounts for the GSEA enrichment signal (Subramanian et al. PNAS 102:15545-50, 2005).

When using the "set-to-set leading edge analysis" tool in GSEA, essentially no overlap was found between the signals that were responsible for the statistical enrichment scores of each PluriNet and the cell cycle gene set in GSEA (FIG. 16A)(Subramanian et al. PNAS 102:15545-50, 2005). Only a small signal-overlap score of 0.045 (maximum possible score: 1) between PluriNet and the G1/S common phase gene set from Bar-Joseph 2008 can be detected (FIG. 16B). There is no signal overlap at all among all other gene sets and PluriNet.

This supports the interpretation that PluriNet is a transcriptional module, which is up-regulated independently from cell cycle phase-specific modules in ePSC. Also, if PluriNet (which includes PSC-specific genes like NANOG, POU5F1, and TDGF1 etc.) is up-regulated in PSCs, but not in somatic or cancer cell lines, which undergo cell division, it can be non-essential to cell division in most non-pluripotent cell types.

PluriNet (or at least a major part of it) can function as a distinct module integrated in a larger context that also contains cell cycle specific modules.

These considerations lead to another testable hypothesis: PluriNet was discovered not only because of its expression pattern but also by taking advantage of topological information encoded in the human protein-protein interactome. Thus one should be able to use topological measures to test for possible modularity or dispersion of the "essential", phase-specific cell cycle modules within PluriNet.

Therefore, summary statistics defining the relative position of each cell cycle gene group within PluriNet were looked at. Average distance of each overlapping PluriNet-cell cycle gene set was computed (Table 13).

TABLE 13

Topological analysis of overlap between PluriNet and cell cycle specific gene sets

| Annotation | Set | Average distance between set nodes in PluriNet | Expected average distance | Proximity p-value |
|---|---|---|---|---|
| Bar Joseph '08 cell cycle | G1/S common | 3.423 | 4.137 | 0.0092 |
| Bar Joseph '08 cell cycle | G2 common | 5.000 | 4.150 | 0.7498 |
| Bar Joseph '08 cell cycle | G2/M common | 3.919 | 4.131 | 0.2146 |
| Bar Joseph '08 cell cycle | M/G1 common | 6.000 | 4.130 | 0.8748 |
| Mukheri et al. | G1 | 6.000 | 4.126 | 0.9686 |
| Mukheri et al. | G1 small nuclear area | Overlap <2 genes | | |
| Mukheri et al. | G2M | 3.400 | 4.134 | 0.1248 |
| Mukheri et al. | G2M + endoreplication | Overlap <2 genes | | |
| Mukheri et al. | G2M = cytokinesis | 3.833 | 4.119 | 0.3748 |
| Mukheri et al. | S - phase | 3.333 | 4.139 | 0.2498 |
| Mukheri et al. | S G2M | 2.667 | 4.122 | 0.0623 |
| Kittler et al. | Cell division defect | 4.463 | 4.135 | 0.8162 |
| Kittler et al. | G0/1 arrest | 3.394 | 4.134 | 0.0388 |
| Kittler et al. | G2 arrest | 4.000 | 4.145 | 0.4373 |
| Kittler et al. | S arrest | 3.894 | 4.143 | 0.2966 |
| All Cell Cycle related genes from above in PluriNet | | 4.0041103 | 4.133898 | 0.0949 |

☐ Significant Proximity p-value ≤ 0.05
All p-value were Bonferroni corrected for multiple testing.

In both cases the shared genes are topologically closer than expected. This suggests that the overlapping genes with PluriNet can represent sub-modules in a topological context, thus possibly representing "interfaces" between the general cell cycle machinery and a regulatory machinery for pluripotency, as codified in the study by PluriNet.

Finally, expression trends of PluriNet and the 16 cell cycle modules in a second model system for pluripotency were uncovered. The murine pre-implantation development dataset as described and analyzed in FIGS. 12 and 13 were elected. First corresponding probes for homologues genes on the MG_U74Av2 arrays to the cell cycle-related gene sets as defined by Bar-Joseph et al., Kittler et al. and Mukherjii et al. were identified. For this BioMart MartView was used (http://www.ensembl.org/biomart/martview/). For each of the five developmental sample groups as defined in FIG. 12 a GSEA enrichment score of each gene set was computed as compared to all other remaining samples ("rest"). The normalized enrichment scores were then plotted (NES, Table 14) as a heat map for trend discovery (FIG. 17).

TABLE 14

Normalized Gene Set Enrichment Scores for cell cycle-specific Gene Sets during murine preimplantation development

| GS DETAILS | GV-oocytes | MII oocyte Zygote | 2 Cell | 4-16 cell | Blastocyst |
|---|---|---|---|---|---|
| BAR-JOSEPH G1/S COMMON | −0.38 | 0.42 | 0.24 | 0.28 | −0.34 |
| BAR-JOSEPH G2 COMMON | −0.55 | 0.43 | −0.48 | 0.59 | −0.3 |
| BAR-JOSEPH G2/M COMMON | 0.3 | −0.28 | 0.31 | 0.26 | −0.34 |
| BAR-JOSEPH M/G1 COMMON | −0.46 | 0.39 | 0.35 | 0.27 | −0.43 |
| KITTLER CELL-DIVISION DEFECT | −0.29 | 0.3 | −0.27 | 0.25 | −0.29 |
| KITTLER G0/1 ARREST | −0.3 | −0.27 | −0.38 | 0.32 | 0.28 |
| KITTLER G2 ARREST | 0.35 | −0.48 | −0.5 | 0.42 | 0.37 |
| KITTLER S-ARREST | −0.32 | −0.47 | −0.46 | 0.43 | 0.35 |
| MUKHERJI CAT1 G1 SMALL NUCLEAR AREA | −0.22 | 0.26 | 0.25 | 0.24 | −0.22 |
| MUKHERJI CAT2 G1 | 0.23 | 0.21 | −0.25 | −0.25 | −0.25 |
| MUKHERJI CAT3 S-PHASE | −0.31 | −0.31 | −0.24 | 0.34 | −0.32 |
| MUKHERJI CAT4 S/G2M | 0.32 | 0.34 | −0.5 | −0.29 | 0.26 |
| MUKHERJI CAT5 G2M LARGE NUCLEUS | 0.36 | −0.22 | −0.32 | 0.24 | 0.21 |
| MUKHERJI CAT5 G2M | 0.33 | −0.3 | −0.34 | 0.28 | 0.27 |
| MUKHERJI CAT7 G2M + ENDOREPLICATION | 0.27 | −0.25 | 0.27 | −0.22 | −0.36 |
| MUKHERJI CAT8 G2M + CYTOKINESIS | −0.36 | 0.49 | 0.33 | 0.2 | −0.47 |
| PLURINET | −0.39 | −0.36 | −0.42 | 0.37 | 0.37 |

PluriNet is being up-regulated during murine preimplantation development, with peak values in multi-cell stages and blastocysts. Importantly one has to keep in mind that this is a comparison of all gene sets during development relative to each other. Still, almost all genes contained in PluriNet are significantly expressed in all stages of preimplantation development (for more details see FIGS. 12 and 13).

PluriNet as a gene set has relatively low expression in GV oocytes, MII oocytes, zygotes and the two-cell stage but becomes more and more up-regulated in 4-16 cell stages and blastocysts.

This pattern co-varies with gene sets from Kittler et al. that are associated in human cells with G0/1 and S phase progression. These two specific phases were also up-regulated in human PSCs when compared with HeLa cells, but not to a highly significant degree (see Table 1). This pattern is not mirrored by the other G0/GUS-phase specific gene sets as defined by Bar-Joseph and Mukherji, which appear to peak earlier in development. Of note is the co-upregulation of many G2M-phase-related gene sets in GV oocytes.

As the last step, the overlap between leading-edge subsets from PluriNet and the other gene sets in this developmental dataset were analyzed. The obtained results mirror closely the ones in the human system; the correlated signals for up-regulation of PluriNet and all cell cycle-specific gene sets as detected by GSEA overlap only minimally (FIG. 18) and thus cannot provide alone a straightforward explanation for the close relationship between cell cycle and PluriNet.

To summarize these findings, PluriNet does have a significant but not dominating overlap with gene groups that were experimentally shown to be cell cycle phase-specific. This overlap cannot explain alone significant correlations of differential expression signals as evaluated by gene set enrichment methodologies across different experimental systems. There are some correlations in expression dynamics between some specific gene sets and PluriNet (especially the ones that are S-phase related), but this feature is neither consistently detected in different cell cycle phase models that had been independently used to define cell cycle specific gene sets nor can it be sufficiently explained by overlapping gene set expression patterns.

The results point toward the conjecture that the correlation between PluriNet and cell cycle in general or specific cell phases is not as straightforward as would be necessary to explain PluriNet's features solely by its intra-gene set over-representation of process-specific genes that also have been implicated in cell cycle progression.

Most importantly, this discussion also demonstrates the clear limitations of current methodologies for transposing analyses and results of systems- and genome-wide phenomena, such as cell cycle and pluripotence, in various experimental models. This calls for the future development of more powerful experimental and bio-computational tools for the analysis of large or global effects in functional genomics data.

3. Materials and Methods a) Summary

FIG. 1 provides an overview of the general workflow. A detailed list of the samples, culture methods and reference publications is provided in Supplementary Information (Schwartz et al. J Neurosci Res 74:838-851, 2003). Generally, RNA from each sample was prepared from approximately $1\times10^6$ cultured cells. Sample amplification, labeling and hybridization on Illumina WG8 and WG6 Sentrix Bead-Chips were performed for all arrays in this study according to the manufacturer's instructions (http://www.illumina.com) at a single Illumina BeadStation facility. The Consensus Clustering framework (Monti et al. Mach Learn 52:91-118, 2003) was used to cluster transcription profiles and to assess stability of the results. As the algorithm, sparse non-negative matrix factorization was used. For data perturbation, 30 sub-sampling runs were performed for each considered number of clusters (k). In each run, 80% of the data was subjected to ten random restarts. The R-script can be downloaded at http://www.stemcellmatrix.org. Details on the application of GSA (Efron et al. Ann Appl Stat 1:107-129, 2007), PAM (Lacayo et al. Blood 104:2646-2654, 2004), MATISSE (Ulitsky et al. BMC Syst Biol 1:8, 2007) as well as publicly available data sets used in this study can be found in the Methods section. The MATISSE (Ulitsky et al. BMC Syst Biol 1:8, 2007) computational framework was modified to fit the goals of this study. For the present analysis the human physical interaction network that was previously assembled (Ulitsky et al. BMC Syst Biol 1:8, 2007) and augmented with additional interactions from recent publications was used (Wang et al. Nature 444:364-368, 2006; Ewing et al. Mol Syst Biol 3:89, 2007; Mishra et al. Nucleic Acids Res 34:D411-D414, 2006). The 64 interactions in Wang et al. were mapped to the corresponding human orthologues using the NCBI HomoloGene database (Wang et al. Nature 444:364-368, 2006).

b) Compilation of Type Collection

Each sample was prepared from approximately $1\times10^6$ cultured cells, which were mechanically harvested, pelleted and snap frozen in liquid nitrogen. Biological replicates were produced for almost all samples. Details on the included cell lines and culture methods can be found in the Tables 3-8.

c) Neural Progenitor Cultures (HANSE) from Neurosurgical Specimens.

All brain tissue samples were obtained from patients who underwent surgery for intractable temporal lobe epilepsy at the Department of Neurosurgery, University Medical Center Hamburg-Eppendorf, Germany (n=6; 4 males and 2 females; mean age 33). All procedures were performed with patient informed consent and in accordance with institutional human tissue handling guidelines. During the surgical resection procedure (amygdalohippocampectomy), three types of brain tissue were collected: cortical tissue, the sclerotic hippocampus and the amygdala. These regions were cultured separately and the resulting neural progenitor cultures were termed HANSE (Human Adult Neural Progenitors for Scientific Experimentation) with an additional code letter indicating anatomical origin: C (cortex), H (hippocampus) and A (amygdala). Modifications of reported protocols for establishing neural progenitor cultures from fetal and postmortem brain tissue were used (Palmer et al. Nature 411:42-3, 2001; Schwartz et al. J Neurosci Res 74:838-51, 2003; Imitola et al. PNAS 101:18117-22, 2004). Briefly, the samples were dissected and dissociated to a single-cell suspension by enzymatic digestion using Collagenase/Dispase (Roche, Mannheim, Germany). The filtered cell suspensions were cultured in neurobasal medium (Invitrogen, Carlsbad, Calif.) with B27 supplement (20 ul/ml, Invitrogen), Glutamax (10 ug/ml, Invitrogen) fibroblast growth factor-2 (FGF-2, 20 ng/ml, Peprotech, Rocky Hill, N.J.), epidermal growth factor (EGF, 20 ng/ml, Peprotech), platelet derived growth factor (PDGF, 20 ng/ml, Peprotech), and heparin (32 IE/ml, Ratiopharm, Ulm, Germany). Growth factors and heparin were renewed twice weekly. HANSEs were cultured in uncoated 25-cm² flasks and routinely passaged at confluency. Cells were dissociated either with HBSS-based enzyme free cell dissociation buffer (Invitrogen) or Accutase (Sigma-Aldrich, Hamburg, Germany).

d) RT-PCR of HANSE Preparations:

Total RNA from each HANSE culture at passage 3 was extracted with the RNeasy Mini Kit (Qiagen, Hilden, Germany) and DNAase treated with RNAase-free DNAase I (Qiagen). cDNA first-strand synthesis was performed in a total reaction volume of 100 μl containing 15 pg of total RNA, 100 μM dNTP mix (Invitrogen, Karlsruhe, Germany), 500 ng p(dN)$_6$ random primer (MWG Biotech, Martinsried, Germany) and 1000 U Superscript II Reverse Transcriptase (Invitrogen). 1 μl of the first-strand reaction mixture was subjected to a 20 μl-PCR using 10 μmol of each primer (MWG Biotech, Martinsried, Germany) and 0.5 U Taq DNA polymerase (Qiagen). Reaction conditions were as follows: initial denaturing 95° C./3 min, denaturing 95° C./30 s, annealing 45 s at appropriate temperature, elongation 72° C./45 s for 35 cycles, final elongation 72° C./5 min.

Primer sequences, length of fragment and annealing temperatures were: MSH1 primer, 5'-GAGACTGACGCGC-CCCAGCC-3' (SEQ ID NO:1) and 5'-CGCCTGGTCCAT-GAAAGTGACG-3' (SEQ ID NO:2), size 213 bp, annealing 65° C.; BMI1 primer, 5'-GAGACCAGCAAGTATTGTC-CTTTTG-3' (SEQ ID NO:3) and 5'-CATTGCT-GCTGGGCATCGTAAG-3' (SEQ ID NO:4), size 370 bp, annealing 59° C.; NESTIN primer, 5'-GGCAGCGTTG-GAACAGAGGTTGGA-3 (SEQ ID NO:5) and 5'-CTCTAAACTGGAGTGGTCAGGGCT-3' (SEQ ID NO:6), size 718 bp, annealing 65° C.; SOX2 primer, 5'-TAC-CTCTTCCTCCCACTCCA-3' (SEQ ID NO:7) and 5'-ACTCTCCTCTTTTGCACCCC-3' (SEQ ID NO:8), size 269 bp, annealing 59° C.; GAPDH primer, 5'-GAGGCAT-TGCTGATGATCTTG-3' (SEQ ID NO:9) and 5'-AGCCA-CATCGCTCAGAACAC-3' (SEQ ID NO:10), size 474 bp, annealing 65° C. A template control PCR was performed using GAPDH primers and with double distilled water instead of first-strand reaction mixture. PCR products were analyzed by agarose gel electrophoresis using DNA Molecular Marker VI as a size standard.

e) Whole-Genome Gene Expression.

All RNA was purified using standard methods. Sample amplification, labeling and hybridization on Illumina WG8 and WG6 Sentrix BeadChips were performed for all arrays in this study according to the manufacturer's instructions (Illumina) using an Illumina BeadStation (Burnham Institute Microarray Core).

f) Microarray Data Pre-Processing.

Raw data extraction was performed with BeadStudio v1.5 and probes with a detection score of less than 0.99 in all of the samples were discarded. The resulting probes were then quantile-normalized to correct for between-sample variation (Barnes et al. Nucleic Acids 33:5914-5923, 2005). The sample data were quality controlled before normalization using the quality parameters provided by BeadStudio software. Before and after normalization the arrays were inspected with signal distribution box plots and by using the maCorrPlot package (Ploner et al. Bioinformatics 6:80, 2005).

g) Parameters for Unsupervised Classification.

The data sets and the sparseness factor $\lambda$ were adjusted for the unsupervised clustering task following previous reports (Brunet et al. PNAS 101:4164-4169, 2004; Gao et al. Bioinformatics 21:3970-3975, 2005). Parameters used for this study were: SCM core data set (153 samples), $\lambda=0.01$; SCM test data set (219 samples), $\lambda=0.1$. The pre-processed data sets used can be downloaded at http://www.stemcellmatrix.info.

h) Gene Expression and Gene Set Analysis.

To screen for differentially expressed groups of genes between computationally defined sample clusters the Gene Set Analysis (GSA) methods were used (Subramanian et al. PNAS 102:1545-15550, 2005; Efron et al. Ann Appl Stat 1:107-129, 2007). GSA was chosen because it uses a stringent max-mean algorithm to identify significantly differentially regulated gene sets. The cutoff P-value was adjusted to accommodate a false discovery rate (FDR) of 10%. A translation file was built to use GSA with Illumina expression data. Gene lists from recent publications and public repositories (MolSigDB2, Stanford repository) were collected. These files can be downloaded from http://www.stemcellmatrix.org. To screen for differentially expressed genes between computationally defined sample clusters the standard t-test-based methods implemented in the R Bioconductor package (R Development Core Team, www.bioconductor.org, 2007, R Development Core Team, R: A Language and Environment for Statistical Computing, help files 2007). The cutoff P-value was adjusted to accommodate a FDR of 5%.

4. Consensus Clustering of Stem Cell Transcriptional Profiles

General Methodology. Unsupervised machine learning techniques were used to: (A) rediscover, de novo, the previously designated relationships between the cell lines, and (B) discover new relationships based on transcriptional profiles and explore the transcriptional similarity of different in vitro cell cultures. The Consensus Clustering framework (Monti et al. Machine Learning 52:91-118, 2003) was used to cluster transcription profiles and to assess stability of the discovered results. As a clustering algorithm, sparse non-negative matrix factorization was used (Gao et al. Bioinformatics 21:3970-5, 2005). For data perturbation, 30 sub-sampling runs were performed for each considered number of clusters (k). In each run 80% of the data was subjected to ten random restarts. The modified R-script can be downloaded at the accompanying website. Results for k12 are shown in FIG. 2 in the form of a consensus matrix. Consensus matrices for k2-15 can be found on the accompanying website.

Cophenetic correlation coefficient. Deciding on a "correct" number of clusters k is a difficult problem. Visual inspection of the consensus matrices, and of the corresponding summary statistics, can be used to determine the "optimal" number of clusters (Monti et al. Machine Learning 52:91-118, 2003). Brunet et al 2004 suggest the cophenetic correlation coefficient as valid summary statistics tool for this task (Brunet et al. PNAS 101:4164-9, 2004). The cophenetic correlation coefficient (Farris Systematic Zoology 18:279-285, 1969) is the Pearson correlation coefficient between pairwise distances of a set of objects and their cophenetic distances, which are derived from hierarchical clustering. The cophenetic distance of two objects is defined as the intergroup dissimilarity at which the two observations are first combined into a single cluster (R Development Core Team, www.bioconductor.org, 2007, R Development Core Team, R: A Language and Environment for Statistical Computing, help files 2007).

A high cophenetic correlation coefficient conveys that the clustering dendrogram reflects the original distances well. This implies that segregating the data into k groups is well supported by the co-occurrence data of the consensus clustering (Monti et al. Machine Learning 2003).

While the cophenetic correlation coefficient (Brunet et al. PNAS 101:4164-9, 2004; Sokal et al. Taxon 11:33-40, 1962) suggests that clustering is of high quality for k=12 for the Stem Cell Matrix core dataset and k=15 for the Stem Cell Matrix core plus test dataset, striking evidence for a single best k was not found (see FIG. 19 the respective cophenetic correlation plots over increasing k-runs). This is consistent with the observation that biologically meaningful clusters can be tracked through several k values (see FIG. 4).

Parameters for consensus clustering. The stability of the test dataset results were optimized within the consensus clustering framework by means of maximizing the cophenetic correlation coefficient. In the case of the test dataset, optimization for stable k-runs k≧12 were a primary goal. This was achieved by filtering the datasets for fold change and by setting genes with hybridization signals in the range of the background signal (<100) to a single fixed value in the same range (here: 100) in order to remove transcriptional noise. Previously, Brunet et al had used comparable steps for adjustment of the AML/ALL dataset for NMF (Brunet et al. PNAS 101:4164-9, 2004; Golub et al. Science 286:531-7, 1999). Lambda was also adjusted with the same intention and the cophenetic coefficient as readout. For details about the "sparseness factor" lambda ($\lambda$), please refer to Gao and Church (Gao et al. Bioinformatics 21:3970-5, 2005). The resulting parameters were: SCM core dataset (153 samples): no fold filtering, $\lambda=0.01$; SCM test dataset (219 samples): filtering for 10 fold change, $\lambda=0.1$.

a) Bootstrapped Sparse Non-Negative Matrix Factorization (bsNMF, See FIGS. 11 and 12)

In sparse NMF the matrix-decomposition process is forced by a "sparseness" factor lambda to reconstruct the data matrix with fewer features in the W-matrix than in the method proposed by Brunet and colleagues (Brunet et al. PNAS 101: 4164-9, 2004; Gao et al. Bioinformatics 21:3970-5, 2005). It was proposed that this results in more stable clustering at the cost of a higher reconstruction error when the algorithm detects a biologically relevant, optimal sample grouping. It has also been proposed by Gao and Church that this limited feature selection could lead to a machine learning-based identification of biologically meaningful gene sets in the W-matrix with biologically relevant co-expression patterns ("learning the parts of an object"; Lee et al. Nature 401:788-791, 1999), although this hypothesis awaits further validation (Gao et al. Bioinformatics 21:3970-5, 2005). For bootstrapped sNMF, it is first computed with ~80% randomly selected samples from the sample matrix with ten clusterings and ten random restart runs, the one with the smallest reconstruction error is retained. This procedure is repeated 30 times and these best 30 results are used for the computation of readouts from the Consensus Clustering framework. The bootstrapping modification is intended to increase the robustness of the reported results, avoiding sampling biases and technical variations. When this algorithm is applied to the Stem Cell Matrix Core Dataset, nine of the 12 clusters appear to be "pure" as judged by their Source Code annotation. Notably, the average size of the clusters does appear to be more homogenous than they are with other algorithms. NMF appears to maximize the number of "pure" clusters by allowing the existence of few heterogeneous clusters (best example: cluster 5).

5. The Below Algorithms are Mentioned in the Supplementary Discussion

Hierarchical Clustering (HIER, see FIGS. 22 and 23): HIER was one of the first methods successfully used for unsupervised class discovery in microarray data (Golub et al. Science 286:531-7, 1999). Agglomerative hierarchical clustering is a method that involves recursive merging of items (or groups of previously merged items). At each step, the distances between items (or groups of items) are calculated, and the closest pair of items is merged (Golub et al. Science 286:531-7, 1999). In the present study, HIER clustering results in relatively stable groupings. The cluster size appears to be either small (6 clusters with less than 6 samples) or large (3 clusters with more than 16 samples). Clusters 2, 3, 5, 7, 8 and 9 are "pure" clusters (consisting of only one Source Code category). Neural stem cells derived from hESC are clustered with undifferentiated hESCs (cluster 14). Although promising, these results are sub-optimal because HIER produces either heterogeneous, large clusters or more homogenous small clusters, thus providing a difficult starting point for possible generalizations based on statistical post-hoc analysis or network discovery methods.

K-Means Clustering (K-MEANS, see FIGS. 24 and 25): K-means groups items into specified numbers of clusters (k's). Initially, the centers of the clusters (centroids) are randomly selected from the items in the dataset. The distances between the items in the dataset and the centroids are then calculated, and each item is assigned to the nearest centroid to come up with the initial set of clusters. The center of each of these clusters is then calculated as the mean of its members, and the items are reassigned to the closest of these new centroids. These steps are repeated until the locations of the centroids remain stable between consecutive iterations.

k10 was selected because it represents the most stable model. Inspection of the group assignments reveals 6 "pure" clusters, one of them with most of the pluripotent stem cell samples in it. Again, there are 3 clusters of hESC-derived neural cells among these pure clusters. Inspection of the co-occurrence matrices and the cophenetic clustering coefficient reveals that the group assignment stability is well below that of the other algorithms.

Self-Organizing Maps (SOM, see FIGS. 26 and 27): SOMs are constructed by choosing a geometry of "nodes" on a grid. The nodes are mapped into k-dimensional space, initially at random, and then iteratively adjusted. Each iteration involves randomly selecting a data point and moving the nodes in the direction of this data point. The closest node is moved the most. The other nodes are moved by smaller distances depending on their location. Neighboring points in the initial topology tend to be mapped to nearby points in k-dimensional space. The process continues for many iterations. SOMs eventually find an optimal set of "centroids" around which the data points appear to aggregate. At k14, the cophenetic coefficient for SOM reaches a maximal value of just below 0.98. From inspection of the co-occurrence matrix it becomes obvious that there is one clear-cut, large cluster (cluster 3, HANSE cells) and that there are shifting and instable co-occurrence patterns in between all remaining groups. SOM clustering results in seven "pure" sample groups (cluster 1, 2, 3, 4, 5, 6, and 8), and all other clusters mix Source Code sample designations. Of note, pluripotent stem cells are presented in clusters 7, 9 and 11, each time mixing with neural cells. In this dataset, SOM clustering results appears to be rather unstable. When comparing the clustering results with similarly unstable results from the K-MEANS analysis, their biological interpretability also rather problematic. This is especially the case for clusters 4, 7, 9, 10, 11 and 14.

Non-Negative Matrix Factorization (NMF, see FIGS. 28 and 29): In contrast to the other three algorithms described here, which cluster items based on distance calculations, NMF uses matrix factorization to detect relations between items. The dataset can be represented as a large matrix, called the V matrix, which contains N mRNAs and M cell lines (Brunet et al. PNAS 101:4164-9, 2004). Over many iterations, NMF computes two component matrices, the W matrix (an N×k matrix) and the H matrix (a k×M matrix), which when multiplied together approximate the complete matrix for the dataset. Initial values in the W and H matrices are chosen randomly, and each iteration attempts to minimize the distance between WH and V (Brunet et al. PNAS 101:4164-9, 2004). Clustering of cell lines is read out from the H matrix, in which each entry is indexed to a cluster number and a cell line, and contains a value indicating how well the cell line fits in that cluster (Brunet et al. PNAS 101:4164-9, 2004).

The basic NMF algorithm as originally proposed by Brunet and colleagues achieves fairly good results with the current data. For this comparison, the k12 model was selected, for a better comparison, although the k13-model had a marginally (+0.008) higher cophenetic correlation coefficient. Nine clusters were "pure", although one of these clusters consists of only hESC-derived neural cell samples. Cluster 3 consists of cells with fibroblast-like morphology and similar culture conditions: Source codes: ePSC-XE, B-AS, BM-MLin (and sometimes also CT-Fib). This mirrors similar sample clusters that appear in every clustering algorithm tested so far: cluster 4 and 11 with HIER, cluster 6 with K-MEANS, cluster 12 with SOM and clusters 3 in sNMF and bootstrap sparse NMF (bsNMF). Close inspection of the co-occurrence matrix reveals that there are only few "co-occurrence shades" in between co-clustered samples in the NMF algorithm (FIG. 20D, cluster 3). This could mean that NMF "prefers" a limited number of solutions if the data perturbation is just re-started with random seeds as implemented in the standard consensus clustering paradigm. When, for example, cluster 3 is compared to its identically composed bootstrap sparse NMF counterpart in the k17 NMF run (FIG. 20 D/E), it becomes obvious that a much more graded picture of co-occurrence (as surrogate measure for similarity or dissimilarity) emerges. This is an important feature of the modification: bootstrapped NMF has a lesser likelihood for getting "locked in" algorithmic optima, which have no representation in the real world data structure.

Summary: Overall, the algorithms presented in this survey all give a similar impression on the general sample groupings in the core dataset: PSC do frequently co-cluster with other PSCs and with their in vitro derivatives such as neural stem cells derived from PSC (PSC-NLin). There is a tendency in all algorithms to group neural stem cells from fetal tissue together. Tissue-derived neural lineage cells are frequently separated from PSC-NLin cells and a group of neural progenitor cells that was derived from adult brain tissue.

Interestingly, there appears to be a consistent tendency shared among all algorithms to cluster seemingly different cell types such as fibroblasts, mesenchymal stem, cells, primitive extraembryonic endodermal cells and astrocytes into one group.

The quality of the clusterings varies considerably between the different methodologies in regard to stability of the results and the frequency of outliers (sample groups with just one or two members and clusters that appear to be anomalous because they group seemingly very different cell types together in a non-consistent manner over increasing k-numbers). Bootstrapped sparse NMF was selected for the purpose of this study, because it provided us with the best compromise between consistent, stable results and "pure" sample groups, which appear to reflect underlying biological patterns and signals reasonably well.

Notably, the MATISSE algorithm for the downstream analysis was designed in a way that should be robust against at least some sample outliers from the unsupervised clustering step. This was achieved by integrating the information from topological relationships, gene co-expression pattern as well as the sample groupings with a tradeoff parameter adjusting the relative importance of differential expression between the sample groups in the modified MATISSE similarity score.

While the results from all the different algorithms appear to be relatively consistent at lower k-numbers (data not shown), NMF appears to provide more robust results in with higher sample cluster numbers (k-10-20). This can be an important advantage in the task of classifying stem cells. To develop a reliable global classification of known and prospective stem cell classes it can be undesirable to limit the analysis to only a few similar transcriptional phenotypes, as it is the case in cancer studies, where usually a pre-selection for a specific disease entity (e.g. lymphomas or brain tumors) is the first step before transcriptional phenotypes are being employed to sub-categorize malignancies. The exact number of stem cell types is unknown, nor is it known whether to expect stem cells from different sources to be similar or different. The value of unbiased analysis is that it does not assume this knowledge.

a) Detection of Cluster-Specific Subnetworks Using MATISSE.

MATISSE (Ulitsky et al. BMC Syst Biol 1:8, 2007) (http://acgt.cs.tau.ac.il/matisse) was adjusted to detect differentially expressed connected subnetworks (DECs), corresponding to connected subnetworks in a physical interaction network that show a significant co-expression pattern. The physical network used by MATISSE contains vertices corresponding to genes and edges corresponding to protein-protein and protein-DNA interactions. For the present analysis the human physical interaction network was used that was previously assembled (Ulitsky et al. BMC Syst Biol 1:8, 2007) and augmented it with additional interactions from recent publications (Wang et al. Nature 444:364-368, 2006; Ewing et al. Mol Syst Biol 3:89, 2007; Mishra et al. Nucleic Acids Res 34:D411-D414, 2006). In total, the network contained 34,212 interactions among 9,355 proteins.

Originally, MATISSE used the Pearson correlation coefficient as a measure of similarity between the expression patterns of gene pairs. These similarity values serve as a starting point for the computation of pair-wise weights using a probabilistic model. The Pearson correlation between a pair of genes captures a global similarity trend between their expression patterns. Groups of genes were extracted that are not only similar across the experimental conditions, but also show significantly high or significantly low expression values in a specific subset of the samples, identified using the sNMF clustering scheme. A hybrid similarity score that captures two features was devised: (1) both genes show differential expression; (2) the genes have similar expression patterns, regardless of their differential expression.

The expression pattern of gene i is denoted by $x^i = (x^i_1, x^i_2, \ldots, x^i_m)$. Assume there is interest in DECs upregulated in a condition subset $A \subseteq \{1, \ldots, m\}$. To address goal (1), use an 'ideal' expression profile $p = (p_1, p_2, \ldots, p_m)$ where $p_i = 1$ if $i \in A$ and $p_i = -1$ otherwise. The signs are reversed if interest is in a DECS downregulated A. $r_{kp}$ is the Pearson correlation coefficient between $x^k$ and p. Intuitively, $r_{kp}$ is close to 1 if the corresponding transcript is strongly upregulated in A compared to the other conditions, and close to $-1$ if it is strongly downregulated in A. This measure has been suggested as an aparametric differential expression score (Troyanskaya et al. Bioinformatics 18:1454-1461, 2002). Note that the Pearson correlation is invariant under normalization of the patterns to zero mean and standard deviation of 1. For every gene pair (i,j) $S_{diff}(i,j) = (r_{ip} + r_{jp})/2$ is computed. To address goal (2) the partial correlation coefficient between the gene patterns conditioned on the ideal profile is used. Formally, $$S_{part}(i, j) = \frac{r^{ij}_{x,x} - r^i_{x,p} r^j_{x,p}}{\sqrt{(1 - r^{2i}_{x,p})(1 - r^{2j}_{x,p})}},$$

where $r_{yz}$, is the Pearson correlation coefficient between the profiles y and z. Intuitively, $S_{part}$ conveys the information about how similar $x^i$ and $x^j$ are, regardless of their differential expression in A. Finally, the similarity score $S = \lambda S_{diff} + S_{part}$ is used, where $\lambda$ is a trade-off parameter setting the relative importance of the differential expression in the similarity score. λ=3 is used for the current analysis. These S scores are then modeled using the probabilistic model described previously (Ulitsky et al. BMC Syst Biol 1:8, 2007). The advantage of using this pair-wise scoring scheme over the use of gene-specific differential expression scores, such as those proposed by others (Ideker et al. Bioinformatics 18:S233-S240, 2002), is that it prefers gene groups that are not only differentially expressed in the specified condition subset, but also have coherent expression profiles.

To diminish the effect of the size difference between the clusters, the number of conditions in clusters 1, 2, 3, 6, 9, 10 and 12 were reduced by including fewer replicates. Overall, 105 samples were used in the MATISSE analysis and can be downloaded at http://www.stemcellmatrix.org. This MATISSE variant was executed iteratively, each time setting A to contain all the samples of a single cluster or a cluster pair. The upper bound on module size was set to 300 and the rest of the parameters were as previously reported (Ulitsky et al. BMC Syst Biol 1:8, 2007). The resulting networks were then filtered by removing the DECs that overlapped more than 50% with other, higher scoring DECs. The full set of the DECs is available at http://www.stemcellmatrix.org.

b) Visualization.

For visualization of the selected DECs Cytoscape 2.5 (Cline et al. Nature Protocols 2:2366-2382, 2007) and Cerebral 2.0 (Barsky et al. Bioinformatics 23:1040-1042, 2007) were used. Localization data from HRPD and the G0-Molecular function categories were also used (Mishra et al. Nucleic Acids Res 34:D411-D414, 2006). NANOG, POU5F1/OCT4 and SOX2 promoter binding information was used to code the ESC-specific regulation of nodes (Boyer et al. Cell 122: 947-956, 2005). Permutmatrix was used for heat maps (Caraux et al. Bioinformatics 21:1280-1281, 2005). Data for the analysis of human oocytes were accessed on the authors' or the journals' website (Kocabas et al. PNAS 103:14027-14032, 2006). For analysis of iPSCs induced with LIN28, OCT4, NANOG and SOX2, the data set was obtained from the Thomson laboratory (Yu et al. Science 318:1917-1920, 2007).

c) Classification Based on PluriNet.

The 299 genes from DECS (Up(1,5)A) (PluriNet) were used with the PAM (Efron et al. Ann Appl Stat 1:107-129, 2007) software package. Class probabilities were re-computed 10,000 times; average scores are reported in FIGS. 12 and 14 The human genes were translated into their murine orthologues from PluriNet using the NCBI HomoloGene database for re-analyzing murine expression profiles. The expression array data from murine fibroblasts, induced pluripotent cells, epiblast-derived stem cells and murine embryonic stem cells were downloaded from NCBI GEO (Wange et al. Nature 444:364-368, 2006; Wang et al. Dev Cell 6,133-144, 2004; Chambers et al. Nature 450:1230-1234, 2007; Tesar et al. Nature 448:196-199, 2007).

F. References

Adewumi, O, et al. Characterization of human embryonic stem cell lines by the International Stem cell Initiative. *Nature Biotechnol.* 25, 803-816 (2007).

Allison, D. B., Cui, X., Page, G. P. & Sabripour, M. Microarray data analysis: from disarray to consolidation and consensus. Nat Rev Genet 7, 55-65 (2006).

Bar-Joseph, Z. et al. Genome-wide transcriptional analysis of the human cell cycle identifies genes differentially regulated in normal and cancer cells. Proc Natl Acad Sci USA 105, 955-60 (2008).

Barnes, M. Freudenberg, J., Thompson, S., Aronow, B & Pavlidis, P. Experimental comparison and cross-validation of the Affymetrix and Illumina gene expression analysis platforms. *Nucleic Acids Res.* 33, 5914-5923 (2005).

Barsky, A., Gardy, J. L., Hancock, R. E. & Munzner, T. Cerebral: a Cytoscape plugin for layout and interaction with biological networks using subcellular localization annotation. *Bioinformatics* 23, 1040-1042 (2007).

Becker, K. A. et al. Self-renewal of human embryonic stem cells is supported by a shortened G1 cell cycle phase. J Cell Physiol 209, 883-93 (2006).

Becker, K. A., Stein, J. L., Lian, J. B.; van Wijnen, A. J. & Stein, G. S. Establishment of histone gene regulation and cell cycle checkpoint control in human embryonic stem cells. J Cell Physiol 210, 517-26 (2007).

Boyer, L. A. et al. Core transcriptional regulatory circuitry in human embryonic stem cells. *Cell* 122, 947-956 (2005).

Brons, I. G. et al. Derivation of pluripotent epiblast stem cells from mammalian embryos. Nature 448, 191-5 (2007).

Brunet, J. P., Tamayo P., Golub, T. R. & Mesirov, J. P. Metagenes and molecular pattern discovery using matrix factorization. *Proc. Natl. Acad. Sci. USA* 101, 4164-4169 (2004).

Byrne, J., Simonsson, S., Western, P. & Gurdon, J. Nuclei of adult mammalian somatic cells are directly reprogrammed to oct-4 stem cell gene expression by amphibian oocytes. Curr Biol 13, 1206-13 (2003).

Caraux, G. & Pinloche, S. PermutMatrix: a graphical environment to arrange gene expression profiles in optimal linear order. *Bioinformatics* 21, 1280-1281 (2005).

Carpenter, M. K., Rosier, E. & Rao, M. S. Characterization and differentiation of human embryonic stem cells. *Cloning Stem Cells* 5, 79-88 (2003).

Chambers, I. et al. Nanog safeguards pluripotency and mediates germline development. *Nature* 450, 1230-1234 (2007).

Cline, M. S. et al. Integration of biological networks and gene expression data using Cytoscape. *Nature Protocols* 2, 2366-2382 (2007).

Cooper, S. & Shedden, K. Microarrays and the relationship of mRNA variation to protein variation during the cell cycle. J Theor Biol 249, 574-81 (2007).

Cooper, S. Rejoinder: whole-culture synchronization cannot, and does not, synchronize cells. Trends Biotechnol 22, 274-6 (2004).

Cowan, C. A. et al. Derivation of embryonic stem-cell lines from human blastocysts. *N. Engl. J. Med.* 350, 1353-1356 (2004).

Cowan, C., Atienza, J., Melton, D. & Eggan, K. Nuclear reprogramming of somatic cells after fusion with human embryonic stem cells. Science 309, 1369-73 (2005).

Donoho, D. & Stodden, V. When does non-negative matrix factorization give correct decomposition into parts? *Proc. NIPS* (2003) (http://books.nips.cc/papers/files/nips16/NIPS2003_LT10.ps.gz).

Efron, B. & Tibshirani, R. On testing the significance of sets of genes. *Ann. Appl. Stat.* 1, 107-129 (2007).

Eppig, J. T. et al. The Mouse Genome Database (MGD): from genes to mice—a community resource for mouse biology. Nucleic Acids Res 33, D471-5 (2005).

Ewing, R. M. et al. Large-scale mapping of human protein-protein interactions by mass spectrometry. *Mol. Syst. Biol.* 3, 89 (2007).

Farris, J. S. On the cophenetic correlation coefficient. Systematic Zoology 18, 279-285 (1969).

Fluckiger, A. C. et al. Cell cycle features of primate embryonic stem cells. Stem Cells 24, 547-56 (2006).

Gao, Y. & Church, G. Improving molecular cancer class discovery through sparse non-negative matrix factorization. *Bioinformatics* 21, 3970-3975 (2005).

Gearhart, J. New human embryonic stem-cell lines—more is better. N Engl J Med 350, 1275-6 (2004).

Geijsen, N. et al. Derivation of embryonic germ cells and male gametes from embryonic stem cells. Nature 427, 148-54 (2004).

Goldman, B. Magic marker myths. *Nature Reports Stem Cells*. doi:10.1038/stemcells.2008.26 (2008).

Golub, T. R. et al. Molecular classification of cancer: class discovery and class prediction by gene expression monitoring. *Science* 286, 531-537 (1999).

Hatano, S. Y. et al. Pluripotential competence of cells associated with Nanog activity. Mech Dev 122, 67-79 (2005).

Hubner, K. et al. Derivation of oocytes from mouse embryonic stem cells. Science 300, 1251-6 (2003).

Ideker, T., Ozier, O., Schwikowski, B. & Siegel, A. F. Discovering regulatory and signaling circuits in molecular interaction networks. *Bioinformatics* 18 (suppl. 1), S233-S240 (2002)

Imitola, J. et al. Directed migration of neural stem cells to sites of CNS injury by the stromal cell-derived factor 1α/CXC chemokine receptor 4 pathway. *Proc. Natl. Acad. Sci. USA* 101, 18117-18122 (2004).

Jacobson, B. S. & Ryan, U.S. Growth of endothelial and HeLa cells on a new multipurpose microcarrier that is positive, negative or collagen coated. Tissue Cell 14, 69-83 (1982).

Josephson, R. et al. Qualification of embryonal carcinoma 2102Ep as a reference for human embryonic stem cell research. Stem Cells 25, 437-46 (2007).

Kehler, J., Hubner, K., Garrett, S. & Scholer, H. R. Generating oocytes and sperm from embryonic stem cells. Semin Reprod Med 23, 222-33 (2005).

Kittler, R. et al. Genome-scale RNAi profiling of cell division in human tissue culture cells. Nat Cell Biol 9, 1401-12 (2007).

Kocabas, A. et al. The transcriptome of human oocytes. *Proc. Natl. Acad. Sci. USA* 103, 14027-14032 (2006).

Kornblum, H. I. & Geschwind, D. H. Molecular markers in CNS stem cell research: hitting a moving target. *Nature Rev. Neurosci.* 2, 843-846 (2001).

Lacayo, N. J. et al. Gene expression profiles at diagnosis in de novo childhood AML patients identify FLT3 mutations with good clinical outcomes. *Blood* 104, 2646-2654 (2004).

Maherali, N. et al. Directly Reprogrammed Fibroblasts Show Global Epigenetic Remodeling and Widespread Tissue Contribution. Cell Stem Cell 1, 55-70 (2007).

Meissner, A., Wernig, M. & Jaenisch, R. Direct reprogramming of genetically unmodified fibroblasts into pluripotent stem cells. Nat Biotechnol (2007).

Mishra, G. R. et al. Human protein reference database-2006 update. *Nucleic Acids Res.* 34, D411-D414 (2006).

Mitsui, K. et al. The homeoprotein Nanog is required for maintenance of pluripotency in mouse epiblast and ES cells. Cell 113, 631-42 (2003).

Monti, S., Tamayo, P., Mesirov, J. & Golub, T. Consensus clustering: A resampling-based method for class discovery and visualization of gene expression microarray data. *Mach. Learn.* 52, 91-118 (2003).

Mukherji, M. et al. Genome-wide functional analysis of human cell-cycle regulators. Proc Natl Acad Sci USA 103, 14819-24 (2006).

Müller, F. J., Snyder, E. Y. & Loring, J. F. Gene Therapy: can neural stem cells deliver? *Nature Rev. Neurosci.* 7, 75-84 (2006).

Murry, C. E. & Keller, G. Differentiation of embryonic stem cells to clinically relevant populations: lessons from embryonic development. *Cell* 132, 661-680 (2008).

Nakagawa, M. et al. Generation of induced pluripotent stem cells without Myc from mouse and human fibroblasts. Nat Biotechnol (2007).

Okita, K., Ichisaka, T. & Yamanaka, S. Generation of germline-competent induced pluripotent stem cells. *Nature* 448, 313-317 (2007).

Palmer, T. D. et al. Cell culture. Progenitor cells from human brain after death. *Nature* 411, 42-43 (2001).

Park, I. H. et al. Reprogramming of human somatic cells to pluripotency with defined factors. Nature 451, 141-146 (2008).

Pera, M. F., Blasco Lafita, M. J. & Mills, J. Cultured stem-cells from human testicular teratomas: the nature of human embryonal carcinoma, and its comparison with two types of yolk-sac carcinoma. Int J Cancer 40, 334-43 (1987).

Pera, M. F., Cooper, S., Mills, J & Parrington, J. M. Isolation and characterization of a multipotent clone of human embryonal carcinoma cells. Differentiation 42, 10-23 (1989).

Ploner, A., Miller, L. D., Hall, P., Bergh, J & Pawitan, Y. Correlation test to assess low-level processing of high-density oligonucleotide microarray data. *BMC Bioinformatics* 6, 80 (2005).

R Development Core Team, R. A language and environment for statistical computing, help files. (http://www.bioconductor.org/) (2007).

Reubinoff, B. E., Pera, M. F., Fong, C. Y., Trounson, A. & Bongso, A. Embryonic stem cell lines from human blastocysts: somatic differentiation in vitro. Nat Biotechnol 18, 399-404 (2000).

Richards, M., Fong, C. Y., Chan, W. K., Wong, P. C. & Bongso, A. Human feeders support prolonged undifferentiated growth of human inner cell masses and embryonic stem cells. Nat Biotechnol 20, 933-6 (2002).

Schwartz, P. H. et al. Isolation and characterization of neural progenitor cells from post-mortem human cortex. *J. Neurosci. Res.* 74, 838-851 (2003).

Sokal, R. & Rohlf, F. The comparison of dendrograms by objective methods. Taxon 11, 33-40 (1962).

Son, Y. S. et al. Heat shock 70-kDa protein 8 isoform 1 is expressed on the surface of human embryonic stem cells and downregulated upon differentiation. Stem Cells 23, 1502-13 (2005).

Subramanian, A. et al. Gene set enrichment analysis: a knowledge-based approach for interpreting genome-wide expression profiles. *Proc. Natl. Acad. Sci. USA* 102, 15545-15550 (2005).

Tada, M., Takahama, Y., Abe, K., Nakatsuji, N. & Tada, T. Nuclear reprogramming of somatic cells by in vitro hybridization with ES cells. Curr Biol 11, 1553-8 (2001).

Takahashi, K. & Yamanaka, S. Induction of pluripotent stem cells from mouse embryonic and adult fibroblast cultures by defined factors. *Cell* 126, 663-676 (2006).

Takahashi, K. et al. Induction of pluripotent stem cells from adult human fibroblasts by defined factors. *Cell* 131, 861-872 (2007).

Takahashi, K., Okita, K., Nakagawa, M. & Yamanaka, S. Induction of pluripotent stem cells from fibroblast cultures. Nat Protoc 2, 3081-9 (2007).

Tesar, P. J. et al. New cell lines from mouse epiblast share defining features with human embryonic stem cells. *Nature* 448, 196-199 (2007).

Troyanskaya, O., Garber, M., Brown, P., Botstein, D. & Altman, R. Nonparametric methods for identifying differentially expressed genes in microarray data. *Bioinformatics* 18, 1454-1461 (2002).

Ulitsky, I. & Shamir, R. Identification of functional modules using network topology and high-throughput data. *BMC Syst. Biol.* 1, 8 (2007).

Wang, H. & Dey, S. K. Roadmap to embryo implantation: clues from mouse models. Nat. Rev. Genet. 7, 185-99 (2006).

Wang, J. et al. A protein interaction network for pluripotency of embryonic stem cells. *Nature* 444, 364-368 (2006).

Wang, Q. T. et al. A genome-wide study of gene activity reveals developmental signaling pathways in the preimplantaion mouse embryo. *Dev. Cell* 6, 133-144 (2004).

296. Ware, C. B., Nelson, A. M. & Blau, C. A. A comparison of NIH-approved human ESC lines. Stem Cells 24, 2677-84 (2006).

Wernig, M. et al. In vitro reprogramming of fibroblasts into a pluripotent ES-cell-like state. Nature (2007).

West, J. A., Park, I. H., Daley, G. Q. & Geijsen, N. In vitro generation of germ cells from murine embryonic stem cells. Nat Protoc 1, 2026-36 (2006).

Wood, J., Dumesic, D., Abbott, D. & Strauss, J. Molecular abnormalities in oocytes from women with polycystic ovary syndrome revealed by microarray analysis. J Clin Endocrinol Metab 92, 705-13 (2007).

Yu, J. et al. Induced pluripotent stem cell lines derived from human somatic cells. *Science* 318, 1917-1920 (2007).

Zeng, X. et al. BG01V: a variant human embryonic stem cell line which exhibits rapid growth after passaging and reliable dopaminergic differentiation. *Restor. Neurol. Neurosci.* 22, 421-428 (2004).

We claim:

1. A computer-implemented method of assaying a cell comprising:
    providing said computer with a reference database, wherein the reference database comprises cell datasets produced from characteristic data including global profile information for at least one-hundred fifty known cell lines, tissues, or primary cells and at least one dataset produced for each of human embryonic stem cells, human induced pluripotent stem cells and human somatic multipotent cells;
    receiving a test dataset in said computer, wherein the test dataset comprises data including global profile information for a cell line, tissue, or primary cell of previously unknown pluripotency;
    merging the test dataset into the reference database producing an updated reference database; and
    performing in said computer unsupervised classification of the updated reference database thereby producing a computed label classification of the test dataset, wherein the computed label classification includes an indication of whether or not the cell line, tissue, or primary cell in the test dataset is pluripotent or contains pluripotent cells.

2. The method of claim 1, further comprising the step of performing automatic model selection producing a best fitting classification model, wherein the best fitting classification model is a model that an algorithm identifies as most stable to random perturbations.

3. The method of claim 2, further comprising identifying in which cluster or clusters the unknown cell is grouped.

4. The method of claim 3, further comprising outputting a computed definition of the unknown cell wherein the computed definition is referenced to the cluster in which the unknown cell resides.

5. The method of claim 4, wherein the best fitting classification model can cluster the individual datasets such that each dataset within a cluster is indistinguishable from each other dataset within the cluster.

6. The method of claim 4, wherein the best fitting classification model can cluster the individual datasets such that each dataset within a cluster is similar to each other individual dataset in the cluster.

7. The method of claim 6, further comprising identifying computationally derived class labels based only on biological characteristics.

8. The method of claim 7, further comprising identifying differences in at least one dataset for at least one label between at least two samples in at least two clusters.

9. The method of claim 8, further comprising filtering within a cluster for samples having a similar label profile.

10. The method of claim 9, further comprising defining differentially regulated protein-protein networks.

11. The method of claim 10, further comprising using the protein-protein networks to define a class membership, manipulate class membership, or define biological function of an unknown cell.

12. The method of claim 4, wherein the best fitting classification model can cluster the individual datasets such that each dataset within a cluster is different from each other individual dataset.

13. The method of claim 1, wherein performing unsupervised classification of the updated reference database comprises clustering RNA, DNA and/or protein profiles.

14. The method of claim 1, wherein the global profile information is obtained from microarray analysis of cellular RNA.

15. The method of claim 1, wherein performing unsupervised machine classification comprises a bootstrapping sparse non-negative matrix factorization.

16. The method of claim 1, wherein the reference database comprises transcriptional profiles for stem cells.

17. The method of claim 1, further comprising classifying cells based on computationally derived protein-protein network.

18. The method of claim 1, wherein the global profile is a transcriptional profile.

19. The method of claim 1, wherein the reference database comprises known class labels.

20. The method of claim 1, further comprising the step of outputting results from the unsupervised classification.

21. The method of claim 1, wherein the reference database is provided on a storage medium.

22. The method of claim 1, wherein receiving the test dataset comprises receiving input from a computer system.

23. The method of claim 1, wherein receiving the test dataset comprises receiving input from an array analysis system.

24. The method of claim 1, wherein receiving the test dataset comprises receiving input via a computer network.

25. The method of claim 1, wherein the data in the reference database is associated with one or more labeled associated biological classes of the cells.

26. A computer program product comprising a non-transitory machine readable medium on which is provided program instructions, the program instructions comprising:
    code for receiving a test dataset, wherein the test dataset comprises data including global profile information for a cell line, tissue, or primary cell of previously unknown pluripotency;

code for merging the test dataset into the reference database producing an updated reference database, wherein the reference database comprises cell datasets produced from characteristic data including global profile information for at least one-hundred fifty known cell lines, tissues, or primary cells and at least one dataset produced for each of human embryonic stem cells, human induced pluripotent stem cells and human somatic multipotent cells;

code for performing unsupervised classification of the updated reference database producing a computed label classification of the test dataset, wherein the computed label classification includes an indication of whether or not the cell line, tissue, or primary cell in the test dataset is pluripotent or contains pluripotent cells.

27. A computer-implemented method comprising:

providing said computer with a reference database, wherein the reference database comprises cell datasets produced from characteristic data including global profile information for at least one-hundred fifty known cell lines, tissues, or primary cells and at least one dataset produced for each of human embryonic stem cells, human induced pluripotent stem cells and human somatic multipotent cells;

receiving a test dataset in said computer, wherein the test dataset comprises data including global profile information for a cell line, tissue, or primary cell of previously unknown pluripotency;

merging the test dataset into the reference database producing an updated reference database; and performing in said computer unsupervised classification of the updated reference database thereby producing a computed label classification of the test dataset, wherein the computed label classification includes an indication of whether or not the cell line, tissue, or primary cell in the test dataset has a biological characteristic of interest.

* * * * *